(12) United States Patent
Ashwell et al.

(10) Patent No.: US 7,423,061 B2
(45) Date of Patent: Sep. 9, 2008

(54) SUBSTITUTE THIOPHENES AND USES THEREOF

(75) Inventors: Susan Ashwell, Waltham, MA (US); Thomas Gero, Waltham, MA (US); Stephanos Ioannidis, Waltham, MA (US); James Janetka, Waltham, MA (US); Paul Lyne, Waltham, MA (US); Vibha Oza, Waltham, MA (US); Stephanie Springer, Cambridge, MA (US); Mei Su, Waltham, MA (US); Dingwei Yu, Waltham, MA (US)

(73) Assignee: AstraZeneca AB, Sodertalje (SE)

(*) Notice: Subject to any disclaimer, the term of this patent is extended or adjusted under 35 U.S.C. 154(b) by 0 days.

(21) Appl. No.: 10/568,380

(22) PCT Filed: Aug. 12, 2004

(86) PCT No.: PCT/GB2004/003473

§ 371 (c)(1),
(2), (4) Date: Feb. 14, 2006

(87) PCT Pub. No.: WO2005/016909

PCT Pub. Date: Feb. 24, 2005

(65) Prior Publication Data

US 2006/0281666 A1  Dec. 14, 2006

Related U.S. Application Data

(60) Provisional application No. 60/576,416, filed on May 28, 2004, provisional application No. 60/495,580, filed on Aug. 15, 2003.

(51) Int. Cl.
*A61K 31/381* (2006.01)
*C07D 333/04* (2006.01)

(52) U.S. Cl. ............ 514/447; 549/29; 549/68; 549/69; 549/200; 549/429; 514/438; 514/448; 546/184; 546/192; 546/268.1; 548/517; 548/527; 548/950

(58) Field of Classification Search ............ 549/29, 549/68, 69; 514/438, 447, 448; 546/184, 546/192, 268.1; 548/517, 527, 950
See application file for complete search history.

(56) References Cited

U.S. PATENT DOCUMENTS 7,125,896 B2 * 10/2006 Faull et al. ............ 514/336
2007/0010556 A1  1/2007 Ashwell et al.

FOREIGN PATENT DOCUMENTS

| WO | 9852558 A1 | 11/1998 |
|---|---|---|
| WO | 01058890 A1 | 8/2001 |
| WO | 0198290 A2 | 12/2001 |
| WO | 02030353 A2 | 4/2002 |
| WO | 02070494 A1 | 9/2002 |
| WO | 03028731 A1 | 4/2003 |
| WO | 03029241 A1 | 4/2003 |
| WO | 03029242 A1 | 4/2003 |
| WO | WO 03/029241 A1 * | 4/2003 |
| WO | 03104218 A1 | 12/2003 |
| WO | 2004053087 A2 | 6/2004 |
| WO | 2004063185 A1 | 7/2004 |
| WO | 2005033102 A2 | 4/2005 |
| WO | 2005105777 A1 | 11/2005 |
| WO | 2006062982 A2 | 6/2006 |
| WO | 2006062984 A2 | 6/2006 |

OTHER PUBLICATIONS

Baxter et al (2001): STN International HCAPLUS database, Columbus (OH), accession No. 2001: 597977.*
Parrish et al (2003): STN International HCAPLUS database, Columbus (OH), accession No. 2003: 282559.*
Baxter et al. Hit-to-lead studies: the discovery of potent, orally active, thiophenecarboxamide IKK -2 inhibitors. Bioorganic & Medicinal Chemistry Letters (2004), 14(11), 2817-2822.
AstraZeneca PLC, Novel thiophenecarboxamide IKK -2 inhibitors. Expert Opinion on Therapeutic Patents (2005), 15(3), 343-347.

* cited by examiner

*Primary Examiner*—Golam M Shameem

(57) ABSTRACT

This invention relates to novel compounds having the structural formula (I) and to their pharmaceutical salts, compositions and methods of use. These novel compounds provide a treatment or prophylaxis of cancer.

17 Claims, No Drawings

SUBSTITUTE THIOPHENES AND USES THEREOF

CROSS-REFERENCE TO RELATED APPLICATIONS

This application is a U.S. National Stage under 35 U.S.C. § 371 of International Application No. PCT/GB2004/003473 (filed Aug. 12, 2004) which claims the benefit under 35 U.S.C. § 119(e) to U.S. Provisional Applications No. 60/495,580 filed on Aug. 15, 2003 and Ser. No. 60/576,416 filed May 28, 2004.

FIELD OF THE INVENTION

The present invention relates to novel substituted thiophenes, their pharmaceutical compositions and methods of use. In addition, the present invention relates to therapeutic methods for the treatment and prevention of cancers.

BACKGROUND OF THE INVENTION

Chemotherapy and radiation exposure are currently the major options for the treatment of cancer, but the utility of both these approaches is severely limited by adverse effects on normal tissue, and the frequent development of tumor cell resistance. It is therefore desirable to improve the efficacy of such treatments in a way that does not increase the toxicity associated with them. One way to achieve this is by the use of specific sensitizing agents such as those described herein.

An individual cell replicates by making an exact copy of its chromosomes, and then segregating these into separate cells. This cycle of DNA replication, chromosome separation and division is regulated by mechanisms within the cell that maintain the order of the steps and ensure that each step is precisely carried out. Involved in these processes are the cell cycle checkpoints (Hartwell et al., *Science*, Nov. 3, 1989, 246(4930):629-34) where cells may arrest to ensure DNA repair mechanisms have time to operate prior to continuing through the cycle into mitosis. There are two such checkpoints in the cell cycle—the G1/S checkpoint that is regulated by p53 and the G2/M checkpoint that is monitored by the Ser/Thr kinase checkpoint kinase 1 (CHK1).

The cell cycle arrest induced by these checkpoints is a mechanism by which cells can overcome the damage resulting from radio- or chemotherapy, their abrogation by novel agents should increase the sensitivity of tumor cells to DNA damaging therapies. Additionally, the tumor specific abrogation of the G1/S checkpoint by p53 mutations in the majority of tumors can be exploited to provide tumor selective agents. One approach to the design of chemosensitizers that abrogate the G2/M checkpoint is to develop inhibitors of the key G2/M regulatory kinase CHK1, and this approach has been shown to work in a number of proof of concept studies. (Koniaras et al., *Oncogene*, 2001, 20:7453; Luo et al., *Neoplasia*, 2001, 3:411; Busby et al., *Cancer Res.*, 2000, 60:2108; Jackson et al., *Cancer Res.*, 2000, 60:566).

SUMMARY OF THE INVENTION

Provided herein are novel compounds of structural formula (I) or a pharmaceutically acceptable salt thereof:

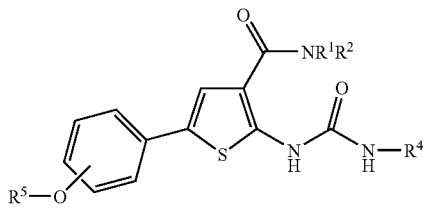

wherein:
  $R^1$ and $R^2$ are at each occurrence independently selected from H, optionally substituted $C_{1-6}$alkyl, or optionally substituted heterocyclyl; with the proviso that $R^1$ and $R^2$ are not both H; or $R^1$ and $R^2$ and the N to which they are attached in combination form an optionally substituted heterocyclyl;
  $R^4$ is selected from H, OH, optionally substituted carbocyclyl, optionally substituted heterocyclyl, or optionally substituted $C_{1-6}$alkyl;
  $R^5$ is selected from H, optionally substituted carbocyclyl, or optionally substituted $C_{1-6}$alkyl.

The invention also encompasses stereoisomers, enantiomers, in vivo-hydrolysable precursors and pharmaceutically-acceptable salts of compounds of formula I, pharmaceutical compositions and formulations containing them, methods of using them to treat diseases and conditions either alone or in combination with other therapeutically-active compounds or substances, processes and intermediates used to prepare them, uses of them as medicaments, uses of them in the manufacture of medicaments and uses of them for diagnostic and analytic purposes.

DETAILED DESCRIPTION OF THE INVENTION

Provided herein are novel compounds of structural formula (I) or a pharmaceutically acceptable salt or an in vivo-hydrolysable precursor thereof:

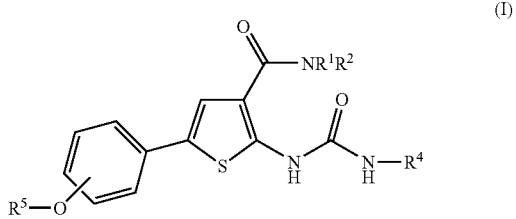

wherein:
  $R^1$ and $R^2$ are at each occurrence independently selected from H, optionally substituted $C_{1-6}$alkyl, or optionally substituted heterocyclyl; with the proviso that $R^1$ and $R^2$ are not both H; or $R^1$ and $R^2$ and the N to which they are attached in combination form an optionally substituted heterocyclyl;
  $R^4$ is selected from H, OH, optionally substituted carbocyclyl, optionally substituted heterocyclyl, or optionally substituted $C_{1-6}$alkyl;
  $R^5$ is selected from H, optionally substituted carbocyclyl, or optionally substituted $C_{1-6}$alkyl.

One embodiment of the present invention provides compounds of formula (I) or a pharmaceutically acceptable salt or an in vivo-hydrolysable precursor wherein $R^1$ is an optionally substituted heterocyclyl.

One embodiment of the present invention provides compounds of formula (I) or a pharmaceutically acceptable salt or an in vivo-hydrolysable precursor wherein $R^1$ is an optionally substituted heterocyclyl wherein 1, 2, or 3 substitutents is/are independently selected from halogen, nitro, amino, cyano, trifluoromethyl, alkyl, alkenyl, alkynyl, haloalkyl, alkoxy, hydroxy, alkylhydroxy, carbonyl, —CH(OH)CH$_3$, —CH$_2$NH-alkyl-OH, alkyl-(OH)CH$_3$, —CH$_2$-phenyl-(OCH$_3$)$_2$, —Oalkyl, —OCH$_3$, —Ophenyl, —OCOalkyl, —NHCHO, -Nalkyl, —N-(alkyl)-CHO, —NH—CO-amino, —N-(alkyl)-CO-amino, —NH—COalkyl, —N-(alkyl)-COalkyl, -carboxy, -amidino, —CO-amino, —CO-alkyl, —CO$_2$alkyl, mercapto, —Salkyl, —SCH$_2$furanyl, —SO(alkyl), —SO$_2$(alkyl), —SO$_2$-amino, -alkylsulfonylamino, phenyl, anisole, dimethoxyphenyl, trimethoxyphenyl, halophenyl, cycloalkyl, heterocyclyl, -alkyl-NH-cycloalkyl, -alkyl-NH-heterocyclyl, -alkyl-NH-alkyl-OH, —C(═O)OC(CH$_3$)$_3$, —N(CH$_3$)$_2$, —N(CH$_2$CH$_3$)$_2$, -alkyl-NH-alkyl-heterocyclyl, -alkyl-aryl, -methyl-phenyl, alkyl-polycyclyl, alkyl-amino, alkyl-hydroxy, —CH$_2$NH-alkyl-heterocyclyl, —CH$_2$NHCH2CH(CH$_3$)$_2$, vicinal —O(alkyl)O—, vicinal —OC(haloalkyl)O—, vicinal —CH$_2$O(alkyl)O—, vicinal —S(alkyl)S— and —O(alkyl)S—.

One embodiment of the present invention provides compounds of formula (I) or a pharmaceutically acceptable salt or an in vivo-hydrolysable precursor wherein $R^1$ is an optionally substituted heterocyclyl wherein 1, 2, or 3 substitutents is/are independently-selected from: —OH, C(═O)OC(CH$_3$)$_3$, NH$_2$, C$_{1-6}$alkyl, methoxybenzene, or dimethoxy benezene.

One embodiment of the present invention provides compounds of formula (I) or a pharmaceutically acceptable salt or an in vivo-hydrolysable precursor wherein $R^1$ is a heterocyclyl wherein heterocyclyl is selected from piperdinyl, pyridinyl, pyrrolidinyl, pyrazinyl, azepanyl, azetidinyl, azabicyclozinyl, furanyl, thienyl.

One embodiment of the present invention provides compounds of formula (I) or a pharmaceutically acceptable salt or an in vivo-hydrolysable precursor wherein $R^2$ is H.

One embodiment of the present invention provides compounds of formula (I) or a pharmaceutically acceptable salt or an in vivo-hydrolysable precursor wherein $R^4$ is H.

One embodiment of the present invention provides compounds of formula (I) or a pharmaceutically acceptable salt or an in vivo-hydrolysable precursor wherein $R^5$ is H or an optionally substituted C$_{1-6}$alkyl.

One embodiment of the present invention provides compounds of formula a) or a pharmaceutically acceptable salt or an in vivo-hydrolysable precursor wherein $R^5$ is H or an optionally substituted C$_{1-6}$alkyl wherein 1, 2 or 3 substitutents is/are independently selected from: NH$_2$, NHCH$_3$, N(CH$_2$CH$_3$)$_2$, N(CH$_3$)$_2$, OCH$_3$, OH, —C$_{1-6}$alkyl, morpholino, piperidinyl, pyrrolodinyl.

One embodiment of the present invention provides compounds of formula (I) or a pharmaceutically acceptable salt or an in vivo-hydrolysable precursor wherein $R^5$ is H or an optionally substituted C$_{1-3}$alkyl.

One embodiment of the present invention provides compounds of formula (I) or a pharmaceutically acceptable salt or an in vivo-hydrolysable precursor wherein $R^5$ is H or an optionally substituted C$_{1-3}$alkyl wherein 1, 2 or 3 substitutents is/are independently selected from: NH$_2$, NHCH$_3$, N(CH$_2$CH$_3$)$_2$, N(CH$_3$)$_2$, OCH$_3$, OH, —C$_{1-6}$alkyl, morpholino, piperidinyl, pyrrolodinyl.

One embodiment of the present invention provides compounds of formula (I) or a pharmaceutically acceptable salt or an in vivo-hydrolysable precursor wherein
$R^1$ is an optionally substituted heterocyclyl;
$R^2$ is H;
$R^4$ is H;
$R^5$ is H or an optionally substituted C$_{1-6}$alkyl.

One embodiment of the present invention provides compounds of formula (I) or a pharmaceutically acceptable salt or an in vivo-hydrolysable precursor wherein:
$R^1$ is an optionally substituted heterocyclyl wherein the substitutent is selected from one or more of the following: —NH$_2$, C$_{1-6}$alkyl, —C(═O)OC(CH$_3$)$_3$,
$R^2$ is H;
$R^4$ is H;
$R^5$ is H or an optionally substituted C$_{1-6}$alkyl wherein the substitutent is selected from one or more of the following: —C$_{1-6}$alkyl, —N(C$_{1-3}$alkyl)$_2$.

One embodiment of the present invention provides compounds of formula (I) or a pharmaceutically acceptable salt or an in vivo-hydrolysable precursor wherein:
$R^1$ is an optionally substituted heterocyclyl wherein the substitutent is selected from one or more of the following: —NH$_2$, C$_{1-6}$alkyl, —C(═O)OC(CH$_3$)$_3$,
$R^2$ is H;
$R^4$ is H;
$R^5$ is H or an optionally substituted C$_{1-3}$alkyl wherein 1, 2 or 3 substitutents is/are independently selected from: NH$_2$, NHCH$_3$, N(CH$_2$CH$_3$)$_2$, N(CH$_3$)$_2$, OCH$_3$, OH, —C$_{1-6}$alkyl, morpholino, piperidinyl, pyrrolodinyl.

One embodiment of the present invention provides compounds of formula (I) or a pharmaceutically acceptable salt or an in vivo-hydrolysable precursor wherein:
$R^1$ is a heterocyclyl;
$R^2$ is H;
$R^4$ is H;
$R^5$ is H or a C$_{1-6}$alkyl.

One embodiment of the present invention provides compounds of formula (I) or a pharmaceutically acceptable salt or an in vivo-hydrolysable precursor wherein:
$R^1$ is a 6-membered heterocyclyl containing at least one N in the ring;
$R^2$ is H;
$R^4$ is H;
$R^5$ is a C$_{1-3}$alkyl.

One embodiment of the present invention provides compounds of formula (I) selected from the following:
tert-butyl 3-{[(2-[(aminocarbonyl)amino]-5-{4-[2-(diethylamino)ethoxy]phenyl}-3-thienyl)carbonyl]amino}piperidine-1-carboxylate;
2-[(aminocarbonyl)amino]-5-{4-[2-(diethylamino)ethoxy]phenyl}-N-piperidin-3-ylthiophene-3-carboxamide;
2-[(aminocarbonyl)amino]-5-{3-[2-(diethylamino)ethoxy]phenyl}-N-piperidin-3-ylthiophene-3-carboxamide;
2-[(aminocarbonyl)amino]-5-(4-methoxyphenyl)-N-[(3S)-piperidin-3-yl]thiophene-3-carboxamide;
tert-butyl 3-{[(2-[(aminocarbonyl)amino]-5-{3-[2-(diethylamino)ethoxy]phenyl}-3-thienyl)carbonyl]amino}piperidine-1-carboxylate;
2-[(aminocarbonyl)amino]-5-{4-[2-(diethylamino)ethoxy]phenyl}-N-piperidin-4-ylthiophene-3-carboxamide;
2-[(aminocarbonyl)amino]-N-[(3R)-azepan-3-yl]-5-(4-methoxyphenyl)thiophene-3-carboxamide;
N-(3-[(4-aminopiperidin-1-yl)carbonyl]-5-{4-[2-(diethylamino)ethoxy]phenyl}-2-thienyl)urea;

2-[(aminocarbonyl)amino]-5-{4-[2-(diethylamino)ethoxy]phenyl}-N-[3-(hydroxymethyl)phenyl]thiophene-3-carboxamide;

2-[(aminocarbonyl)amino]-5-{3-[2-(diethylamino)ethoxy]phenyl}-N-piperidinylthiophene-3-carboxamide;

2-[(aminocarbonyl)amino]-N-(2-aminoethyl)-5-(4-methoxyphenyl)thiophene-3-carboxamide;

2-[(aminocarbonyl)amino]-5-(4-methoxyphenyl)-N-piperidin-4-ylthiophene-3-carboxamide;

2-[(aminocarbonyl)amino]-5-{3-[2-(diethylamino)ethoxy]phenyl}-N-pyridin-3-ylthiophene-3-carboxamide;

2-[(aminocarbonyl)amino]-5-(4-methoxyphenyl)-N-(1-methylpiperidinyl)thiophene-3-carboxamide;

2-[(aminocarbonyl)amino]-5-(4-methoxyphenyl)-N-[(3S)-1-methylazepan-3-yl]thiophene-3-carboxamide;

2-[(aminocarbonyl)amino]-5-{3-[2-(diethylamino)ethoxy]phenyl}-N-[3-(hydroxymethyl)phenyl]thiophene-3-carboxamide;

2-[(aminocarbonyl)amino]-5-{4-[2-(diethylamino)ethoxy]phenyl}-N-pyrrolidin-3-ylthiophene-3-carboxamide;

2-[(aminocarbonyl)amino]-5-{4-[2-(diethylamino)ethoxy]phenyl}-N-pyridin-3-ylthiophene-3-carboxamide;

2-[(aminocarbonyl)amino]-5-(4-methoxyphenyl)-N-[(3S)-1-methylpiperidin-3-yl]thiophene-3-carboxamide;

2-[(aminocarbonyl)amino]-5-{3-[2-(diethylamino)ethoxy]phenyl}-N-pyrrolidin-3-ylthiophene-3-carboxamide;

2-[(aminocarbonyl)amino]-5-(4-methoxyphenyl)-N-[(3R)-piperidin-3-ylmethyl]thiophene-3-carboxamide;

2-[(aminocarbonyl)amino]-5-(4-methoxyphenyl)-N-[(3S)-pyrrolidin-3-yl]thiophene-3-carboxamide;

2-[(aminocarbonyl)amino]-5-(4-methoxyphenyl)-N-[(3R)-pyrrolidin-3-yl]thiophene-3-carboxamide;

2-[(aminocarbonyl)amino]-N-[2-(dimethylamino)ethyl]-5-(4-methoxyphenyl)thiophene-3-carboxamide;

2-[(aminocarbonyl)amino]-N-[2-(diethylamino)ethyl]-5-(4-methoxyphenyl)thiophene-3-carboxamide;

2-[(aminocarbonyl)amino]-N-[(3S)-azepan-3-yl]-5-(4-methoxyphenyl)thiophene-3-carboxamide;

2-[(aminocarbonyl)amino]-5-(4-methoxyphenyl)-N-[(3R)-piperidin-3-yl]thiophene-3-carboxamide;

2-[(aminocarbonyl)amino]-5-(4-methoxyphenyl)-N-(piperidin-4-ylmethyl)thiophene-3-carboxamide;

2-[(aminocarbonyl)amino]-5-(4-methoxyphenyl)-N-pyrrolidin-3-ylthiophene-3-carboxamide;

2-[(aminocarbonyl)amino]-N-(1-ethylpiperidin-3-yl)-5-(4-methoxyphenyl)thiophene-3-carboxamide;

2-[(aminocarbonyl)amino]-N-[(3S)-1-ethylazepan-3-yl]-5-(4-methoxyphenyl)thiophene-3-carboxamide;

2-[(aminocarbonyl)amino]-5-(3-hydroxyphenyl)-N-piperidin-4-ylthiophene-3-carboxamide;

2-[(aminocarbonyl)amino]-5-(4-hydroxyphenyl)-N-piperidin-4-ylthiophene-3-carboxamide;

2-[(aminocarbonyl)amino]-5-(3-methoxyphenyl)-N-piperidin-4-ylthiophene-3-carboxamide;

tert-butyl(3S)-3-({[2-[(aminocarbonyl)amino]-5-(4-methoxyphenyl)-3-thienyl]carbonyl}amino)pyrrolidine-1-carboxylate;

2-[(aminocarbonyl)amino]-5-(4-methoxyphenyl)-N-piperidin-3-ylthiophene-3-carboxamide;

2-[(aminocarbonyl)amino]-N-(1-benzylpiperidin-4-yl)-5-(4-methoxyphenyl)thiophene-3-carboxamide;

tert-butyl 3-({[2-[(aminocarbonyl)amino]-5-(4-methoxyphenyl)-3-thienyl]carbonyl}amino)piperidine-1-carboxylate;

2-[(aminocarbonyl)amino]-5-[4-(2-piperidin-1-ylethoxy)phenyl]-N-(2-pyridin-4-ylethyl)thiophene-3-carboxamide;

2-[(aminocarbonyl)amino]-5-[4-(2-piperidin-1-ylethoxy)phenyl]-N-(2-pyridin-4-ylethyl)thiophene-3-carboxamide;

2-[(aminocarbonyl)amino]-N-azetidin-3-yl-5-(4-methoxyphenyl)thiophene-3-carboxamide;

2-[(aminocarbonyl)amino]-5-(4-methoxyphenyl)-N-[(2S)-pyrrolidin-2-ylmethyl]thiophene-3-carboxamide;

2-[(aminocarbonyl)amino]-5-(4-methoxyphenyl)-N-pyridin-4-ylthiophene-3-carboxamide;

2-[(aminocarbonyl)amino]-5-(4-methoxyphenyl)-N-(2-piperazin-1-ylethyl)thiophene-3-carboxamide;

2-[(aminocarbonyl)amino]-5-(4-methoxyphenyl)-N-(2-piperidin-1-ylethyl)thiophene-3-carboxamide;

2-[(aminocarbonyl)amino]-N-1-azabicyclo[2.2.2]oct-3-yl-5-(4-methoxyphenyl)thiophene-3-carboxamide;

2-[(aminocarbonyl)amino]-N-(2-hydroxyethyl)-5-(4-hydroxyphenyl)thiophene-3-carboxamide;

2-[(aminocarbonyl)amino]-N-(trans-4-hydroxycyclohexyl)-5-(4-methoxyphenyl)thiophene-3-carboxamide;

2-[(aminocarbonyl)amino]-5-(4-hydroxyphenyl)-N-(2-pyridin-4-ylethyl)thiophene-3-carboxamide;

2-[(aminocarbonyl)amino]-5-(4-methoxyphenyl)-N-(2-piperazin-1-ylethyl)thiophene-3-carboxamide;

2-[(aminocarbonyl)amino]-5-(4-methoxyphenyl)-N-(2-pyridin-4-ylethyl)thiophene-3-carboxamide;

2-[(aminocarbonyl)amino]-5-(4-hydroxyphenyl)-N-(2-pyridin-3-ylethyl)thiophene-3-carboxamide;

2-[(aminocarbonyl)amino]-5-(4-methoxyphenyl)-N-(2-pyridin-3-ylethyl)thiophene-3-carboxamide;

2-[(aminocarbonyl)amino]-5-(4-methoxyphenyl)-N-(2,2,6,6-tetramethylpiperidin-4-yl)thiophene-3-carboxamide;

2-[(aminocarbonyl)amino]-5-(2-methoxyphenyl)-N-piperidinylthiophene-3-carboxamide;

2-[(aminocarbonyl)amino]-5-(4-methoxyphenyl)-N-(tetrahydrofuran-2-ylmethyl)thiophene-3-carboxamide;

tert-butyl(3R)-3-({[2-[(aminocarbonyl)amino]-5-(4-methoxyphenyl)-3-thienyl]carbonyl}amino)piperidine-1-carboxylate;

2-[(aminocarbonyl)amino]-5-(4-methoxyphenyl)-N-(pyridin-3-ylmethyl)thiophene-3-carboxamide;

tert-butyl 3-({[2-[(aminocarbonyl)amino]-5-(4-methoxyphenyl)-3-thienyl]carbonyl}amino)azetidine-1-carboxylate;

2-[(aminocarbonyl)amino]-5-(4-methoxyphenyl)-N-(pyridin-4-ylmethyl)thiophene-3-carboxamide;

2-[(aminocarbonyl)amino]-5-(4-methoxyphenyl)-N-(3-methoxypropyl)thiophene-3-carboxamide;

2-[(aminocarbonyl)amino]-5-(4-methoxyphenyl)-N-[2-(2-thienyl)ethyl]thiophene-3-carboxamide;

2-[(aminocarbonyl)amino]-5-(4-methoxyphenyl)-N-(2-thienylmethyl)thiophene-3-carboxamide;

N-[3-(1,4-diazepan-1-ylcarbonyl)-5-(4-methoxyphenyl)-2-thienyl]urea;

2-[(aminocarbonyl)amino]-N-(2-methoxyethyl)-5-(4-methoxyphenyl)thiophene-3-carboxamide;

2-[(aminocarbonyl)amino]-5-(4-hydroxyphenyl)-N-(2-thienylmethyl)thiophene-3-carboxamide;

2-[(aminocarbonyl)amino]-N-{2-[(2-furylmethyl)thio]ethyl}-5-(4-methoxyphenyl)thiophene-3-carboxamide;

2-[(aminocarbonyl)amino]-5-(4-hydroxyphenyl)-N-[2-(2-thienyl)ethyl]thiophene-3-carboxamide;

N-(3-[(4-aminopiperidin-1-yl)carbonyl]-5-{3-[2-(diethylamino)ethoxy]phenyl}-2-thienyl)urea;

2-[(aminocarbonyl)amino]-5-(4-methoxyphenyl)-N-[(3R)-piperidin-3-ylmethyl]thiophene-3-carboxamide;

2-[(aminocarbonyl)amino]-5-(4-methoxyphenyl)-N-(1,2,3,4-tetrahydroquinolin-3-yl)thiophene-3-carboxamide;

2-[(aminocarbonyl)amino]-N-(1,3-benzodioxol-5-ylmethyl)-5-(4-methoxyphenyl)thiophene-3-carboxamide;

2-[(aminocarbonyl)amino]-N-(3-methoxybenzyl)-5-(4-methoxyphenyl)thiophene-3-carboxamide;

2-[(aminocarbonyl)amino]-N-[2-(3,4-dimethoxyphenyl)ethyl]-5-(4-methoxyphenyl)thiophene-3-carboxamide;

2-[(aminocarbonyl)amino]-5-(4-methoxyphenyl)-N-[(5-methyl-2-furyl)methyl]thiophene-3-carboxamide;

2-[(aminocarbonyl)amino]-5-(4-methoxyphenyl)-N-(pyridin-2-ylmethyl)thiophene-3-carboxamide;

2-[(aminocarbonyl)amino]-N-(4-fluorobenzyl)-5-(4-methoxyphenyl)thiophene-3-carboxamide;

tert-butyl 4-({[2-[(aminocarbonyl)amino]-5-(3-methoxyphenyl)-3-thienyl]carbonyl}amino)piperidine-1-carboxylate;

2-[(aminocarbonyl)amino]-N-(2-methoxybenzyl)-5-(4-methoxyphenyl)thiophene-3-carboxamide;

2-[(aminocarbonyl)amino]-5-(4-methoxyphenyl)-N-(2-phenoxyethyl)thiophene-3-carboxamide;

2-[(aminocarbonyl)amino]-5-(4-methoxyphenyl)-N-(2-pyridin-2-ylethyl)thiophene-3-carboxamide;

tert-butyl 4-({[2-[(aminocarbonyl)amino]-5-(4-methoxyphenyl)-3-thienyl]carbonyl}amino)piperidine-1-carboxylate;

2-[(aminocarbonyl)amino]-N-(4-methoxybenzyl)-5-(4-methoxyphenyl)thiophene-3-carboxamide;

2-[(aminocarbonyl)amino]-5-{4-[2-(diethylamino)ethoxy]phenyl}-N-[(3S)-piperidin-3-yl]thiophene-3-carboxamide;

2-[(aminocarbonyl)amino]-5-{4-[2-(diethylamino)ethoxy]phenyl}-N-[(3R)-piperidin-3-yl]thiophene-3-carboxamide;

tert-butyl(3S)-3-{[(2-[(aminocarbonyl)amino]-5-{4-[2-(diethylamino)ethoxy]phenyl}-3-thienyl)carbonyl]amino}piperidine-1-carboxylate;

2-[(aminocarbonyl)amino]-N-[(3S)-azepan-3-yl]-5-{4-[2-(diethylamino)ethoxy]phenyl}thiophene-3-carboxamide;

tert-butyl(3R)-3-{[(2-[(aminocarbonyl)amino]-5-{4-[2-(diethylamino)ethoxy]phenyl}-3-thienyl)carbonyl]amino}piperidine-1-carboxylate;

N-[3-{[(3S)-3-aminoazepan-1-yl]carbonyl}-5-(4-methoxyphenyl)-2-thienyl]urea;

5-{4-[2-(diethylamino)ethoxy]phenyl}-2-{[(pyrazin-2-ylamino)carbonyl]amino}-N-[(3S)-pyrrolidin-3-yl]thiophene-3-carboxamide;

5-{3-[2-(diethylamino)ethoxy]phenyl}-2-{[(pyrazin-2-ylamino)carbonyl]amino}-N-[(3S)-pyrrolidin-3-yl]thiophene-3-carboxamide;

5-{3-[2-(diethylamino)ethoxy]phenyl}-N-piperidin-4-yl-2-{([(pyrazin-2-ylamino)carbonyl]amino}thiophene-3-carboxamide;

N-[(3S)-azepan-3-yl]-5-(4-methoxyphenyl)-2-{[(pyrazin-2-ylamino)carbonyl]amino}thiophene-3-carboxamide;

5-{3-[2-(diethylamino)ethoxy]phenyl}-N-piperidin-3-yl-2-{[(pyrazin-2-ylamino)carbonyl]amino}thiophene-3-carboxamide;

N-(2-aminoethyl)-5-(4-methoxyphenyl)-2-{[(pyrazin-2-ylamino)carbonyl]amino)}thiophene-3-carboxamide;

5-{4-[2-(diethylamino)ethoxy]phenyl}-N-piperidin-3-yl-2-{[(pyrazin-2-ylamino)carbonyl]amino}thiophene-3-carboxamide;

5-(4-methoxyphenyl)-N-piperidin-4-yl-2-{[(pyrazin-2-ylamino)carbonyl]amino}thiophene-3-carboxamide;

tert-butyl 3-{[(5-{3-[2-(diethylamino)ethoxy]phenyl}-2-{[(pyrazin-2-ylamino)carbonyl]amino}-3-thienyl)carbonyl]amino}piperidine-1-carboxylate;

5-{4-[2-(diethylamino)ethoxy]phenyl}-N-piperidin-4-yl-2-{[(pyrazin-2-ylamino)carbonyl]amino}thiophene-3-carboxamide;

5-(4-methoxyphenyl)-2-{[(pyrazin-2-ylamino)carbonyl]amino}-N-[(3S)-pyrrolidin-3-yl]thiophene-3-carboxamide;

N-[3-(1,4-diazepan-1-ylcarbonyl)-5-(4-methoxyphenyl)-2-thienyl]-N'-pyrazin-2-ylurea;

N-[3-[(3-aminopyrrolidin-1-yl)carbonyl]-5-(4-methoxyphenyl)-2-thienyl]-N'-pyrazin-2-ylurea;

tert-butyl 4-{[(5-(4-methoxyphenyl)-2-{[(pyrazin-2-ylamino)carbonyl]amino}-3-thienyl)carbonyl]amino}piperidine-1-carboxylate;

tert-butyl 3-{[(5-{4-[2-(diethylamino)ethoxy]phenyl}-2-{[(pyrazin-2-ylamino)carbonyl]amino}-3-thienyl)carbonyl]amino}piperidine-1-carboxylate;

5-[4-(2-diethylamino-ethoxy)-phenyl]-2-(3-hydroxy-urea)-thiophene-3-carboxylic acid-(S)-piperidin-3-ylamide;

2-[(aminocarbonyl)amino]-N-[(3S)-azepan-3-yl]-5-(3-methoxyphenyl)thiophene-3-carboxamide;

2-[(aminocarbonyl)amino]-5-(2-hydroxyphenyl)-N-[(3S)-piperidin-3-yl]thiophene-3-carboxamide;

2-[(aminocarbonyl)amino]-5-(3-methoxyphenyl)-N-[(3S)-piperidin-3-yl]thiophene-3-carboxamide;

2-[(aminocarbonyl)amino]-5-[2-(benzyloxy)phenyl]-N-[(3S)-piperidin-3-yl]thiophene-3-carboxamide.

One embodiment of the present invention provides compounds of formula (I) or a pharmaceutically acceptable salt thereof for use as a medicament.

One embodiment of the present invention provides compounds of formula (I) or a pharmaceutically acceptable salt thereof in the manufacture of a medicament for the treatment or prophylaxis of disorders associated with cancer.

One embodiment of the present invention provides a method for the treatment of cancer comprising administering to a human a therapeutically effective amount of a compound of formula (I) or a pharmaceutically acceptable salt thereof.

One embodiment of the present invention provides a method for the treatment of breast cancer, colorectal cancer, ovarian cancer, lung (non small cell) cancer, malignant brain tumors, sarcomas, melanoma and lymphoma by administering a compound of formula I or a pharmaceutically acceptable salt thereof.

One embodiment the of present invention provides a method of treating cancer by administering to a human a compound of formula (I) or a pharmaceutically acceptable salt thereof and an anti-tumor agent.

One embodiment of the present invention provides a method of treating cancer by administering to a human a compound of formula (I) or a pharmaceutically acceptable salt thereof and a DNA damaging agent.

One embodiment of the present invention provides a method for the treatment of infections associated with cancer comprising administering to a host in need of such treatment a therapeutically effective amount of a compound of formula (I) or a pharmaceutically acceptable salt thereof.

One embodiment of the present invention provides a method for the prophylaxis treatment of infections associated with cancer comprising administering to a host in need of such treatment a therapeutically effective amount of a compound of formula (I) or a pharmaceutically acceptable salt thereof.

One embodiment of the present invention provides a pharmaceutical composition comprising a compound of formula (I) or a pharmaceutically acceptable salt thereof together with at least one pharmaceutically acceptable carrier, diluent or excipent.

One embodiment of the present invention provides a process for the preparation of a compound of formula (I) or a pharmaceutically acceptable salt thereof, which comprises:

(a) the reaction of a 2-aminothiophene shown below as formula II

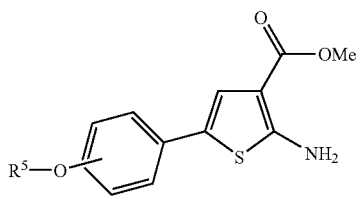

II wherein the hydrogen at the 2-amino position is displaced to form an amide, shown as formula III below

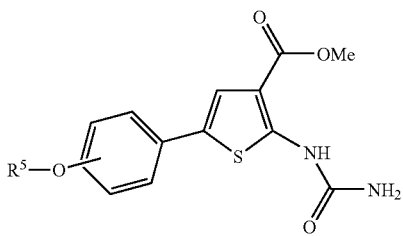

III wherein the methyl ester is converted to an amide utilizing the desired amine in conjunction with an aluminate organometallic complex, to give the product shown as formula IV below:

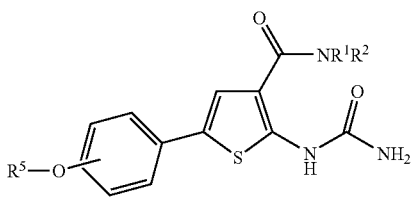

IV wherein the amide is converted to various substituted secondary ureas by the reaction with various isocyanantes to yield the product shown as formula V below:

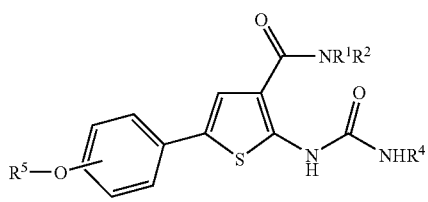

V

One embodiment of the present invention provides the use of a compound of formula (VI) below or a pharmaceutically acceptabl salt or an in vivo hydrolysable precursor in the manufacture of a compound of formula (I).

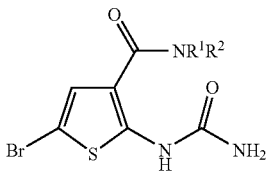

VI

The definitions set forth in this application are intended to clarify terms used throughout this application. The term "herein" means the entire application.

As used in this application, the term "optionally substituted," as used herein, means that substitution is optional and therefore it is possible for the designated atom to be unsubstituted. In the event a substitution is desired then such substitution means that any number of hydrogens on the designated atom is replaced with a selection from the indicated group, provided that the normal valency of the designated atom is not exceeded, and that the substitution results in a stable compound. For example when a substituent is keto (i.e., =O), then 2 hydrogens on the atom are replaced. Examples of such substituents are as follows:

halogen, nitro, amino, cyano, trifluoromethyl, $C_{1-6}$alkyl, alkenyl, alkynyl, haloalkyl, alkoxy, hydroxy, alkylhydroxy, carbonyl, —CH(OH)CH$_3$, —CH$_2$NH-alkyl-OH, alkyl-(OH)CH$_3$, —CH$_2$-phenyl-(OCH$_3$)$_2$, —Oalkyl, —OCH$_3$, —Ophenyl, —OCOalkyl, —NHCHO, —N-(alkyl)-CHO, —Nalkyl, —NH—CO-amino, —N-(alkyl)-CO-amino, —NH—COalkyl, —N-(alkyl)-COalkyl, -carboxy, -amidino, —CO-amino, —CO-alkyl, —CO$_2$alkyl, mercapto, —Salkyl, —SCH$_2$furanyl, —SO(alkyl), —SO$_2$(alkyl), —SO$_2$-amino, -alkylsulfonylamino, phenyl, anisole, dimethoxyphenyl, trimethoxyphenyl, halophenyl, cycloalkyl, heterocyclyl, -alkyl-NH-cycloalkyl, -alkyl-NH-heterocyclyl, -alkyl-NH-alkyl-OH, —C(=O)OC(CH$_3$)$_3$, —N(CH$_3$)$_2$, —N(CH$_2$CH$_3$)$_2$, -alkyl-NH-alkyl-heterocyclyl, -alkyl-aryl, -methyl-phenyl, alkyl-polycyclyl, alkyl-amino, alkyl-hydroxy, —CH$_2$NH-alkyl-heterocyclyl, —CH$_2$NHCH2CH(CH$_3$)$_2$.

If the selection is attached to a ring the substituents could also be selected from: vicinal —O(alkyl)O—, vicinal —OC(haloalkyl)O—, vicinal —CH$_2$O(alkyl)O—, vicinal —S(alkyl)S— and —O(alkyl)S—.

A variety of compounds in the present invention may exist in particular geometric or stereoisomeric forms. The present invention takes into account all such compounds, including cis- and trans isomers, R- and S-enantiomers, diastereomers, (D)-isomers, (L)-isomers, the racemic mixtures thereof, and other mixtures thereof, as being covered within the scope of this invention. Additional asymmetric carbon atoms may be present in a substituent such as an alkyl group. All such isomers, as well as mixtures thereof, are intended to be included in this invention. The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. When required, separation of the racemic material can be achieved by methods known in the art. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" used alone or as a suffix or prefix, is intended to include both branched and straight-chain saturated aliphatic hydrocarbon groups having from 1 to 12 carbon atoms or if a specified number of carbon atoms is provided then that specific number would be intended. For example "$C_{1-6}$alkyl" denotes alkyl having 1, 2, 3, 4, 5 or 6 carbon atoms. Examples of alkyl include, but are not limited to, methyl, ethyl, n-propyl, i-propyl, n-butyl, i-butyl, sec-butyl, t-butyl, pentyl, and hexyl. As used herein, "$C_{1-3}$ alkyl", whether a terminal substituent or an alkylene group linking two substituents, is understood to specifically include both branched and straight-chain methyl, ethyl, and propyl.

As used herein "alkylhydroxy" represents an alkyl group straight chain or branched as defined above with the indicated number of carbon atoms with one or more hydroxy groups attached. One such example of alkylhydroxy would be —$CH_2OH$.

As used herein, the term "carbocyclyl" is intended to include both alicyclic and aromatic ring structures wherein the closed ring is made of carbon atoms. These may include fused or bridged polycyclic systems. Carbocyclyls may have from 3 to 10 carbon atoms in their ring structure, and often have 3, 4, 5, and 6 carbons in the ring structure. For example, "$C_{3-6}$ carbocyclyl" denotes such groups as cyclopropyl, cyclobutyl, cyclopentyl, cyclohexyl, cyclopenta-diene or phenyl.

As used herein, the term "cycloalkyl" is intended to include saturated ring groups, having the specified number of carbon atoms. These may include fused or bridged polycyclic systems. Preferred cycloalkyls have from 3 to 10 carbon atoms in their ring structure, and more preferably have 3, 4, 5, and 6 carbons in the ring structure. For example, "$C_{3-6}$ cycloalkyl" denotes such groups as cyclopropyl, cyclobutyl, cyclopentyl, or cyclohexyl.

As used herein, "alkenyl" or "alkenylene" is intended to include from 2 to 12 hydrocarbon atoms of either a straight or branched configuration with one or more carbon-carbon double bonds that may occur at any stable point along the chain. Examples of "$C_{3-6}$alkenyl" include, but are not limited to, 1-propenyl, 2-propenyl, 1-butenyl, 2-butenyl, 3-butenyl, 3-methyl-2-butenyl, 2-pentenyl, 3-pentenyl, hexenyl.

As used herein, "alkynyl" or "alkynylene" is intended to include from 2 to 12 hydrocarbon chains of either a straight or branched configuration with one or more carbon-carbon triple bonds that may occur at any stable point along the chain. Examples of alkynyl include but are not limited to ethynyl, 1-propynyl, 2-propynyl, 1-butynyl, 2-butynyl, 3-butynyl.

As used herein, the term "alkylcycloalkyl" is intended to mean an alkyl attached to the formula atom modified with a cycloalkyl. Examples of alkylcycloalkyl include, but are not limited to cyclopropylmethyl, cyclopentylmethyl, cyclohexylmethyl, cycloheptylmethyl, cyclopropylethyl, cyclopentylethyl, cyclohexylethyl, cycloheptylethyl, cyclopropylpropyl, cyclopentylpropyl, cyclohexylpropyl, cycloheptylpropyl.

As used herein, "cycloalkenyl" refers to ring-containing hydrocarbyl groups having at least one carbon-carbon double bond in the ring, and having from 3 to 12 carbons atoms.

As used herein, "cycloalkynyl" refers to ring-containing hydrocarbyl groups having at least one carbon-carbon triple bond in the ring, and having from 7 to 12 carbons atoms.

As used herein, the term "aralkyl" refers to an alkyl group substituted with an aryl group (an aromatic or heteroaromatic group).

As used herein, "aromatic" refers to hydrocarbyl groups having one or more polyunsaturated carbon rings having aromatic character, (e.g., 4n+2 delocalized electrons) and comprising up to about 14 carbon atoms.

The term "aryl" as used herein includes 5-, 6- and 7-membered single-ring aromatic groups that may include from zero to four heteroatoms, for example, benzene, furan, imidazole, isoxazole, nicotinic, isonictinic, oxazole, phenyl, pyrazole, pyrazine, pyridazine, pyridine, pyrimidine, thiazole, thiophene, triazole and the like. Those aryl groups having heteroatoms in the ring structure may also be referred to as "heteroaryl" or "heteroaromatics." The aromatic ring can be substituted at one or more ring positions with such substituents as described above. The term "aryl" also includes polycyclic ring systems having two or more cyclic rings in which two or more carbons are common to two adjoining rings (the rings are "fused rings") wherein at least one of the rings is aromatic, for example, the other cyclic rings can be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

As used herein, the term "heterocyclyl" or "heterocyclic" or "heterocycle" refers to a ring-containing monovalent and divalent structures having one or more heteroatoms, independently selected from N, O and S, as part of the ring structure and comprising from 3 to 20 atoms in the rings, more preferably 3- to 7-membered rings. Heterocyclic groups may be saturated or unsaturated, containing one or more double bonds, and heterocyclic groups may contain more than one ring as in the case of polycyclic systems. The heterocyclic rings described herein may be substituted on carbon or on a heteroatom atom if the resulting compound is stable. If specifically noted, nitrogen in the heterocyclyl may optionally be quaternized. It is understood that when the total number of S and O atoms in the heterocyclyl exceeds 1, then these heteroatoms are not adjacent to one another.

Examples of heterocyclyls include, but are not limited to, 1H-indazole, 2-pyrrolidonyl, 2H, 6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azabicyclo, azetidine, azepane, aziridine, azocinyl, benzimidazolyl, benzodioxol, benzofuranyl, benzothiofuranyl, benzothiophenyl, benzoxazolyl, benzthiazolyl, benzotriazolyl, benzotetrazolyl, benzisoxazolyl, benzisothiazolyl, benzimidazalonyl, carbazolyl, 4aH-carbazolyl, b-carbolinyl, chromanyl, chromenyl, cinnolinyl, diazepane, decahydroquinolinyl, 2H,6H-1,5,2-dithiazinyl, dioxolane, furyl, 2,3-dihydrofuran, 2,5-dihydrofuran, dihydrofuro[2,3-b]tetrahydrofuran, furanyl, furazanyl, homopiperidinyl, imidazolidine, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxirane, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, purinyl, pyranyl, pyrrolidinyl, pyrroline, pyrrolidine, pyrazinyl, pyrazolidinyl, pyrazolinyl, pyrazolyl, pyridazinyl, pyridooxazole, pyridoimidazole, pyridothiazole, pyridinyl, N-oxide-pyridinyl, pyridyl, pyrimidinyl, pyrrolidinyl, pyrrolinyl, pyrrolyl, pyridine, quinazolinyl, quinolinyl, 4H-quinolizinyl, quinoxalinyl, quinuclidinyl, carbolinyl, tetrahydrofuranyl, tetrahydroquinoline, tetrahydroisoquinolinyl, thiophane, thiotetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiopheneyl, thiirane, triazinyl, 1,2,3-triazolyl, 1,2,4-triazolyl, 1,2,5-triazolyl, 1,3,4-triazolyl, xanthenyl.

The terms "polycyclyl" or "polycyclic group" refer to two or more rings (for example, cycloalkyls, cycloalkenyls, cycloalkynyls, aryls and/or heterocyclyls) in which two or more carbons are common to two adjoining rings, for example, the rings are "fused rings." Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, carbonyl, carboxyl, ether, alkylthio, sulfonyl, ketone, aldehyde, ester, a heterocyclyl, an aromatic or heteroaromatic moiety, —CF$_3$, —CN, or the like. Examples of such bridged heterocyclyls include quinuclidine, diazabicyclo[2.2.1]heptane and 7-oxabicyclo[2.2.1]heptane, substituted piperazine.

As used herein, the term "amine" or "amino" refers to groups of the general formula —NRR', wherein R and R' are each independently represented by but not limited to hydrogen, alkyl, cycloalkyl, alkenyl, aryl, heteroaryl, aralkyl, or heteroaralkyl. Example of the amino group include, but are not limited to NH$_2$, methylamine, ethylamine, dimethylamine, diethylamine, propylamine, benzylamine and the like.

As used herein, the term "amido" is art-recognized as an amino-substituted carbonyl and includes a moiety that can be represented by the general formula:

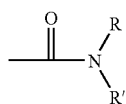

wherein R and R' are each independently represented by but not limited to hydrogen, alkyl, cycloalkyl, alkenyl, aryl, heteroaryl, heterocyclyl, aralkyl, or heteroaralkyl, or R and R' may form a ring.

As used herein, "alkoxy" or "alkyloxy" represents an alkyl group as defined above with the indicated number of carbon atoms attached through an oxygen bridge. Examples of alkoxy include, but are not limited to, methoxy, ethoxy, n-propoxy, isopropoxy, n-butoxy, isobutoxy, t-butoxy, n-pentoxy, isopentoxy, cyclopropylmethoxy, allyloxy and propargyloxy. Similarly, "alkylthio" or "thioalkoxy" represent an alkyl group as defined above with the indicated number of carbon atoms attached through a sulphur bridge.

As used herein, the term "acyl" refers to groups of the of the general formula —C(=O)—R, wherein R is hydrogen, hydrocarbyl radical. Examples of acyl groups include, but are not limited to acetyl, propionyl, benzoyl, phenyl acetyl.

As used herein, the term "carbonyl" is art recognized and includes such moieties as can be represented by the general formula:

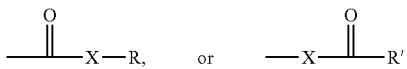

wherein X is a bond or represents an oxygen or sulfur, and R represents a hydrogen, an alkyl, an alkenyl, —(CH$_2$)$_m$—R" or a pharmaceutically acceptable salt, R' represents a hydrogen, an alkyl, an alkenyl or —(CH$_2$)$_m$—R", where m is an integer less than or equal to ten, and R" is alkyl, cycloalkyl, alkenyl, aryl, or heteroaryl. Where X is an oxygen and R and R' is not hydrogen, the formula represents an "ester". Where X is an oxygen, and R is as defined above, the moiety is referred to herein as a carboxyl group, and particularly when R' is a hydrogen, the formula represents a "carboxylic acid." Where X is oxygen, and R' is a hydrogen, the formula represents a "formate." In general, where the oxygen atom of the above formula is replaced by sulfur, the formula represents a "thiolcarbonyl" group. Where X is a sulfur and R and R' is not hydrogen, the formula represents a "thiolester." Where X is sulfur and R is hydrogen, the formula represents a "thiolcarboxylic acid." Where X is sulfur and R' is hydrogen, the formula represents a "thiolformate." On the other hand, where X is a bond, and R is not a hydrogen, the above formula represents a "ketone" group. Where X is a bond, and R is hydrogen, the above formula is represents an "aldehyde" group.

As used herein, the term "sulfonylamino" is art-recognized and refers to a moiety that can be represented by the general formula:

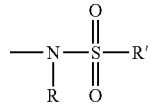

wherein R and R' are each independently represented by but not limited to hydrogen, alkyl, cycloalkyl, alkenyl, aryl, heteroaryl, heterocyclyl, aralkyl, or heteroaralkyl.

As used herein, the term "sulfonyl" is art-recognized and refers to a moiety that can be represented by the general formula:

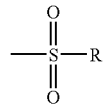

wherein R is represented by but not limited to hydrogen, alkyl, cycloalkyl, alkenyl, aryl, heteroaryl, aralkyl, or heteroaralkyl.

As used herein, "halo" or "halogen" refers to fluoro, chloro, bromo, and iodo. "Counterion" is used to represent a small, negatively charged species such as chloride, bromide, hydroxide, acetate, sulfate, tosylate, benezensulfonate, and the like.

As used herein, "haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, pentachloroethyl, 2,2,2-trifluoroethyl, 2,2-difluoroethyl, heptafluoropropyl, and heptachloropropyl. "Haloalkoxy" is intended to mean a haloalkyl group as defined above with the indicated number of carbon atoms attached through an oxygen bridge; for example trifluoromethoxy, pentafluoroethoxy, 2,2,2-trifluoroethoxy, and the like. "Haloalkylthio" is intended to mean a haloalkyl group as defined above with the indicated number of carbon atoms attached through a sulphur bridge.

As used herein, the phrase-protecting protecting group" means temporary substituents which protect a potentially reactive functional group from undesired chemical transformations. Examples of such protecting groups include esters of carboxylic acids, silyl ethers of alcohols, and acetals and ketals of aldehydes and ketones respectively. The field of protecting group chemistry has been reviewed (Greene, T. W.; Wuts, P. G. M. *Protective Groups in Organic Synthesis*, $3^{rd}$ ed.; Wiley: New York, 1999).

As used herein, "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, phosphoric, and the like; and the salts prepared from organic acids such as lactic, maleic, citric, benzoic, methanesulfonic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are used.

As used herein, "in vivo hydrolysable ester" means an in vivo hydroysable (or cleavable) ester of a compound of the formula (I) that contains a carboxy or a hydroxy group. For example amino acid esters, $C_{1-6}$ alkoxymethyl esters like methoxymethyl; $C_{1-6}$alkanoyloxymethyl esters like pivaloyloxymethyl; $C_{3-8}$cycloalkoxycarbonyloxy $C_{1-6}$alkyl esters like 1-cyclohexylcarbonyloxyethyl, acetoxymethoxy, or phosphoramidic cyclic esters.

As used herein "stable compound" and "stable structure" are meant to indicate a compound that is sufficiently robust to survive isolation to a useful degree of purity from a reaction mixture, and formulation into an efficacious therapeutic agent.

The anticancer treatment defined herein may be applied as a sole therapy or may involve, in addition to the compound of the invention, conventional surgery or radiotherapy or chemotherapy. Such chemotherapy may include one or more of the following categories of anti-tumor agents:

(i) antiproliferative/antineoplastic/DNA damaging drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside, hydroxyurea and gemcitabine); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); topoisomerase inhibitors (for example epipodophyllotoxins like etoposide and teniposide, amsacrine, topotecan, irinotecan and camptothecin) and cytodifferentiating agents (for example All-trans retinoic acid, 13-cis retinoic acid and fenretinide);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy) quinazolin-4-amine (CI 1033)), for example inhibitors of the platelet-derived growth factor family and for example inhibitors of the hepatocyte growth factor family;

(v) antiangiogenic agents such as those which inhibit the effects of vascular endothelial growth factor, (for example the anti-vascular endothelial cell growth factor antibody bevacizumab [Avastin™], compounds such as those disclosed in published International Patent Applications WO 97/22596, WO 97/30035, WO 97/32856 and WO 98/13354) and compounds that work by other mechanisms (for example linomide, inhibitors of integrin αvβ3 function and angiostatin);

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

Such conjoint treatment may be achieved by way of the simultaneous, sequential or separate dosing of the individual components of the treatment. Such combination products employ the compounds of this invention.

Compounds of the present invention may be administered orally, parenteral, buccal, vaginal, rectal, inhalation, insufflation, sublingually, intramuscularly, subcutaneously, topically, intranasally, intraperitoneally, intrathoracially, intravenously, epidurally, intrathecally, intracerebroventricularly and by injection into the joints.

The dosage will depend on the route of administration, the severity of the disease, age and weight of the patient and other factors normally considered by the attending physician, when determining the individual regimen and dosage level as the most appropriate for a particular patient.

An effective amount of a compound of the present invention for use in therapy of infection is an amount sufficient to symptomatically relieve in a warm-blooded animal, particularly a human the symptoms of infection, to slow the progression of infection, or to reduce in patients with symptoms of infection the risk of getting worse.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances, which may also act as diluents, flavoring agents, solubilizers, lubricants, suspending agents, binders, or tablet disintegrating agents; it can also be an encapsulating material.

In powders, the carrier is a finely divided solid, which is in a mixture with the finely divided active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify.

Suitable carriers include magnesium carbonate, magnesium stearate, talc, lactose, sugar, pectin, dextrin, starch, tragacanth, methyl cellulose, sodium carboxymethyl cellulose, a low-melting wax, cocoa butter, and the like.

Some of the compounds of the present invention are capable of forming salts with various inorganic and organic acids and bases and such salts are also within the scope of this invention. For example, such conventional non-toxic salts include those derived from inorganic acids such as hydrochloric, phosphoric, and the like; and the salts prepared from organic acids such as lactic, maleic, citric, benzoic, methanesulfonic, trifluoroacetate and the like.

In one embodiment a compound of the formula (I) or a pharmaceutically acceptable salt thereof for the therapeutic treatment (including prophylactic treatment) of mammals including humans, it is normally formulated in accordance with standard pharmaceutical practice as a pharmaceutical composition.

In addition to the compounds of the present invention, the pharmaceutical composition of this invention may also contain, or be co-administered (simultaneously or sequentially) with, one or more pharmacological agents of value in treating one or more disease conditions referred to herein.

The term composition is intended to include the formulation of the active component or a pharmaceutically acceptable salt with a pharmaceutically acceptable carrier. For example this invention may be formulated by means known in the art into the form of, for example, tablets, capsules, aqueous or oily solutions, suspensions, emulsions, creams, ointments, gels, nasal sprays, suppositories, finely divided powders or aerosols or nebulisers for inhalation, and for parenteral use (including intravenous, intramuscular or infusion) sterile aqueous or oily solutions or suspensions or sterile emulsions.

Liquid form compositions include solutions, suspensions, and emulsions. Sterile water or water-propylene glycol solutions of the active compounds may be mentioned as an example of liquid preparations suitable for parenteral administration. Liquid compositions can also be formulated in solution in aqueous polyethylene glycol solution. Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

The pharmaceutical compositions can be in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms.

Compounds of formula (I) have been shown to inhibit checkpoint kinase activity in vitro. Inhibitors of checkpoint kinase have been shown to allow cells to progress inappropriately to the metaphase of mitosis leading to apoptosis of effected cells, and to therefore have anti-proliferative effects. Therefore it is believed that the compounds of formula (I) may be used for the treatment of neoplastic disease. Hence compounds of formula (I) and their salts are expected to be active against neoplastic disease such as carcinoma of the brain, breast, ovary, lung, colon, prostate, skin or other tissues, as well as leukemias and lymphomas, tumors of the central and peripheral nervous system, and other tumor types such as melanoma, sarcomas, fibrosarcoma and osteosarcoma. In addition, compounds of formula (I) are also expected to be useful for the treatment other proliferative diseases. It is expected that the compounds of formula (I) would most likely be used in combination with a broad range of DNA damaging agents but could also be used as a single agent.

Generally, the compounds of formula (I) have been identified in one or both assays described below as having an $IC_{50}$ value of 100 micromolar or less. For example compound of example 2 has an $IC_{50}$ value of 10 nM.

Checkpoint Kinase 1 Assay: This in vitro assay measures the inhibition of CHK1 kinase by compounds. The kinase domain is expressed in baculovirus and purified by the GST tag. Purified protein and biotinylated peptide substrate (Cdc25C) is then used in a 384 well automated Scintillation Proximity Assay (SPA). Specifically, peptide, enzyme and reaction buffer are mixed and aliquoted into a 384 well plate containing dilution series of compounds and controls. Cold and hot ATP are then added to initiate the reaction. After 2 hours, a SPA bead slurry, CsCl2 and EDTA are added to stop the reaction and capture the biotinylated peptide. Plates are then counted on a Topcount. Data is analyzed and IC50s determined for individual compounds.

Abrogation Assay: This cellular assay measures the ability of CHK1 inhibitors to abrogate the DNA-damage induced G2/M checkpoint. Compounds active against the enzyme (<2 uM) are tested in the cellular assay. Briefly HT29 cells (colon cancer cell line, p53 null) are plated in 96 well plates on day 1. The following day, cells are treated with camptothecin for 2 hours to induce DNA damage. After 2 hours, camptothecin is removed and cells are treated for an additional 18 hours with test compound and nocodazole, a spindle poison that traps in cells in mitosis that abrogate the checkpoint. Cells are then fixed with formaldehyde, stained for the presence of phosphohistone H3, a specific marker for mitosis and labeled with Hoechst dye so that cell number can be measured. Plates are scanned using the Mitotic Index protocol on the Array Scan (Cellomics). As a positive control for abrogation, 4 mM caffeine is used. Compounds are tested in a 12-point dose response in triplicate. Data is analyzed and EC50s determined for individual compounds.

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Such methods include, but are not limited to, those described below. All references cited herein are hereby incorporated in their entirety by reference.

The novel compounds of this invention may be prepared using the reactions and techniques described herein. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents, which are not compatible with the reaction conditions, will be readily apparent to one skilled in the art and alternate methods must then be used.

The starting materials for the examples contained herein are either commercially available or are readily prepared by standard methods from known materials. For example the following reactions are illustrations but not limitations of the preparation of some of the starting materials and examples used herein.

General procedures for making the compounds of the invention is as follows:

The first of these procedures initiates from a common intermediate. This intermediate 2-aminothiophene core is produced by a one-pot Gewald synthesis from reaction of cyanomethylacetate with various benzaldehydes and elemental sulfur under basic conditions shown below in Scheme I.

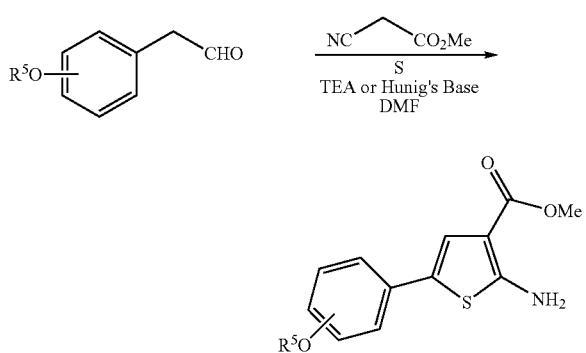

If not commercially available, the corresponding benzaldehydes could be synthesized using some or all of the transformations described in Scheme II.

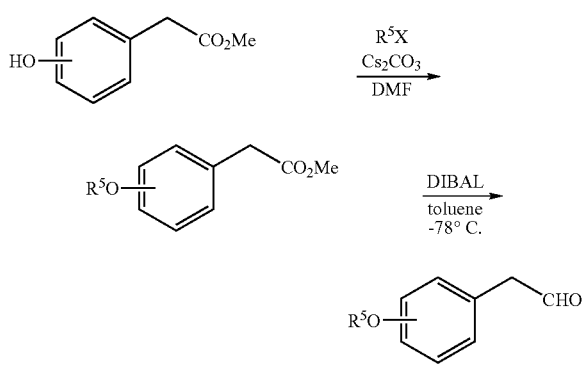

Compounds of Formula (I) can then be synthesized from the general synthetic methods described below in Schemes III-IX. The first general method shown in Scheme III involves a Weinreb amide formation from reaction of either the trichloroacetyl-protected or free urea with an amino aluminate organometallic complex.

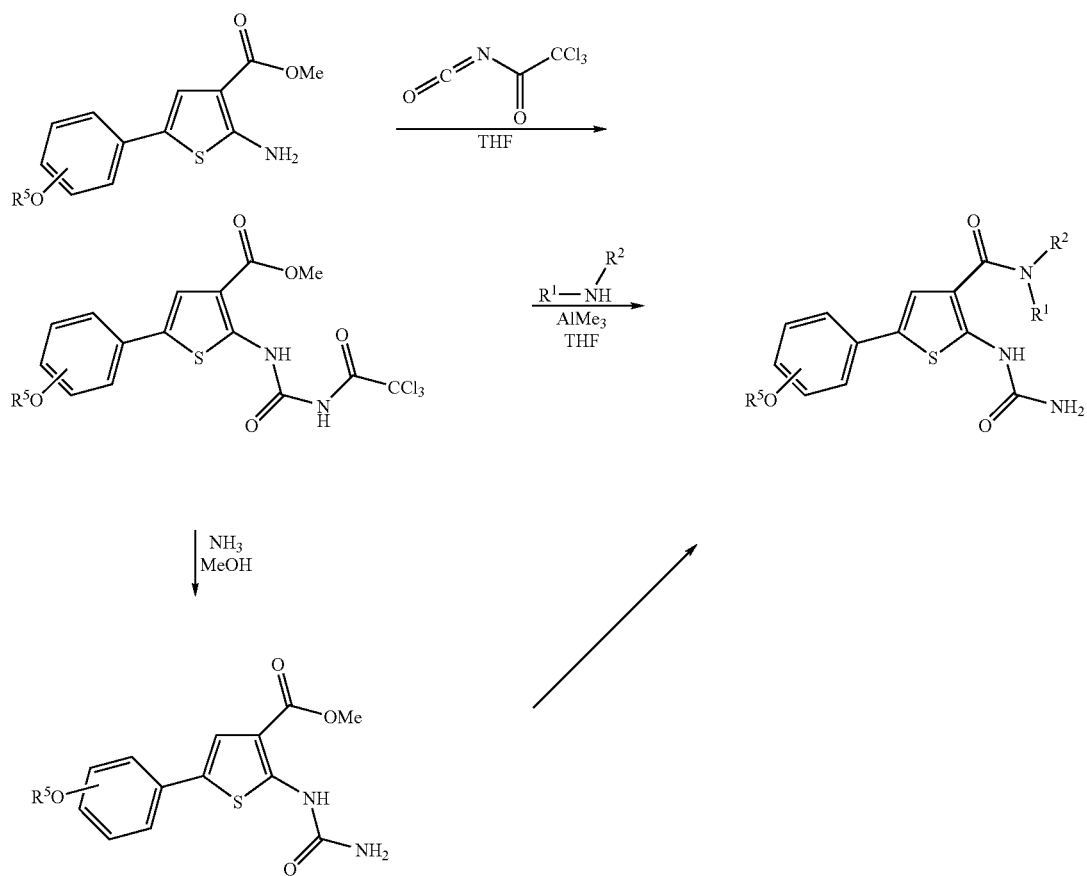

An alternate method for the generation of similar compounds is described in Scheme IV. This general route utilizes the same starting 2-aminothiophene ester from Scheme III but amide bond formation is executed from the reaction of the corresponding carboxylic acids with various amines. A variety of coupling agents can be used to effect this transformation including EDCI, DIC, BOP, and HATU under standard coupling methods very familiar to those practicing and trained in the art of organic synthesis. Generation of the final primary urea is then performed using a simple two-step reaction with trichloroacetylisocyanate followed by cleavage with ammonia in methanol.

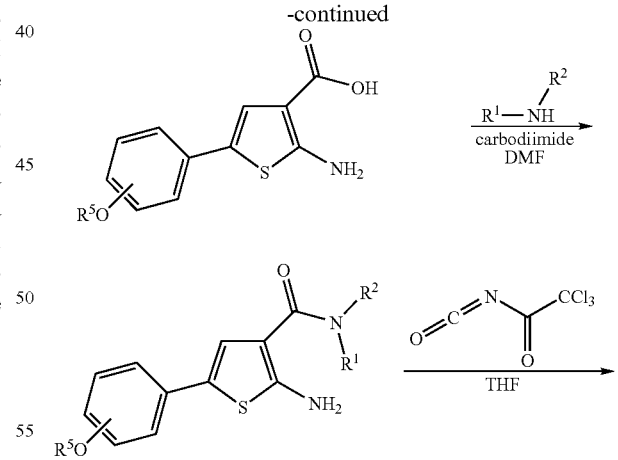

Scheme IV

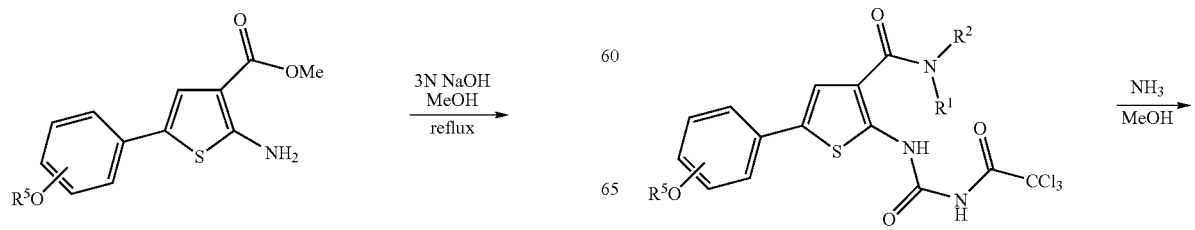

-continued

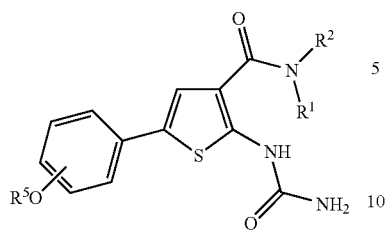

As shown in the following Schemes V-VII, the amide product formed prior to urea generation in Scheme IV can be used as a common intermediate for the formation of various substituted ureas where $R^4$ is not hydrogen. Reaction with isocyanantes, acyl azides (in particular pyrazine acyl azides), or carbonyldiimidazole and amines (in particular hydroxylamine hydrochloride), leads to the creation of various substituted secondary ureas where $R^4$ is selected from OH, optionally substituted carbocyclyl, optionally substituted heterocyclyl, or optionally substituted $C_{1-6}$alkyl.

Scheme V

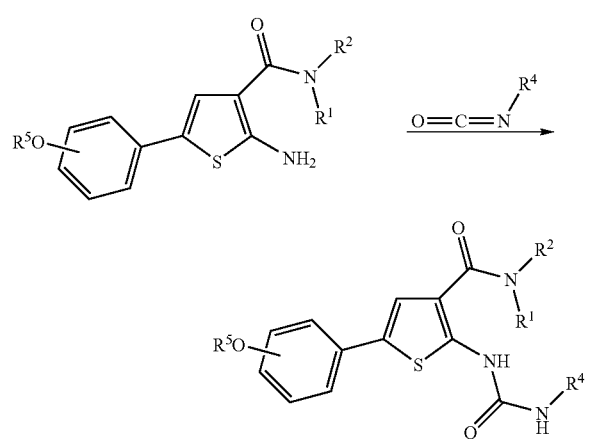

Scheme VI

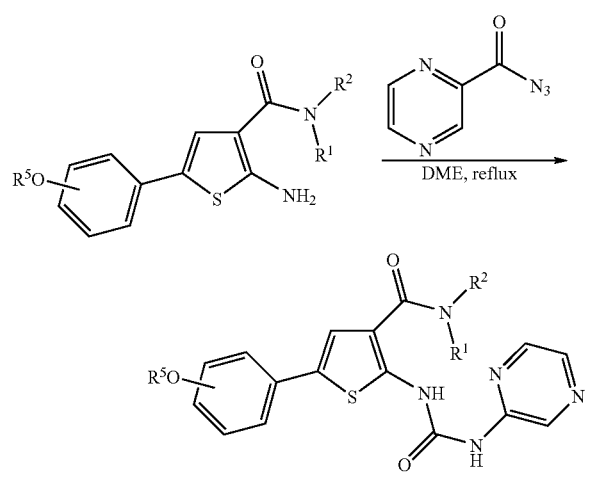

Scheme VII

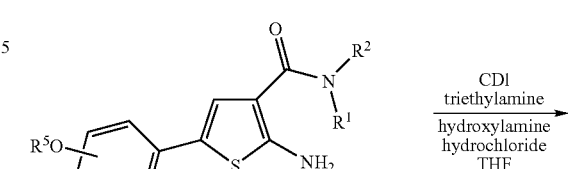

An additional general process presented in this invention involves an improvement on the construction of general compounds with formula (I). The method, which employs a Suzuki Coupling of a 5-bromothiophene intermediate as its key transformation, is shown in Scheme VIII. This method allows for increased diversity much later in the synthesis and is amenable to parallel combinatorial methods of organic synthesis. Commercially available 2-amino-thiophene-3-carboxylic acid methyl ester is protected as the trichloroacetyl urea, followed by selective bromination at the 5-position with bromine in acetic acid. Removal of the protecting group with ammonia in methanol, followed by Weinreb amidation yields the common intermediate. Standard Suzuki reaction conditions are then employed to finally generate the target compounds.

Scheme VIII

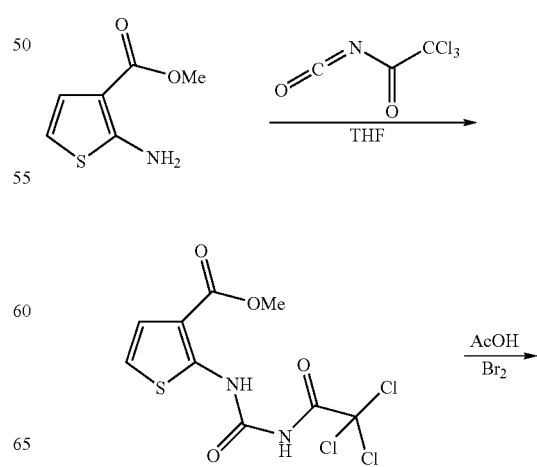

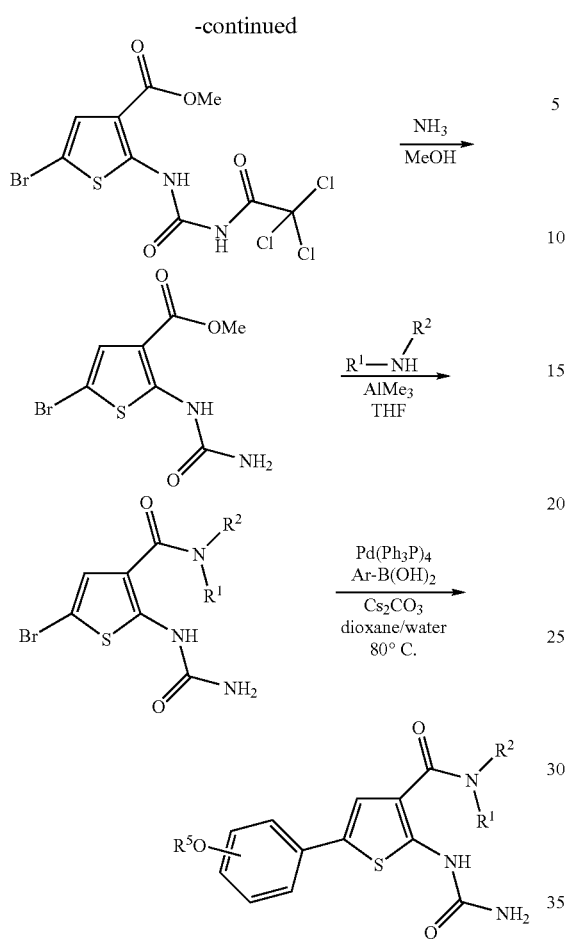

If the final compound generated from any of the above-mentioned methods or schemes has a protecting group on nitrogen (in particular a carbamate) or oxygen (in particular an ether or ester) present anywhere on the molecule standard methods of removal can be utilized to generate final compounds. Shown in Scheme IX is the general method used for the deprotection of a tert-butoxycarbonyl carbamate to yield the secondary amine product ($R^2$=$XNHR^3$) as the corresponding hydrochloride or trifluoroacetate salt. Cleavage of methyl ethers to phenols (not shown) is affected by reaction with boron tribromide in methylene chloride. Both of these methods are very familiar with those trained in the art of organic synthesis.

Scheme IX

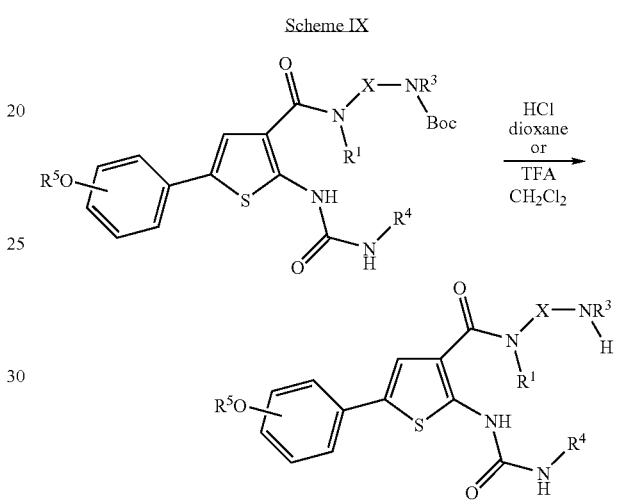

EXAMPLES

TABLE 1

| IUPAC Name | Ex. | LCMS (M+1, ES or APCI detection) | $^1$H NMR ($d_6$-DMSO unless stated otherwise) | Synthesis Method (Scheme) |
|---|---|---|---|---|
| tert-butyl 3-{[(2-[(aminocarbonyl)amino]-5-{4-[2-(diethylamino)ethoxy]phenyl}-3-thienyl)carbonyl]amino}piperidine-1-carboxylate trifluoroacetate | 1 | 560 | MeOD; 7.55(d, 2H), 7.45(s, 1H), 7.05(d, 2H), 4.35(m, 2H), 3.90(m, 3H), 3.60(m, 2H), 3.30(m, 4H), 2.95(dd, 2H), 2.10(m, 1H), 1.80(m, 1H), 1.50(m, 2H), 1.40(s, 9H), 1.35(t, 6H) | III |
| 2-[(aminocarbonyl)amino]-5-{4-[2-(diethylamino)ethoxy]phenyl}-N-piperidin-3-ylthiophene-3-carboxamide trifluoroacetate | 2 | 460 | | III |
| 2-[(aminocarbonyl)amino]-5-{3-[2-(diethylamino)ethoxy]phenyl}-N-piperidin-3-ylthiophene-3-carboxamide trifluoroacetate | 3 | 460 | | III |
| 2-[(aminocarbonyl)amino]-5-(4-methoxyphenyl)-N-[(3S)-piperidin-3-yl]thiophene-3-carboxamide | 4 | 375 | 1.76-1.49(m, 2H), 1.93(brs, 2H), 2.85(t, 2H), 3.16(s, 1H), 3.22(brd, 1H), 3.31(brd, 1H), 3.77(s, 3H), 4.11(brs, 1H), 6.97(d, 2H, J=8.59Hz), 7.45(d, 2H, J=8.59Hz), 7.58(s, 1H), 8.02(d, 1H, J=7.33Hz), 8.65(brs, 2H), 10.81(s, 1H) | III |

TABLE 1-continued

| IUPAC Name | Ex. | LCMS (M+1, ES or APCI detection) | $^1$H NMR (d$_6$-DMSO unless stated otherwise) | Synthesis Method (Scheme) |
|---|---|---|---|---|
| tert-butyl 3-{[(2-[(aminocarbonyl)amino]-5-{3-[2-(diethylamino)ethoxy]phenyl}-3-thienyl)carbonyl]amino}piperidine-1-carboxylate trifluoroacetate | 5 | 560 | MeOD; 7.65(d, 1H), 7.30(dd, 2H), 7.20(s, 1H), 6.90(d, 1H), 4.35(m, 2H), 3.90(m, 2H), 3.60(m, 2H), 3.30(m, 4H), 3.00(m, 2H), 2.10(m, 1H), 1.80(m, 1H), 1.50(m, 2H), 1.45(s, 9H), 1.40(t, 6H) | III |
| 2-[(aminocarbonyl)amino]-5-{4-[2-(diethylamino)ethoxy]phenyl}-N-piperidin-4-ylthiophene-3-carboxamide | 6 | 460 | MeOD; 7.52(d, 2H), 7.49(s, 1H), 7.01(d, 2H), 4.35(m, 2H), 3.60(m, 2H), 3.48(m, 1H), 3.42(m, 2H), 3.33(q, 4H), 3.13(m, 2H), 2.14(m, 2H), 1.85(m, 2H), 1.35(t, 6H) | III |
| 2-[(aminocarbonyl)amino]-N-[(3R)-azepan-3-yl]-5-(4-methoxyphenyl)thiophene-3-carboxamide | 7 | 389 | CDCl3; 11.30(br s, 1H), 7.50(d, 2H), 7.05(d, 1H), 7.00(s, 1H), 6.85(d, 2H), 5.15(s, 2H), 4.20(m, 1H), 3.80(s, 3H), 3.10(m, 1H), 3.00(m, 2H), 2.80(m, 1H), 1.80(m, 2H), 1.70(m, 3H), 1.50(m, 1H) | III |
| N-(3-[(4-aminopiperidin-1-yl)carbonyl]-5-{4-[2-(diethylamino)ethoxy]phenyl}-2-thienyl)urea trifluoroacetate | 8 | 460 | MeOD; 7.43(d, 2H), 6.93(d, 2H), 6.92(s, 1H), 4.33(m, 2H), 4.27(dd, 2H), 3.52(dd, 2H), 3.32(m, 1H), 3.24(q, 4H), 3.02(m, 2H), 1.99(m, 1H), 1.95(m, 1H), 1.47(m, 2H), 1.27(t, 6H) | III |
| 2-[(aminocarbonyl)amino]-5-{4-[2-(diethylamino)ethoxy]phenyl}-N-[3-(hydroxymethyl)phenyl]thiophene-3-carboxamide trifluoroacetate (salt) | 9 | 483 | MeOD; 7.61(m, 1H), 7.57(s, 1H), 7.49(m, 1H), 7.47(d, 2H), 7.23(t, 1H), 7.03(dd, 1H), 6.93(d, 2H), 4.52(s, 2H), 4.27(dd, 2H), 4.31(dd, 2H), 3.24(q, 4H), 1.27(t, 6H) | III |
| 2-[(aminocarbonyl)amino]-5-{3-[2-(diethylamino)ethoxy]phenyl}-N-piperidin-4-ylthiophene-3-carboxamide trifluoroacetate | 10 | 460 | MeOD; 7.62(s, 1H), 7.29(dd, 1H), 7.24(m, 1H), 7.13(m, 1H), 6.87(m, 1H), 4.35(dd, 2H), 3.59(dd, 2H), 3.46(m, 1H), 3.40(m, 2H), 3.31(q, 4H), 3.10(m, 2H), 2.16(m, 2H), 1.83(m, 2H), 1.34(t, 6H) | III |
| 2-[(aminocarbonyl)amino]-N-(2-aminoethyl)-5-(4-methoxyphenyl)thiophene-3-carboxamide | 11 | 335 | MeOD; 7.38(d, 2H), 7.36(s, 1H), 6.82(d, 2H), 3.70(s, 3H), 3.57(dd, 2H), 3.10(dd, 2H), | III |
| 2-[(aminocarbonyl)amino]-5-(4-methoxyphenyl)-N-piperidin-4-ylthiophene-3-carboxamide | 12 | 375 | 1.70(m, 2H), 1.99(d, 2H, J=12.88Hz), 3.01(q, 2H, J=11.03Hz), 3.35(d, 2H, J=12.38Hz), 3.76(s, 3H), 4.01(brs, 1H), 6.97(d, 2H, J=8.59Hz), 7.45(d, 2H, J=8.84Hz), 7.63(s, 1H), 8.04(d, 1H, J=7.07Hz), 8.43(d, 1H, J=9.10Hz), 8.65(d, 1H, J=8.59Hz), 10.91(s, 1H) | III |
| 2-[(aminocarbonyl)amino]-5-{3-[2-(diethylamino)ethoxy]phenyl}-N-pyridin-3-ylthiophene-3-carboxamide trifluoroacetate | 13 | 454 | MeOD; 9.51(s, 1H), 8.75(d, 1H), 8.51(m, 1H), 7.97(s, 1H), 7.93(m, 1H), 7.35(t, 1H), 7.29(m, 2H), 6.93(m, 1H), 4.45(dd, 2H), 3.67(dd, 2H), 3.39(q, 4H), 1.42(t, 6H) | III |
| 2-[(aminocarbonyl)amino]-5-(4-methoxyphenyl)-N-(1-methylpiperidin-4-yl)thiophene-3-carboxamide | 14 | 389 | 1.76(q, 2H), 2.04(d, 2H, J=12.38Hz), 2.77(brd, 3H), 3.08(q, 2H), 3.48(d, 2H, J=11.62Hz), 3.76(s, 3H), 3.96(m, 1H), 6.97(d, 2H), 7.45(d, 2H, J=8.84Hz), 7.63(s, 1H), 8.07(d, 1H, J=7.33Hz), 9.62(brs, 1H), 10.91(s, 1H) | III |
| 2-[(aminocarbonyl)amino]-5-(4-methoxyphenyl)-N-[(3S)-1- | 15 | 403 | CDCl3; 11.35(br s, 1H), 7.50(d, 2H), 7.15(d, 1H), 6.95(s, | III |

TABLE 1-continued

| IUPAC Name | Ex. | LCMS (M+1, ES or APCI detection) | $^1$H NMR ($d_6$-DMSO unless stated otherwise) | Synthesis Method (Scheme) |
|---|---|---|---|---|
| methylazepan-3-yl]thiophene-3-carboxamide hydrochloride | | | 1H), 6.90(d, 2H), 5.30(s, 2H), 4.20(m, 1H), 3.80(s, 3H), 2.85(m, 1H), 2.80(d, 1H), 2.60(dd, 1H), 2.40(m, 1H), 2.45(s, 3H), 1.50-2.00(m, 6H) | |
| 2-[(aminocarbonyl)amino]-5-{3-[2-(diethylamino)ethoxy]phenyl}-N-[3-(hydroxymethyl)phenyl]thiophene-3-carboxamide trifluoroacetate (salt) | 16 | 483 | MeOD; 7.84(s, 1H), 7.75(m, 1H), 7.63(dd, 1H), 7.35(t, 2H), 7.32(m, 1H), 7.22(m, 1H), 7.16(dd, 1H), 6.92(m, 1H), 4.65(s, 2H), 4.41(dd, 2H), 3.63(dd, 2H), 3.37(q, 4H), 1.40(t, 6H) | III |
| 2-[(aminocarbonyl)amino]-5-{4-[2-(diethylamino)ethoxy]phenyl}-N-pyrrolidin-3-ylthiophene-3-carboxamide trifluoroacetate | 17 | 446 | MeOD; 7.46(d, 2H), 7.16(s, 1H), 6.95(d, 2H), 4.28(dd, 2H), 3.89(m, 3H), 3.70(m, 2H), 3.53(dd, 2H), 3.28(q, 4H), 2.30(m, 1H), 2.06(m, 1H), 1.29(t, 6H) | III |
| 2-[(aminocarbonyl)amino]-5-{4-[2-(diethylamino)ethoxy]phenyl}-N-pyridin-3-ylthiophene-3-carboxamide trifluoroacetate | 18 | 454 | MeOD; 9.59(s, 1H), 8.75(d, 1H), 8.56(d, 1H), 8.00(m, 2H), 7.71(s, 1H), 7.59(d, 2H), 7.07(d, 2H), 4.41(dd, 2H), 3.65(dd, 2H), 3.38(q, 4H), 1.40(t, 6H) | III |
| 2-[(aminocarbonyl)amino]-5-(4-methoxyphenyl)-N-[(3S)-1-methylpiperidin-3-yl]thiophene-3-carboxamide hydrochloride | 19 | 389 | CDCl3; 11.25(br s, 1H), 7.50(d, 2H), 7.15(s, 1H), 6.85(d, 2H), 6.90(m, 2H), 5.40(s, 2H), 4.25(m, 1H), 3.80(s, 3H), 2.40-2.80(m, 4H), 2.30(s, 3H), 2.20(m, 1H), 1.50-1.90(m, 3H) | III |
| 2-[(aminocarbonyl)amino]-5-{3-[2-(diethylamino)ethoxy]phenyl}-N-pyrrolidin-3-ylthiophene-3-carboxamide trifluoroacetate | 20 | 446 | MeOD; 7.40(s, 1H), 7.35(dd, 1H), 7.27(dd, 1H), 7.20(s, 1H), 6.93(m, 1H), 4.42(dd, 2H), 4.01(m, 3H), 3.83(m, 2H), 3.65(dd, 2H), 3.37(q, 4H), 2.44(m, 1H), 2.18(m, 1H), 1.40(t, 6H) | III |
| 2-[(aminocarbonyl)amino]-5-(4-methoxyphenyl)-N-[(3R)-piperidin-3-ylmethyl]thiophene-3-carboxamide | 21 | 389 | 1.22(dd, 1H, J1=12.38Hz, J2=2.53Hz), 1.57(d, 1H, J=13.14Hz), 1.78(brt, 2H), 1.95(brs, 1H), 2.60(q, 1H, J=11.37), 2.78(q, 1H, J=10.61Hz), 3.09(m, 1H), 3.25(m, 3H), 3.77(s, 3H), 6.97(d, 2H, J=8.59Hz), 7.44(d, 2H, J=8.84Hz), 7.58(s, 1H), 8.24(brs, 1H), 8.30(brt, 1H), 8.57(brs, 1H), 10.92(s, 1H) | III |
| 2-[(aminocarbonyl)amino]-5-(4-methoxyphenyl)-N-[(3S)-pyrrolidin-3-yl]thiophene-3-carboxamide | 22 | 361 | | III |
| 2-[(aminocarbonyl)amino]-5-(4-methoxyphenyl)-N-[(3R)-pyrrolidin-3-yl]thiophene-3-carboxamide | 23 | 361 | | III |
| 2-[(aminocarbonyl)amino]-N-[2-(dimethylamino)ethyl]-5-(4-methoxyphenyl)thiophene-3-carboxamide | 24 | 363 | MeOD; 7.37(d, 2H), 7.35(s, 1H), 6.80(d, 2H), 3.69(s, 3H), 3.64(m, 2H), 3.29(m, 2H), 2.91(s, 6H) | III |
| 2-[(aminocarbonyl)amino]-N-[2-(diethylamino)ethyl]-5-(4-methoxyphenyl)thiophene-3-carboxamide | 25 | 391 | | III |
| 2-[(aminocarbonyl)amino]-N-[(3S)-azepan-3-yl]-5-(4-methoxyphenyl)thiophene-3-carboxamide hydrochloride | 26 | 389 | δ 10.9, s, 1H; δ 9.58, br s, 1H; δ 9.29, br s, 1H; δ 8.39, d, 1H; δ 7.82, s, 1H; δ 7.48, d, 2H; δ 6.96, d, 2H; δ 4.36, m, 1H; δ 3.77, s, 3H; δ 3.29, m, 1H; δ 3.20, m, 2H; δ 3.07, m, 1H; δ 1.98, m, 1H; δ 1.84, m, 4H; δ 1.59, m, 1H | III |
| 2-[(aminocarbonyl)amino]-5-(4-methoxyphenyl)-N-[(3R)-piperidin-3-yl]thiophene-3-carboxamide | 27 | 375 | 1.52(m, 2H), 1.76(brs, 1H), 1.89(brs, 1H), 2.61(m, 2H), 2.99(t, 1H), 3.16(m, 1H), 3.76(s, 3H), 3.95(brs, 1H), 6.97(d, | III |

TABLE 1-continued

| IUPAC Name | Ex. | LCMS (M+1, ES or APCI detection) | $^1$H NMR (d$_6$-DMSO unless stated otherwise) | Synthesis Method (Scheme) |
|---|---|---|---|---|
| 2-[(aminocarbonyl)amino-5-(4-methoxyphenyl)-N-(piperidin-4-ylmethyl)thiophene-3-carboxamide | 28 | 389 | 2H), 7.46(d, 2H), 7.61(s, 1H), 7.89(d, 1H), 10.90(s, 1H) 1.06(m, 2H), 1.62(d, 3H, J=10.11Hz), 2.95(d, 2H, J=12.13Hz), 3.11(t, 2H, J=5.68Hz), 3.76(s, 3H), 6.90(d, 1H, J=8.59Hz), 6.96(d, 2H, J=8.59Hz), 7.44(d, 2H, J=8.59Hz), 7.61(s, 1H), 8.14(t, 1H, J=5.43Hz), 10.99(s, 1H) | III |
| 2-[(aminocarbonyl)amino]-5-(4-methoxyphenyl)-N-pyrrolidin-3-ylthiophene-3-carboxamide | 29 | 361 | 2.02(brt, 2H, J=5.81Hz), 2.22(dd, 2H, J1=13.52Hz, J2=6.69Hz), 3.21(dd, 1H, J1=13.77Hz, J2=6.95Hz), 3.68(brs, 1H), 3.76(s, 3H), 3.86(brs, 1H), 6.96(brm, 2H), 7.28(brs, 1H), 7.50(d, 2H, J=8.84Hz), 8.16(brs, 1H), 10.31(s, 1H) | III |
| 2-[(aminocarbonyl)amino]-N-(1-ethylpiperidin-3-yl)-5-(4-methoxyphenyl)thiophene-3-carboxamide hydrochloride | 30 | 403 | 11.0(s, 1H), 7.80(d, 1H), 7.65(s, 1H), 7.45(d, 2H), 6.95(d, 2H), 6.90(br s, 2H), 3.90(m, 1H), 3.75(s, 3H), 2.85(dd, 2H), 2.30(m, 2H), 1.80(m, 3H), 1.70(m, 1H), 1.50(m, 1H), 13.0(m, 1H), 1.0(t, 3H) | III |
| 2-[(aminocarbonyl)amino]-N-[(3S)-1-ethylazepan-3-yl]-5-(4-methoxyphenyl)thiophene-3-carboxamide hydrochloride | 31 | 417 | 11.0(s, 1H), 7.75(d, 1H), 7.65(s, 1H), 7.45(d, 2H), 6.95(d, 2H), 6.90(br s, 2H), 4.05(m, 1H), 3.75(s, 3H), 2.75(m, 1H), 2.40-2.70(m, 5H), 1.85(m, 1H), 1.40-1.75(m, 5H), 0.95(t, 3H) | III |
| 2-[(aminocarbonyl)amino]-5-(3-hydroxyphenyl)-N-piperidin-4-ylthiophene-3-carboxamide | 32 | 361 | | III |
| 2-[(aminocarbonyl)amino]-5-(4-hydroxyphenyl)-N-piperidin-4-ylthiophene-3-carboxamide | 33 | 361 | | III |
| 2-[(aminocarbonyl)amino]-5-(3-methoxyphenyl)-N-piperidin-4-ylthiophene-3-carboxamide | 34 | 375 | | III |
| tert-butyl (3S)-3-({[2-[(aminocarbonyl)amino]-5-(4-methoxyphenyl)-3-thienyl]carbonyl}amino)pyrrolidine-1-carboxylate | 35 | 481 | | III |
| 2-[(aminocarbonyl)amino]-5-(4-methoxyphenyl)-N-piperidin-3-ylthiophene-3-carboxamide | 36 | 375 | | III |
| 2-[(aminocarbonyl)amino]-N-(1-benzylpiperidin-4-yl)-5-(4-methoxyphenyl)thiophene-3-carboxamide | 37 | 465 | 1.75(m, 2H), 2.08(d, 2H, J=13.39Hz), 3.10(m, 2H), 3.43(d, 2H, J=11.62Hz), 3.76(s, 3H), 3.95(m, 1H), 4.31(d, 2H, J=4.55Hz), 6.97(d, 2H, J=8.59Hz), 7.45(d, 2H, J=8.59Hz), 7.49(brs, 5H, J=2.27Hz), 7.61(s, 1H), 8.05(d, 1H, J=6.82Hz), 9.65(brs, 1H), 10.89(s, 1H) | III |
| tert-butyl 3-({[2-[(aminocarbonyl)amino]-5-(4-methoxyphenyl)-3-thienyl]carbonyl}amino)piperidine-1-carboxylate | 38 | 475 | 1.39(s, 9H), 1.46-1.97(bm, 4H), 2.72(t, 2H), 3.16(s, 2H), 3.77(s, 3H), 6.96(d, 2H), 7.45(d, 2H), 7.62(s, 1H), 7.85(brs, 1H), 8.77(d, 1H), 10.95(s, 1H) | III |
| 2-[(aminocarbonyl)amino]-5-[4-(2-piperidin-1-ylethoxy)phenyl]-N-(2-pyridin-4-ylethyl)thiophene-3-carboxamide | 39 | 494 | | III |
| 2-[(aminocarbonyl)amino]-5-[4-(2-piperidin-1-ylethoxy)phenyl]-N-(2-pyridin-4-ylethyl)thiophene-3-carboxamide | 40 | 451 | | III |
| 2-[(aminocarbonyl)amino]-N-azetidin-3-yl-5-(4-methoxyphenyl)thiophene-3-carboxamide | 41 | 347 | | III |

TABLE 1-continued

| IUPAC Name | Ex. | LCMS (M+1, ES or APCI detection) | $^1$H NMR (d$_6$-DMSO unless stated otherwise) | Synthesis Method (Scheme) |
|---|---|---|---|---|
| 2-[(aminocarbonyl)amino]-5-(4-methoxyphenyl)-N-[(2S)-pyrrolidin-2-ylmethyl]thiophene-3-carboxamide | 42 | 375 | 1.71(m, 1H), 1.92(m, 2H), 2.04(m, 1H), 3.33-3.11(m, 2H), 3.62-3.45(m, 2H), 3.76(s, 3H), 6.97(d, 2H, J=8.84Hz), 7.45(d, 2H, J=8.59Hz), 7.52(s, 1H), 7.94(s, 1H), 8.47(t, 1H, J=5.81Hz), 8.52(brs, 1H), 9.15(brs, 1H), 10.79(s, 1H) | III |
| 2-[(aminocarbonyl)amino]-5-(4-methoxyphenyl)-N-pyridin-4-ylthiophene-3-carboxamide | 43 | 369 | 3.78(s, 3H), 7.01(d, 2H), 7.52(d, 2H), 7.79(s, 1H), 8.15(d, 2H), 8.70(brs, 2H), 10.62(s, 1H), 10.68(brs, 1H) | III |
| 2-[(aminocarbonyl)amino]-5-(4-methoxyphenyl)-N-(2-piperazin-1-ylethyl)thiophene-3-carboxamide | 44 | 404 | 2.06(m, 4H), 2.34(brs, 2H), 2.42(m, 2H), 2.67(m, 4H), 3.76(s, 3H), 6.97(d, 2H, J=8.84Hz), 7.44(d, 2H, J=8.59Hz), 7.55(s, 1H), 8.10(t, 1H, J-5.68Hz), 10.95(s, 1H) | III |
| 2-[(aminocarbonyl)amino]-5-(4-methoxyphenyl)-N-(2-piperidin-1-ylethyl)thiophene-3-carboxamide | 45 | 403 | 1.37(s, 2H), 1.48(s, 4H), 2.37(brs, 4H), 2.42(t, 2H), 3.76(s, 3H), 6.94(brs, 1H), 6.97(d, 2H), 7.44(d, 2H), 7.56(t, 2H), 8.11(t, 1H), 10.96(s, 1H) | III |
| 2-[(aminocarbonyl)amino]-N-1-azabicyclo[2.2.2]oct-3-yl-5-(4-methoxyphenyl)thiophene-3-carboxamide | 46 | 401 | | III |
| 2-[(aminocarbonyl)amino]-N-(2-hydroxyethyl)-5-(4-hydroxyphenyl)thiophene-3-carboxamide | 48 | 322 | 3.06(t, 1H), 3.5(m, 2H), 6.54(bs, 1H), 6.78-6.97(m, 4H), 7.33(m, 2H), 7.49(s, 1H), 8.34(m, 1H), 9.56(s, 1H), 10.94(s, 1H) | III |
| 2-[(aminocarbonyl)amino]-N-(trans-4-hydroxycyclohexyl)-5-(4-methoxyphenyl)thiophene-3-carboxamide | 49 | 390 | 1.10-1.45(dq, 4H), 1.85(t, 4H), 3.40(brs, 1H), 3.71(brm, 1H), 3.76(s, 3H), 4.56(brs, 1H), 6.90(brs, 1H), 6.96(d, 2H), 7.45(d, 2H), 7.62(s, 1H), 7.81(d, 1H), 11.03(s, 1H) | III |
| 2-[(aminocarbonyl)amino]-5-(4-hydroxyphenyl)-N-(2-pyridin-4-ylethyl)thiophene-3-carboxamide | 50 | 383 | 3.17(t, 2H, J=6.44Hz), 3.64(m, 2H), 6.77(d, 2H, J=8.59Hz), 7.31(d, 2H, J=8.59Hz), 7.45(s, 1H), 7.97(d, 2H, J=6.32Hz), 8.27(s, 1H), 8.83(d, 2H, J=6.06Hz), 10.79(s, 1H) | III |
| 2-[(aminocarbonyl)amino]-5-(4-methoxyphenyl)-N-(2-piperazin-1-ylethyl)thiophene-3-carboxamide | 52 | 525 | 1.34-1.58(m, 2H), 1.75(t, 2H, J=14.02Hz), 1.98(brs, 1H), 2.01(d, 1H), 2.80(m, 3H), 3.48(d, 2H, J=8.59Hz), 3.73(s, 6H), 3.75(s, 3H), 6.63(dd, 2H, J1=8.34Hz, J2=4.80Hz), 6.90(brs, 1H), 6.95(d, 2H, J=8.59Hz), 7.21(t, 2H), 7.45(d, 2H, J=8.84Hz), 7.46(s, 1H), 7.86(d, 1H, J=7.58Hz), 11.00(s, 1H) | III |
| 2-[(aminocarbonyl)amino]-5-(4-methoxyphenyl)-N-(2-pyridin-4-ylethyl)thiophene-3-carboxamide | 54 | 397 | 3.12(t, 2H), 3.62(t, 2H), 3.76(s, 3H), 6.97(d, 2H), 7.42(d, 2H), 7.49(s, 1H), 7.85(d, 2H), 8.28(s, 1H), 8.78(d, 2H), 10.84(s, 1H) | III |
| 2-[(aminocarbonyl)amino]-5-(4-hydroxyphenyl)-N-(2-pyridin-3-ylethyl)thiophene-3-carboxamide | 55 | 383 | 3.17(t, 2H, J=6.44Hz), 3.64(m, 2H), 6.77(d, 2H, J=8.59Hz), 7.31(d, 2H, J=8.59Hz), 7.45(s, 1H), 7.97(d, 2H, J=6.32Hz), 8.27(s, 1H), 8.83(d, 2H, J=6.06Hz), 10.79(s, 1H) | III |
| 2-[(aminocarbonyl)amino]-5-(4-methoxyphenyl)-N-(2-pyridin-3-ylethyl)thiophene-3-carboxamide | 56 | 397 | 2.99(t, 2H), 3.55(m, 2H), 3.76(s, 3H), 6.97(d, 2H), 7.42(d, 2H), 7.50(s, 1H), 7.76(m, 1H), 8.16(d, 1H), 8.25(s, 1H), 8.65(s, 1H), 8.69(s, 1H), 10.85(s, 1H) | III |

TABLE 1-continued

| IUPAC Name | Ex. | LCMS (M+1, ES or APCI detection) | $^1$H NMR (d$_6$-DMSO unless stated otherwise) | Synthesis Method (Scheme) |
|---|---|---|---|---|
| 2-[(aminocarbonyl)amino]-5-(4-methoxyphenyl)-N-(2,2,6,6-tetramethylpiperidin-4-yl)thiophene-3-carboxamide | 58 | 431 | 1.44(s, 12H), 1.63(t, 2H), 1.95(d, 2H), 3.76(s, 3H), 4.34(brs, 1H), 6.96(d, 2H), 7.45(d, 2H), 7.67(s, 1H), 8.12(m, 2H), 9.06(bd, 1H), 10.92(s, 1H) | III |
| 2-[(aminocarbonyl)amino]-5-(2-methoxyphenyl)-N-piperidin-4-ylthiophene-3-carboxamide | 59 | 375 | | III |
| 2-[(aminocarbonyl)amino]-5-(4-methoxyphenyl)-N-(tetrahydrofuran-2-ylmethyl)thiophene-3-carboxamide | 60 | 376 | 1.52(m, 1H), 1.77(m, 3H), 3.25(m, 2H), 3.72(m, 1H), 3.71(s, 3H), 3.93(m, 2H), 6.91(bd, 4H, J=8.84Hz), 7.39(d, 2H, J=8.59Hz), 7.59(s, 1H), 8.17(bs, 1H), 10.91(s, 1H) | III |
| tert-butyl (3R)-3-({[2-[(aminocarbonyl)amino]-5-(4-methoxyphenyl)-3-thienyl]carbonyl}amino)piperidine-1-carboxylate | 62 | 475 | 1.38(s, 9H), 1.47-1.99(brm, 6H), 3.56(brm, 2H), 3.74(brm, 1H), 3.76(s, 3H), 6.96(d, 2H, J=8.59Hz), 7.45(d, 2H, J=8.84Hz), 7.62(s, 1H), 7.85(brs, 1H), 8.77(d, 1H, J=7.58Hz), 10.96(s, 1H | III |
| 2-[(aminocarbonyl)amino]-5-(4-methoxyphenyl)-N-(pyridin-3-ylmethyl)thiophene-3-carboxamide | 63 | 383 | 3.76(s, 3H), 4.48(d, 2H), 6.96(d, 2H), 7.36(dd, 1H), 7.44(d, 2H), 7.61(s, 1H), 7.72(dt, 1H), 8.46(bdd, 1H), 8.56(bd, 1H), 8.77(t, 1H) | III |
| tert-butyl 3-({[2-[(aminocarbonyl)amino]-5-(4-methoxyphenyl)-3-thienyl]carbonyl}amino)azetidine-1-carboxylate | 64 | 447 | 1.39(s, 9H), 3.77(s, 3H), 3.86(m, 2H), 4.13(t, 2H, J=7.83Hz), 4.61(m, 1H), 6.97(d, 2H, J=8.84Hz), 7.45(d, 2H, J=8.59Hz), 7.60(s, 1H), 8.57(d, 1H, J=6.82Hz), 10.82(s, 1H) | III |
| 2-[(aminocarbonyl)amino]-5-(4-methoxyphenyl)-N-(pyridin-4-ylmethyl)thiophene-3-carboxamide | 65 | 383 | | III |
| 2-[(aminocarbonyl)amino]-5-(4-methoxyphenyl)-N-(3-methoxypropyl)thiophene-3-carboxamide | 67 | 364 | 1.76(m, 2H), 3.23(s, 3H), 3.30(t, 2H), 3.37(t, 2H), 3.76(s, 3H), 6.96(d, 2H), 7.44(d, 2H), 7.57(s, 1H), 8.15(brs, 1H), 10.97(s, 1H) | III |
| 2-[(aminocarbonyl)amino]-5-(4-methoxyphenyl)-N-[2-(2-thienyl)ethyl]thiophene-3-carboxamide | 68 | 402 | | III |
| 2-[(aminocarbonyl)amino]-5-(4-methoxyphenyl)-N-(2-thienylmethyl)thiophene-3-carboxamide | 69 | 388 | 3.76(s, 3H), 4.62(d, 2H), 6.96(d, 1H), 6.96(d, 2H), 7.03(d, 1H), 7.39(d, 1H), 7.43(d, 2H), 7.60(s, 1H), 8.79(t, 1H), 10.92(s, 1H) | III |
| N-[3-(1,4-diazepan-1-ylcarbonyl)-5-(4-methoxyphenyl)-2-thienyl]urea | 70 | 375 | 7.50 d J=8.8Hz 2H, 7.09 s 1H, 6.95 d J=8.8Hz 2H, 3.86 s 3H, 1.23-1.35 m 6H. | III |
| 2-[(aminocarbonyl)amino]-N-(2-methoxyethyl)-5-(4-methoxyphenyl)thiophene-3-carboxamide | 71 | 350 | 3.27(s, 3H), 3.37-3.51(m, 4H), 3.76(s, 3H), 6.97(d, 2H), 7.44(d, 2H), 7.61(s, 1H), 8.15-8.26(m, 1H), 10.95(s, 1H) | III |
| 2-[(aminocarbonyl)amino]-5-(4-hydroxyphenyl)-N-(2-thienylmethyl)thiophene-3-carboxamide | 72 | 374 | 4.61(d, 2H, J=5.81Hz), 6.77(d, 2H, J=8.59Hz), 6.96(dd, 2H, J1=5.05Hz, J2=3.54Hz), 7.02(d, 1H, J=3.03Hz), 7.32(d, 2H, J=8.34Hz), 7.38(d, 1H, J=5.05Hz), 7.53(s, 1H), 8.77(t, 1H, J=5.81Hz), 9.53(s, 1H), 10.89(s, 1H) | III |
| 2-[(aminocarbonyl)amino]-N-{2-[(2-furylmethyl)thio]ethyl}-5-(4-methoxyphenyl)thiophene-3-carboxamide | 74 | 432 | 2.61(t, 2H), 2.65(t, 2H), 3.75(s, 3H), 3.81(d, 2H), 6.29(d, 1H, J=3.03Hz), 6.38(dd, 1H, J1=3.03Hz, J2=1.77Hz), 6.97(d, 2H, J=8.84Hz), 7.44(d, 2H, J=8.84Hz), 7.55(s, 1H), 7.57(brs, 1H), 8.31(t, 1H, J=5.68Hz), 9.10(t, 1H, J=4.93Hz), 10.92(s, 1H) | III |

TABLE 1-continued

| IUPAC Name | Ex. | LCMS (M+1, ES or APCI detection) | $^1$H NMR ($d_6$-DMSO unless stated otherwise) | Synthesis Method (Scheme) |
|---|---|---|---|---|
| 2-[(aminocarbonyl)amino]-5-(4-hydroxyphenyl)-N-[2-(2-thienyl)ethyl]thiophene-3-carboxamide | 75 | 388 | 3.50(m, 2H), 3.80(m, 2H), 6.54(bs, 1H), 6.78-7.34(m, 7H), 7.49(s, 1H), 8.34(m, 1H), 9.56(s, 1H), 10.94(s, 1H) | III |
| N-(3-[(4-aminopiperidin-1-yl)carbonyl]-5-{3-[2-(diethylamino)ethoxy]phenyl}-2-thienyl)urea trifluoroacetate | 76 | 460 | MeOD; 7.24(dd, 1H), 7.16(dd, 1H), 7.08(s, 1H), 7.06(s, 1H), 6.83(dd, 1H), 4.34(m, 2H), 4.30(dd, 2H), 3.53(dd, 2H), 3.32(m, 1H), 3.27(q, 4H), 3.04(m, 2H), 1.99(m, 2H), 1.50(m, 2H), 1.28(t, 6H) | III |
| 2-[(aminocarbonyl)amino]-5-(4-methoxyphenyl)-N-[(3R)-piperidin-3-ylmethyl]thiophene-3-carboxamide | 77 | 389 | 1.22(dd, 1H, J1=12.38Hz, J2=2.53Hz), 1.57(d, 1H, J=13.14Hz), 1.78(brt, 2H), 1.95(brs, 1H), 2.60(q, 1H, J=11.37), 2.78(q, 1H, J=10.61Hz), 3.09(m, 1H), 3.25(m, 3H), 3.77(s, 3H), 6.97(d, 2H, J=8.59Hz), 7.44(d, 2H, J=8.84Hz), 7.58(s, 1H), 8.24(brs, 1H), 8.30(brt, 1H), 8.57(brs, 1H), 10.92(s, 1H) | III |
| 2-[(aminocarbonyl)amino]-5-(4-methoxyphenyl)-N-(1,2,3,4-tetrahydroquinolin-3-yl)thiophene-3-carboxamide | 78 | 423 | | III |
| 2-[(aminocarbonyl)amino]-N-(1,3-benzodioxol-5-ylmethyl)-5-(4-methoxyphenyl)thiophene-3-carboxamide | 79 | 426 | 3.76(s, 3H), 4.36(d, 2H), 5.97(s, 2H), 6.81(d, 1H), 6.89(d, 1H), 6.96(d, 2H), 7.44(d, 2H), 7.62(s, 1H), 8.64(t, 1H), 10.94(s, 1H) | III |
| 2-[(aminocarbonyl)amino]-N-(3-methoxybenzyl)-5-(4-methoxyphenyl)thiophene-3-carboxamide | 80 | 412 | 3.74(s, 3H), 3.78(s, 3H), 4.44(d, 2H, J=5.56Hz), 6.82(m, 1H), 6.91(m, 2H), 6.98(d, 2H, J=8.59Hz), 7.25(t, 2H, J=7.83), 7.46(d, 2H, J=8.59Hz), 7.66(s, 1H), 8.71(s, 1H), 10.95(s, 1H) | III |
| 2-[(aminocarbonyl)amino]-N-[2-(3,4-dimethoxyphenyl)ethyl]-5-(4-methoxyphenyl)thiophene-3-carboxamide | 81 | 456 | 3.73(s, 3H), 3.74(s, 3H), 3.77(s, 3H), 4.40(d, 2H, J=5.56Hz), 6.92(m, 7H), 7.45(d, 2H, J=8.84Hz), 7.66(s, 1H), 8.64(bs, 1H), 10.97(s, 1H) | III |
| 2-[(aminocarbonyl)amino]-5-(4-methoxyphenyl)-N-[(5-methyl-2-furyl)methyl]thiophene-3-carboxamide | 84 | 386 | 2.22(s, 3H), 3.76(s, 3H), 4.38(d, 2H), 5.99(s, 1H), 6.14(s, 1H), 6.96(d, 2H), 7.43(d, 2H), 7.64(s, 1H), 8.57(t, 1H), 10.93(s, 1H) | III |
| 2-[(aminocarbonyl)amino]-5-(4-methoxyphenyl)-N-(pyridin-2-ylmethyl)thiophene-3-carboxamide | 85 | 383 | 3.77(s, 3H), 4.69(d, 2H), 6.98(d, 2H), 7.46(d, 2H), 7.65(t, 1H), 7.73(t, 1H), 7.67(s, 1H), 8.20(t, 1H), 8.69(d, 1H), 8.96(t, 1H), 10.76(s, 1H) | III |
| 2-[(aminocarbonyl)amino]-N-(4-fluorobenzyl)-5-(4-methoxyphenyl)thiophene-3-carboxamide | 86 | 400 | | III |
| tert-butyl 4-({[2-[(aminocarbonyl)amino]-5-(3-methoxyphenyl)-3-thienyl]carbonyl}amino)piperidine-1-carboxylate | 88 | 475 | | III |
| 2-[(aminocarbonyl)amino]-N-(2-methoxybenzyl)-5-(4-methoxyphenyl)thiophene-3-carboxamide | 89 | 412 | 3.78(s, 3H), 3.83(s, 3H), 4.45(bd, 2h, J=5.56Hz), 6.97(m, 5H(, 7.23(m, 2H), 7.47(d, 2H, J=8.84), 7.71(s, 1H), 8.55(bt, 1H), 10.97(s, 1H) | III |
| 2-[(aminocarbonyl)amino]-5-(4-methoxyphenyl)-N-(2-phenoxyethyl)thiophene-3-carboxamide | 90 | 412 | 3.56-3.7(m, 2H), 3.76(s, 3H), 4.11(t, 2H), 6.85-7.05(m, 5H), 7.28(t, 2H), 7.44(d, 2H), 7.61(s, 1H), 8.38(brs, 1H), 10.93(s, 1H) | III |

TABLE 1-continued

| IUPAC Name | Ex. | LCMS (M+1, ES or APCI detection) | $^1$H NMR (d$_6$-DMSO unless stated otherwise) | Synthesis Method (Scheme) |
|---|---|---|---|---|
| 2-[(aminocarbonyl)amino]-5-(4-methoxyphenyl)-N-(2-pyridin-2-ylethyl)thiophene-3-carboxamide | 93 | 397 | 3.00(t, 2H, J=7.45Hz), 3.61(m, 2H), 3.76(s, 3H), 6.97(d, 2H, J=8.84Hz), 7.22(dd, 1H, J1=6.95Hz, J2=5.18Hz), 7.27(d, 1H, J=7.83Hz), 7.43(d, 2H, J=8.59Hz), 7.54(s, 1H), 7.70(dt, 1H, J1=7.58Hz, J2=1.77Hz), 8.27(t, 1H, J=5.56Hz), 8.51(d, 1H, J=4.55Hz), 10.97(s, 1H) | III |
| tert-butyl 4-({[2-[(aminocarbonyl)amino]-5-(4-methoxyphenyl)-3-thienyl]carbonyl}amino)piperidine-1-carboxylate | 94 | 475 | | III |
| 2-[(aminocarbonyl)amino]-N-(4-methoxybenzyl)-5-(4-methoxyphenyl)thiophene-3-carboxamide | 95 | 412 | 3.72(s, 3H), 3.76(s, 3H), 4.39(d, 2H), 6.89(d, 2H), 6.96(d, 2H), 7.25(d, 2H), 7.44(d, 2H), 7.63(s, 1H), 8.64(t, 1H), 10.95(s, 1H) | III |
| 2-[(aminocarbonyl)amino]-5-{4-[2-(diethylamino)ethoxy]phenyl}-N-[(3S)-piperidin-3-yl]thiophene-3-carboxamide trifluoroacetate | 110 | 460 | MeOD; 7.55(d, 2H), 7.45(s, 1H), 7.05(d, 2H), 4.35(dd, 2H), 4.25(m, 1H), 3.60(dd, 2H), 3.50(m, 1H), 3.30(m, 5H), 2.95(dd, 2H), 2.10(dd, 2H), 1.80(m, 2H), 1.35(t, 6H) | IV |
| 2-[(aminocarbonyl)amino]-5-{4-[2-(diethylamino)ethoxy]phenyl}-N-[(3R)-piperidin-3-yl]thiophene-3-carboxamide trifluoroacetate | 111 | 460 | MeOD; 7.55(d, 2H), 7.45(s, 1H), 7.05(d, 2H), 4.35(dd, 2H), 4.25(m, 1H), 3.60(dd, 2H), 3.50(m, 1H), 3.30(m, 5H), 2.95(dd, 2H), 2.10(dd, 2H), 1.80(m, 2H), 1.35(t, 6H) | IV |
| tert-butyl (3S)-3-{[(2-[(aminocarbonyl)amino]-5-{4-[2-(diethylamino)ethoxy]phenyl}-3-thienyl)carbonyl]amino}piperidine-1-carboxylate trifluoroacetate | 112 | 560 | MeOD; 7.55(d, 2H), 7.45(s, 1H), 7.05(d, 2H), 4.35(dd, 2H), 3.60-3.90(m, 3H), 3.60(dd, 2H), 3.30(m, 4H), 2.95(m, 2H), 1.90(dd, 2H), 1.55(m, 2H), 1.45(s, 9H), 1.35(t, 6H) | IV |
| 2-[(aminocarbonyl)amino]-N-[(3S)-azepan-3-yl]-5-{4-[2-(diethylamino)ethoxy]phenyl}thiophene-3-carboxamide hydrochloride | 113 | 474 | 10.85(s, 1H), 9.50(br s, 1H), 9.10(br s, 1H), 8.95(br s, 1H), 8.20(d, 1H), 7.65(s, 1H), 7.50(d, 2H), 7.05(d, 2H), 6.95, (br s 2H), 4.35(dd, 2H), 4.25(m, 1H), 3.50(dd, 2H), 3.10-3.40(m, 8H), 2.00(m, 1H), 1.80(m, 4H), 1.55(m, 1H), 1.25(m, 6H) | IV |
| tert-butyl (3R)-3-{[(2-[(aminocarbonyl)amino]-5-{4-[2-(diethylamino)ethoxy]phenyl}-3-thienyl)carbonyl]amino}piperidine-1-carboxylate trifluoroacetate | 114 | 560 | MeOD; 7.45(d, 2H), 7.35(s, 1H), 6.90(d, 2H), 4.25(dd, 2H), 3.60-3.90(m, 3H), 3.50(dd, 2H), 3.20(m, 5H), 2.85(s, 1H), 1.80(dd, 2H), 1.45(m, 2H), 1.35(s, 9H), 1.25(t, 6H) | IV |
| N-[3-{[(3S)-3-aminoazepan-1-yl]carbonyl}-5-(4-methoxyphenyl)-2-thienyl]urea hydrochloride | 115 | 389 | 9.65(s, 1H), 8.25(s, 3H), 7.50(d, 2H), 7.10(s, 1H), 6.90(d, 2H), 6.75(br s, 2H), 4.00(m, 1H), 3.80(s, 3H), 3.40(m, 4H), 2.0(m, 1H), 1.00-1.80(m, 5H) | IV |
| 2-({[(2,5-dimethoxyphenyl)amino]carbonyl}amino)-5-(4-methoxyphenyl)-N-piperidin-3-ylthiophene-3-carboxamide | 116 | 511 | 11.28 s 1H, 9.65 bs 1H, 9.08 bs 1H, 8.43 s 1H, 7.90 s 1H, 7.46 d J=8.7Hz 2H, 6.83 d J=8.8Hz 2H, 6.65 d J=8.8Hz 1H, 6.43-6.47 m 1H, 4.35 bs 1H, 3.76 s 3H, 7.73 s 3H, 3.54 s 3H, 3.24-3.45 m 2H, 2.81 bs 2H, 2.44 bs 4H. | V |
| 5-{4-[2-(diethylamino)ethoxy]phenyl}-2-{[(pyrazin-2-ylamino)carbonyl]amino}-N-[(3S)-pyrrolidin-3-yl]thiophene-3-carboxamide | 120 | 524 | 1.21(t, 6H), 2.00(m, 1H), 2.20(m, 1H), 3.18(m, 4H), 3.43(m, 6H), 4.31(t, 2H), 4.53(m, 1H), 7.05(d, 2H), 7.52(d, 2H), 7.70(s, 1H), 8.30(m, 3H), 8.78(s, 1H), 8.85(s, 1H), 8.98(s, 1H), 9.32(s, 1H), 10.90(s, 1H) | VI |

TABLE 1-continued

| IUPAC Name | Ex. | LCMS (M+1, ES or APCI detection) | $^1$H NMR (d$_6$-DMSO unless stated otherwise) | Synthesis Method (Scheme) |
|---|---|---|---|---|
| 5-{3-[2-(diethylamino)ethoxy]phenyl}-2-{[(pyrazin-2-ylamino)carbonyl]amino}-N-[(3S)-pyrrolidin-3-yl]thiophene-3-carboxamide hydrochloride | 121 | 524 | 1.25(t, 6H), 2.02(m, 1H), 2.20(m, 1H), 3.22(m, 4H), 3.43(m, 6H), 4.34(t, 2H), 4.53(m, 1H), 6.92(d, 1H), 7.12(s, 1H), 7.28(d, 1H), 7.39(dxd, 1H), 7.84(s, 1H), 8.32(m, 3H), 8.78(s, 1H), 8.85(s, 1H), 8.98(s, 1H), 9.30(s, 1H), 10.92(s, 1H) | VI |
| 5-{3-[2-(diethylamino)ethoxy]phenyl}-N-piperidin-4-yl-2-{[(pyrazin-2-ylamino)carbonyl]amino}thiophene-3-carboxamide | 122 | 538 | ): 0.95(t, 6H), 1.52(m, 2H), 1.62(m, 4H), 2.52(m, 4H), 2.78(m, 4H), 3.00(m, 12H), 3.18(t, 2H), 4.05(t, 2H), 6.68(bs, 1H), 6.80(d, 1H), 7.10(m, 2H), 7.28(m, 2H), 7.82(s, 1H), 8.22(s, 1H), 8.28(s, 1H), 9.00(s, 1H) | VI |
| N-[(3S)-azepan-3-yl]-5-(4-methoxyphenyl)-2-{[(pyrazin-2-ylamino)carbonyl]amino}thiophene-3-carboxamide hydrochloride | 123 | 467 | δ 12.6, br s, 1H; δ 10.9, s, 1H; δ 9.55, br s, 1H; δ 9.24, br s, 1H; δ 8.88, s, 1H; δ 8.49, d, 1H; δ 8.35, dd, 1H; δ 8.29, d, 1H; δ 7.92, s, 1H; δ 7.54, d, 2H; δ 6.99, d, 2H; δ 4.42, m, 1H; δ 3.33, m, 1H; δ 3.23, m, 2H; δ 3.10, m, 1H; δ 2.02, m, 1H; δ 1.85, m, 4H; δ 1.62, m, 1H | VI |
| 5-{3-[2-(diethylamino)ethoxy]phenyl}-N-piperidin-3-yl-2-{[(pyrazin-2-ylamino)carbonyl]amino}thiophene-3-carboxamide hydrochloride | 124 | 538 | 0.95(t, 6H), 1.52(m, 2H), 1.62(m, 4H), 2.52(m, 4H), 2.78(m, 4H), 3.00(m, 12H), 3.18(t, 2H), 4.05(t, 2H), 6.68(bs, 1H), 6.80(d, 1H), 7.10(m, 2H), 7.28(m, 2H), 7.82(s, 1H), 8.22(s, 1H), 8.28(s, 1H), 9.00(s, 1H) | VI |
| N-(2-aminoethyl)-5-(4-methoxyphenyl)-2-{[(pyrazin-2-ylamino)carbonyl]amino}thiophene-3-carboxamide | 125 | 413 | 8.53 s 1H, 8.31-8.33 m 1H, 8.13 d J=2.8Hz 1H, 7.42 d J=8.8Hz 2H, 7.38 s 1H, 6.85 d J=8.8Hz 2H, 3.72 s 3H. | VI |
| 5-{4-[2-(diethylamino)ethoxy]phenyl}-N-piperidin-3-yl-2-{[(pyrazin-2-ylamino)carbonyl]amino}thiophene-3-carboxamide | 126 | 538 | 0.95(t, 6H), 1.52(m, 2H), 1.79(m, 2H), 2.42(m, 4H), 2.70(m, 4H), 3.08(m, 2H), 3.98(m, 3H), 6.95(d, 2H), 7.48(d, 2H), 7.70(s, 1H), 8.28(d, 2H), 8.95(s, 1H) | VI |
| 5-(4-methoxyphenyl)-N-piperidin-4-yl-2-{[(pyrazin-2-ylamino)carbonyl]amino}thiophene-3-carboxamide | 127 | 453 |  | VI |
| tert-butyl 3-{[(5-{3-[2-(diethylamino)ethoxy]phenyl}-2-{[(pyrazin-2-ylamino)carbonyl]amino}-3-thienyl)carbonyl]amino}piperidine-1-carboxylate trifluoroacetate | 128 | 638 | 1.21(t, 6H), 1.32(s, 9H), 1.75(m, 1H), 1.92(m, 1H), 2.85(m, 1H), 3.20(m, 4H), 3.50(t, 2H), 3.80(m, 2H), 4.35(t, 2H), 6.90(d, 1H), 7.15(s, 1H) 7.25(d, 1H), 7.38(dxd, 1H), 7.76(s, 1H), 7.98(bs, 1H), 8.30(d, 2H), 8.90(s, 1H), 9.25(bs, 1H), 10.92(s, 1H) | VI |
| 5-{4-[2-(diethylamino)ethoxy]phenyl}-N-piperidin-4-yl-2-{[(pyrazin-2-ylamino)carbonyl]amino}thiophene-3-carboxamide | 129 | 538 | 0.95(t, 6H), 1.52(m, 2H), 1.79(m, 2H), 2.42(m, 4H), 2.70(m, 4H), 3.08(m, 2H), 3.98(m, 3H), 6.95(d, 2H), 7.48(d, 2H), 7.70(s, 1H), 8.28(d, 2H), 8.95(s, 1H) | VI |
| 5-(4-methoxyphenyl)-2-{[(pyrazin-2-ylamino)carbonyl]amino}-N-[(3S)-pyrrolidin-3-yl]thiophene-3-carboxamide | 130 | 439 |  | VI |
| N-[3-(1,4-diazepan-1-ylcarbonyl)-5-(4-methoxyphenyl)-2-thienyl]-N'-pyrazin-2-ylurea | 131 | 453 | 8.47 s 1H, 8.14-8.25 m 2H, 7.43 d J=8.8Hz 2H, 7.06 s 1H, 7.85 d J=8.8Hz 2H, 3.90 bs 2H, 3.79 t J=6.0Hz 2H, 3.72 s 3H, 3.40 bs 2H, 2.10 bs 2H. | VI |

TABLE 1-continued

| IUPAC Name | Ex. | LCMS (M+1, ES or APCI detection) | $^1$H NMR (d$_6$-DMSO unless stated otherwise) | Synthesis Method (Scheme) |
|---|---|---|---|---|
| N-[3-[(3-aminopyrrolidin-1-yl)carbonyl]-5-(4-methoxyphenyl)-2-thienyl]-N'-pyrazin-2-ylurea | 132 | 439 | 11.97 bs 1H, 10.72 s 1H, 8.79 s 1H, 8.22-8.26 m 2H, 7.50 d J=8.6Hz 2H, 8.04 bs 2H, 7.31 s 1H, 7.20-7.25 m 2H, 7.08 d J=8.3Hz 1H, 7.00 t J=7.2Hz 1H, 6.92 d J=8.6Hz 2H3.72 s 3H, 2.11-2.19 m 1H, 3.80 bs 2H, 3.64 bs 2H. | VI |
| tert-butyl 4-{[(5-(4-methoxyphenyl)-2-{[(pyrazin-2-ylamino)carbonyl]amino}-3-thienyl)carbonyl]amino}piperidine-1-carboxylate | 133 | 553 | | VI |
| tert-butyl 3-{[(5-{4-[2-(diethylamino)ethoxy]phenyl}-2-{[(pyrazin-2-ylamino)carbonyl]amino}-3-thienyl)carbonyl]amino}piperidine-1-carboxylate | 134 | 638 | 1.18(t, 6H), 1.32(s, 9H), 1.72(m, 1H), 1.90(m, 1H), 2.85(m, 1H), 3.21(m, 4H), 3.50(t, 2H), 3.80(m, 2H), 4.30(t, 2H), 7.05(d, 2H), 7.52(d, 2H), 7.76(s, 1H), 7.92(bs, 1H), 8.30(d, 2H), 8.90(s, 1H), 9.25(bs, 1H), 10.90(s, 1H) | VI |
| 5-[4-(2-diethylamino-ethoxy)-phenyl]-2-(3-hydroxy-urea)-thiophene-3-carboxylic acid-(S)-piperidin-3-ylamide | 136 | 476 | δ 1.17-1.40(m, 6H) 1.54-1.81(m, 2H) 1.84-2.07(m, 2H) 2.76-2.99(m, 2H) 3.05-3.25(m, 4H) 3.41-3.61(m, 4H) 3.73-3.88(m, 1H) 4.29-4.42(m, 1H) 4.40-4.64(m, 1H) 5.86(s, 1H) 7.07(d, J=8.48Hz, 2H) 7.55(d, J=8.48Hz, 2H) 7.82(s, 1H) 9.44(s, 1H) 9.65(s, 1H); | VII |
| 2-[(aminocarbonyl)amino]-N-[(3S)-azepan-3-yl]-5-(3-methoxyphenyl)thiophene-3-carboxamide | 137 | 389 | 10.90(s, 1H), 9.21(s, 1H), 9.01(s, 1H), 8.29(d, 1H), 7.93(s, 1H), 7.29(t, 1H), 7.11(d, 2H), 7.03(s, 1H), 6.83(d, 1H), 4.33(s, 1H), 3.81(s, 3H), 3.20(m, 4H), 2.00(m, 1H), 1.84(m, 4H), 1.56(m, 1H). | VIII |
| 2-[(aminocarbonyl)amino]-5-(2-hydroxyphenyl)-N-[(3S)-piperidin-3-yl]thiophene-3-carboxamide | 138 | 361 | δ 10.85(s, 1H), 10.13(s, 1H), 9.29(d, 2H), 8.31(d, 1H), 7.92(s, 1H), 7.63(dd, 1H), 7.05(td, 1H), 6.94(dd, 1H), 6.82(td, 1H), 6.91(brs, 2H), 4.21(brs, 1H), 3.26(dd, 2H), 2.89(m, 2H), 1.88-1.618(m, 4H). | VIII |
| 2-[(aminocarbonyl)amino]-5-(3-methoxyphenyl)-N-[(3S)-piperidin-3-yl]thiophene-3-carboxamide | 139 | 375 | 10.94(s, 1H), 9.41(s, 1H), 9.19(s, 1H), 8.47(d, 1H), 8.11(s, 1H), 7.30(t, 1H), 7.15(d, 1H), 7.05(br, 2H), 6.84(d, 1H), 4.25(s, 1H), 3.82(s, 3H), 3.29(d, 1H), 3.12(d, 1H), 2.97(m, 2H), 1.92(d, 2H), 1.69(m, 2H). | VIII |
| 2-[(aminocarbonyl)amino]-5-[2-(benzyloxy)phenyl]-N-[(3S)-piperidin-3-yl]thiophene-3-carboxamide | 140 | 451 | δ 10.8(s, 1H), 8.63(brs, 2H), 8.04(d, 1H), 7.79(s, 1H), 7.63(d, 1H), 7.55(d, 2H), 7.38(t, 2H), 7.31(t, 1H), 7.23(t, 1H), 7.20(t, 1H), 7.02(t, 1H), 6.95(m, 2H), 5.28(s, 2H), 4.15(m, 1H), 3.24(m, 1H), 2.85(m, 2H), 1.90-1.58(m, 5H). | VIII |

TABLE 2

| Structure | IUPAC Name | M.W. (g/mol) | Ex. |
|---|---|---|---|
| 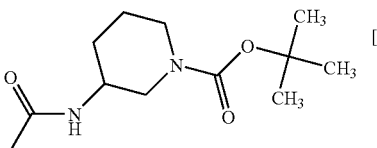 | tert-butyl 3-{[(2-[(aminocarbonyl)amino]-5-{4-[2-(diethylamino)ethoxy]-phenyl}-3-thienyl)carbonyl]-amino}piperidine-1-carboxylate trifluoroacetate | 559.7 | 1 |
| 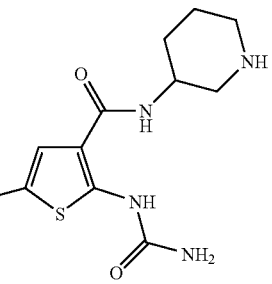 | 2-[(aminocarbonyl)amino]-5-{4-[2-(diethylamino)ethoxy]-phenyl}-N-piperidin-3-ylthiophene-3-carboxamide trifluoroacetate | 459.6 | 2 |
| 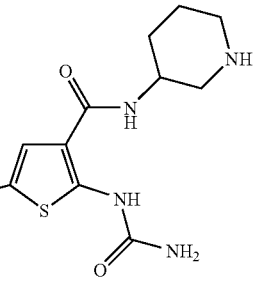 | 2-[(aminocarbonyl)amino]-5-{3-[2-(diethylamino)ethoxy]-phenyl}-N-piperidin-3-ylthiophene-3-carboxamide trifluoroacetate | 459.6 | 3 |
| 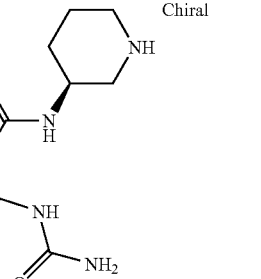 | 2-[(aminocarbonyl)amino]-5-(4-methoxyphenyl)-N-[(3S)-piperidin-3-yl]thiophene-3-carboxamide | 374.5 | 4 |
| 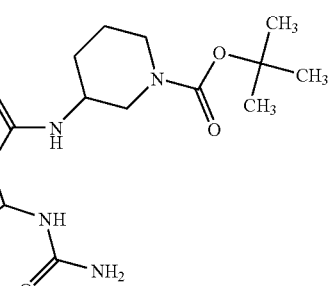 | tert-butyl 3-{[(2-[(aminocarbonyl)amino]-5-{3-[2-(diethylamino)ethoxy]-phenyl}-3-thienyl)carbonyl]-amino}piperidine-1-carboxylate trifluoroacetate | 559.7 | 5 |

TABLE 2-continued

| Structure | IUPAC Name | M.W. (g/mol) | Ex. |
|---|---|---|---|
| 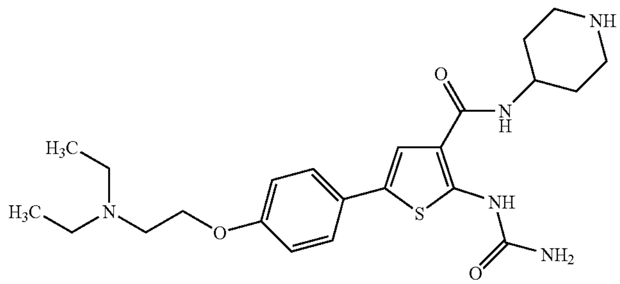 | 2-[(aminocarbonyl)amino]-5-{4-[2-(diethylamino)ethoxy]-phenyl}-N-piperidin-4-ylthiophene-3-carboxamide | 459.6 | 6 |
| Chiral | 2-[(aminocarbonyl)amino]-N-[(3R)-azepan-3-yl]-5-(4-methoxyphenyl)thiophene-3-carboxamide | 388.5 | 7 |
| 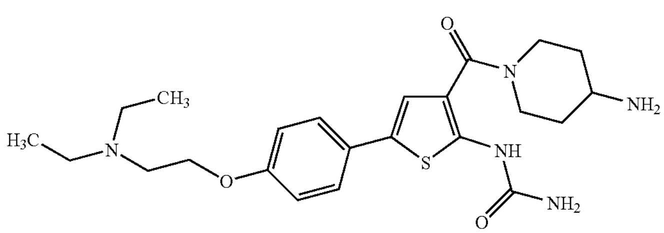 | N-(3-[(4-aminopiperidin-1-yl)-carbonyl]-5-{4-[2-(diethyl-amino)ethoxy]phenyl}-2-thienyl)urea trifluoroacetate | 459.6 | 8 |
| 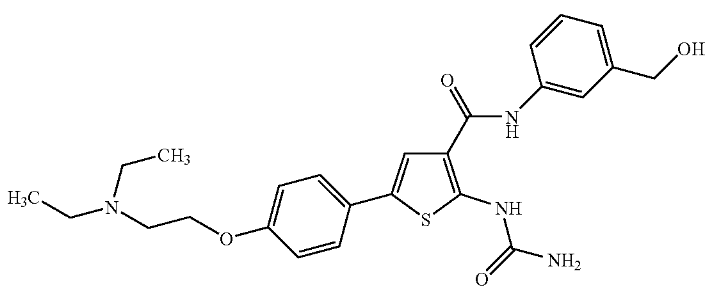 | 2-[(aminocarbonyl)amino]-5-{4-[2-(diethylamino)ethoxy]-phenyl}-N-[3-(hydroxy-methyl)phenyl]thiophene-3-carboxamide trifluoroacetate (salt) | 482.6 | 9 |
| 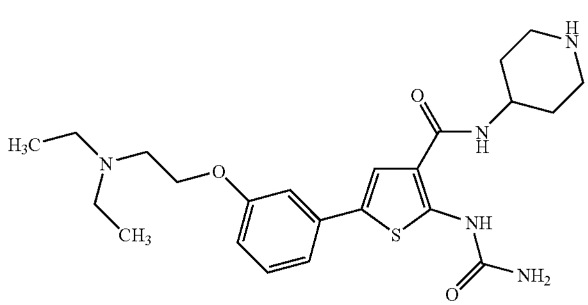 | 2-[(aminocarbonyl)amino]-5-{3-[2-(diethylamino)ethoxy]-phenyl}-N-piperidin-4-ylthiophene-3-carboxamide trifluoroacetate | 459.6 | 10 |

TABLE 2-continued

| Structure | IUPAC Name | M.W. (g/mol) | Ex. |
|---|---|---|---|
| | 2-[(aminocarbonyl)amino]-N-(2-aminoethyl)-5-(4-methoxyphenyl)thiophene-3-carboxamide | 334.4 | 11 |
| 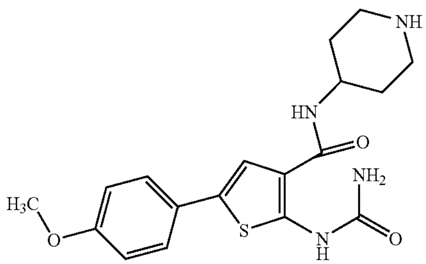 | 2-[(aminocarbonyl)amino]-5-(4-methoxyphenyl)-N-piperidin-4-ylthiophene-3-carboxamide | 374.5 | 12 |
| | 2-[(aminocarbonyl)amino]-5-{3-[2-(diethylamino)ethoxy]phenyl}-N-pyridin-3-ylthiophene-3-carboxamide trifluoroacetate | 453.6 | 13 |
| 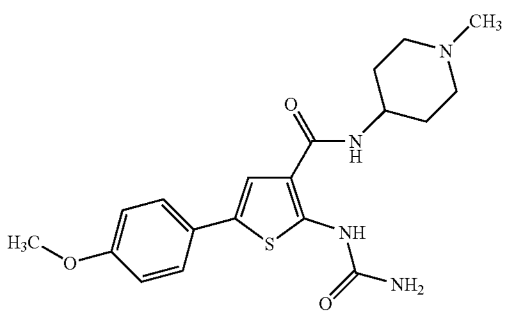 | 2-[(aminocarbonyl)amino]-5-(4-methoxyphenyl)-N-(1-methylpiperidin-4-yl)-thiophene-3-carboxamide | 388.5 | 14 |
| 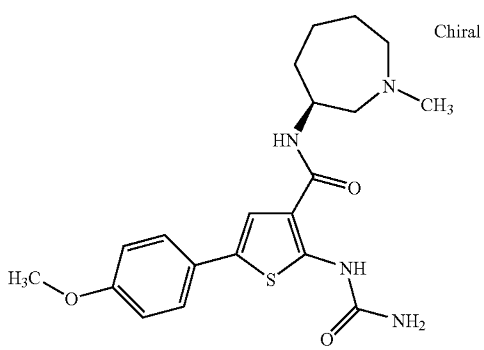 | 2-[(aminocarbonyl)amino]-5-(4-methoxyphenyl)-N-[(3S)-1-methylazepan-3-yl]thiophene-3-carboxamide hydrochloride | 402.5 | 15 |

TABLE 2-continued

| Structure | IUPAC Name | M.W. (g/mol) | Ex. |
|---|---|---|---|
| 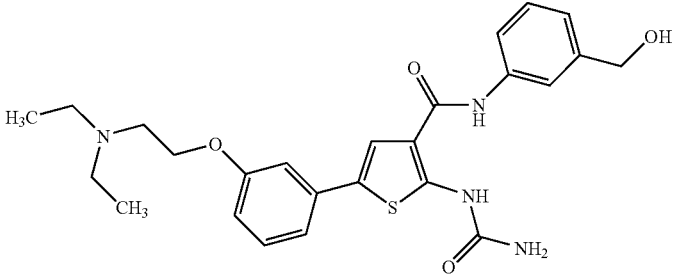 | 2-[(aminocarbonyl)amino]-5-{3-[2-(diethylamino)ethoxy]-phenyl}-N-[3-(hydroxy-methyl)phenyl]thiophene-3-carboxamide trifluoroacetate (salt) | 482.6 | 16 |
| 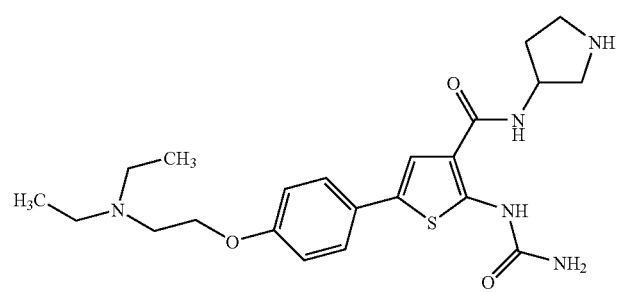 | 2-[(aminocarbonyl)amino]-5-{4-[2-(diethylamino)ethoxy]-phenyl}-N-pyrrolidin-3-ylthiophene-3-carboxamide trifluoroacetate | 445.6 | 17 |
| 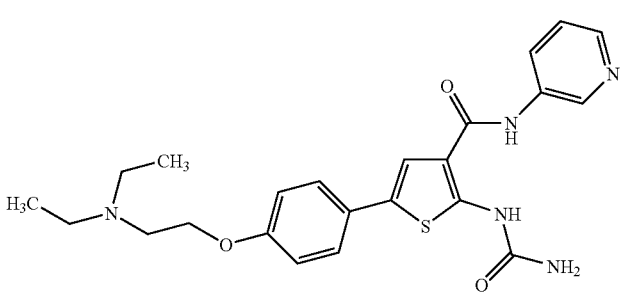 | 2-[(aminocarbonyl)amino]-5-{4-[2-(diethylamino)ethoxy]-phenyl}-N-pyridin-3-ylthiophene-3-carboxamide trifluoroacetate | 453.6 | 18 |
| 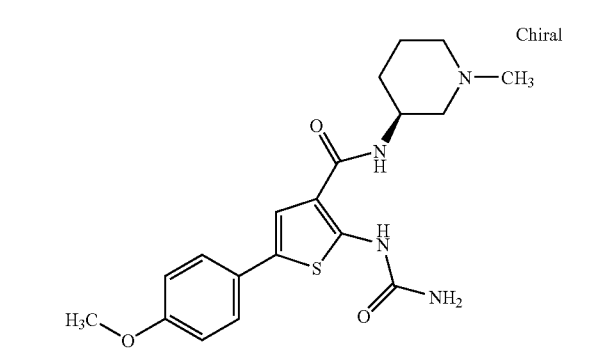 | 2-[(aminocarbonyl)amino]-5-(4-methoxyphenyl)-N-[(3S)-1-methylpiperidin-3-yl]-thiophene-3-carboxamide hydrochloride | 388.5 | 19 |
| 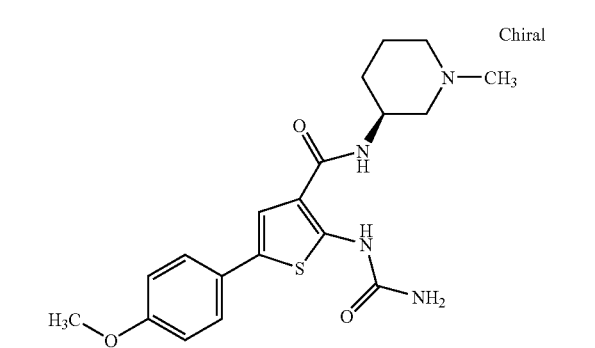 | 2-[(aminocarbonyl)amino]-5-{3-[2-(diethylamino)ethoxy]-phenyl}-N-pyrrolidin-3-ylthiophene-3-carboxamide trifluoroacetate | 445.6 | 20 |

TABLE 2-continued

| Structure | IUPAC Name | M.W. (g/mol) | Ex. |
|---|---|---|---|
| 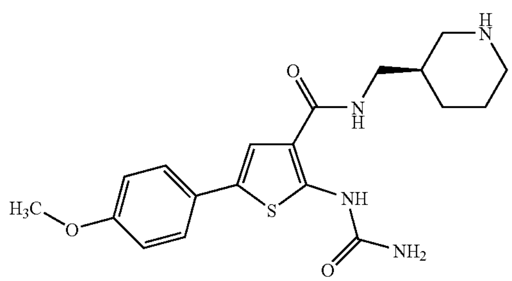 | 2-[(aminocarbonyl)amino]-5-(4-methoxyphenyl)-N-[(3R)-piperidin-3-ylmethyl]-thiophene-3-carboxamide | 388.5 | 21 |
| 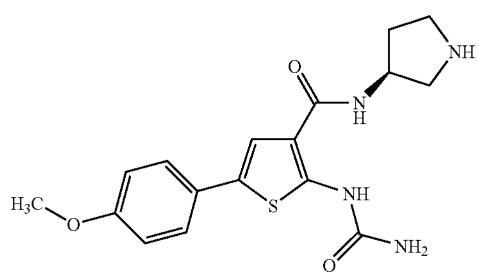 | 2-[(aminocarbonyl)amino]-5-(4-methoxyphenyl)-N-[(3S)-pyrrolidin-3-yl]thiophene-3-carboxamide | 360.4 | 22 |
| 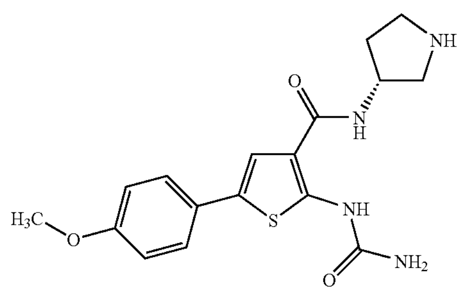 | 2-[(aminocarbonyl)amino]-5-(4-methoxyphenyl)-N-[(3R)-pyrrolidin-3-yl]thiophene-3-carboxamide | 360.4 | 23 |
| 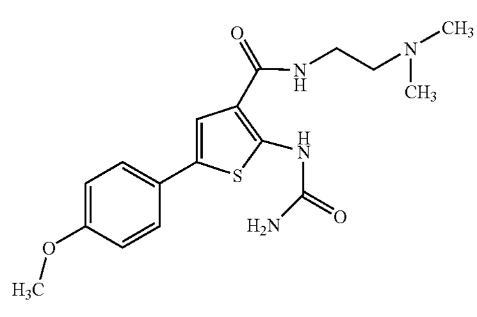 | 2-[(aminocarbonyl)amino]-N-[2-(dimethylamino)ethyl]-5-(4-methoxyphenyl)thiophene-3-carboxamide | 362.4 | 24 |
| 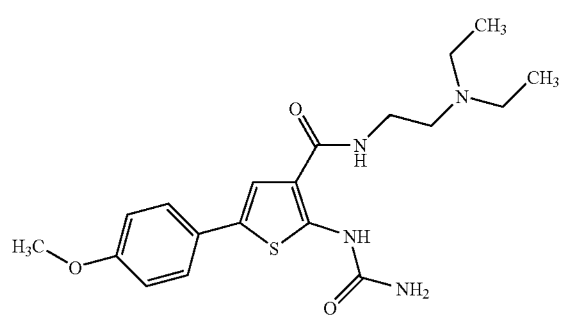 | 2-[(aminocarbonyl)amino]-N-[2-(diethylamino)ethyl]-5-(4-methoxyphenyl)thiophene-3-carboxamide | 390.5 | 25 |

TABLE 2-continued

| Structure | IUPAC Name | M.W. (g/mol) | Ex. |
|---|---|---|---|
| 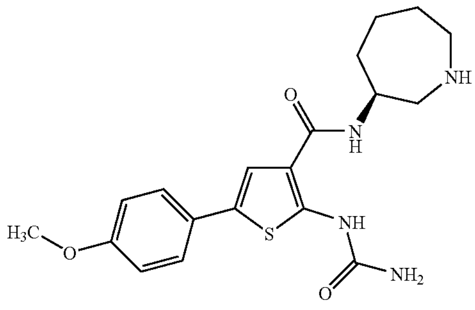 | 2-[(aminocarbonyl)amino]-N-[(3S)-azepan-3-yl]-5-(4-methoxyphenyl)thiophene-3-carboxamide hydrochloride | 388.5 | 26 |
| 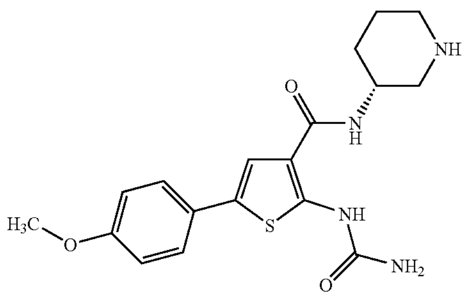 | 2-[(aminocarbonyl)amino]-5-(4-methoxyphenyl)-N-[(3R)-piperidin-3-yl]thiophene-3-carboxamide | 374.5 | 27 |
| 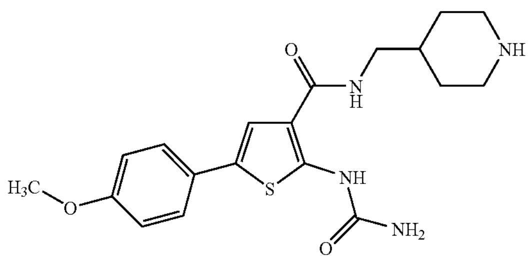 | 2-[(aminocarbonyl)amino]-5-(4-methoxyphenyl)-N-(piperidin-4-ylmethyl)-thiophene-3-carboxamide | 388.5 | 28 |
| 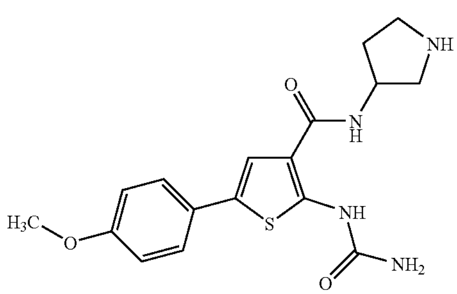 | 2-[(aminocarbonyl)amino]-5-(4-methoxyphenyl)-N-pyrrolidin-3-ylthiophene-3-carboxamide | 360.4 | 29 |
| 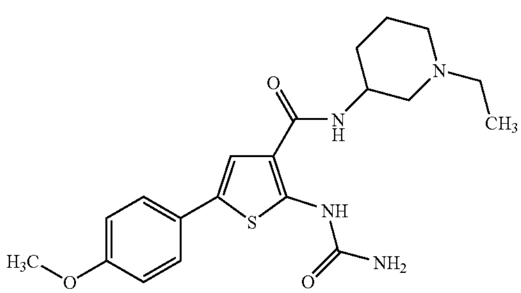 | 2-[(aminocarbonyl)amino]-N-(1-ethylpiperidin-3-yl)-5-(4-methoxyphenyl)thiophene-3-carboxamide hydrochloride | 402.5 | 30 |

TABLE 2-continued

| Structure | IUPAC Name | M.W. (g/mol) | Ex. |
|---|---|---|---|
| 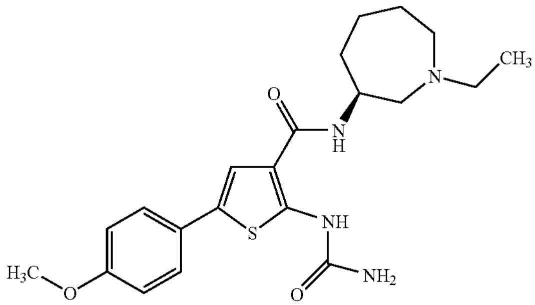 | 2-[(aminocarbonyl)amino]-N-[(3S)-1-ethylazepan-3-yl]-5-(4-methoxyphenyl)thiophene-3-carboxamide hydrochloride | 416.5 | 31 |
| 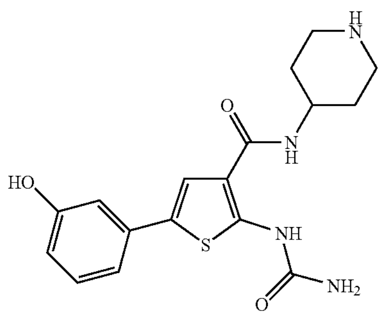 | 2-[(aminocarbonyl)amino]-5-(3-hydroxyphenyl)-N-piperidin-4-ylthiophene-3-carboxamide | 360.4 | 32 |
| 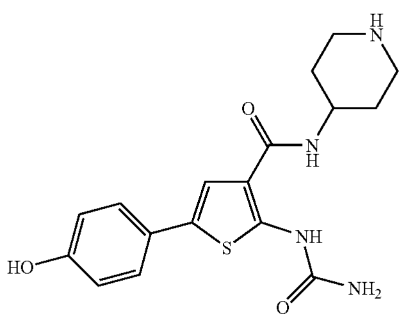 | 2-[(aminocarbonyl)amino]-5-(4-hydroxyphenyl)-N-piperidin-4-ylthiophene-3-carboxamide | 360.4 | 33 |
| 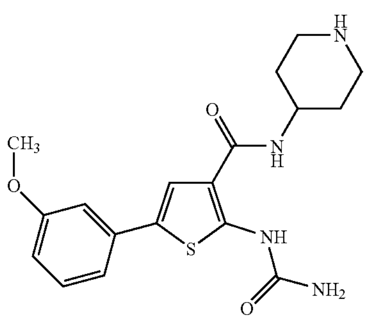 | 2-[(aminocarbonyl)amino]-5-(3-methoxyphenyl)-N-piperidin-4-ylthiophene-3-carboxamide | 374.5 | 34 |
| | tert-butyl (3S)-3-({[2-[(aminocarbonyl)amino]-5-(4-methoxyphenyl)-3-thienyl]carbonyl}amino)pyrrolidine-1-carboxylate | 460.6 | 35 |

TABLE 2-continued

| Structure | IUPAC Name | M.W. (g/mol) | Ex. |
|---|---|---|---|
| 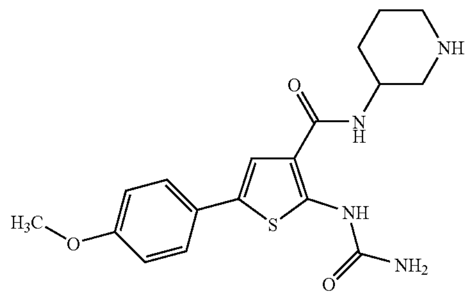 | 2-[(aminocarbonyl)amino]-5-(4-methoxyphenyl)-N-piperidin-3-ylthiophene-3-carboxamide | 374.5 | 36 |
| 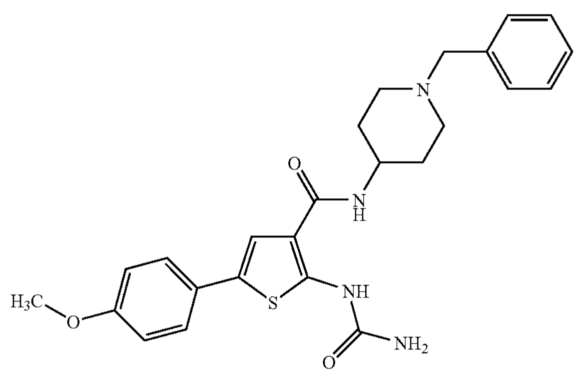 | 2-[(aminocarbonyl)amino]-N-(1-benzylpiperidin-4-yl)-5-(4-methoxyphenyl)thiophene-3-carboxamide | 464.6 | 37 |
| 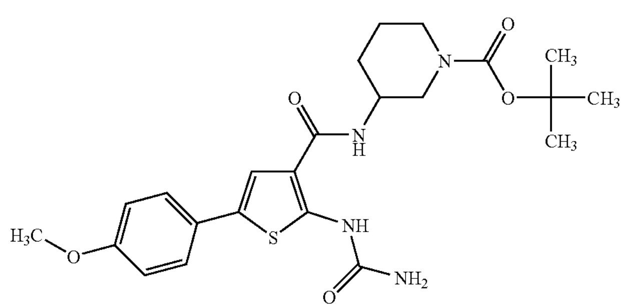 | tert-butyl 3-({[2-[(amino-carbonyl)amino]-5-(4-methoxyphenyl)-3-thienyl]-carbonyl}amino)piperidine-1-carboxylate | 474.6 | 38 |
| 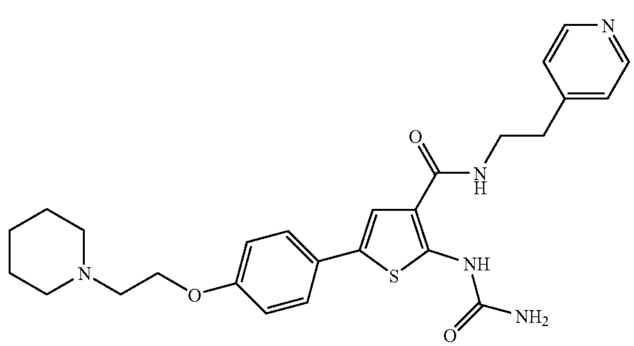 | 2-[(aminocarbonyl)amino]-5-[4-(2-piperidin-1-ylethoxy)phenyl]-N-(2-pyridin-4-ylethyl)thiophene-3-carboxamide | 493.6 | 39 |

TABLE 2-continued

| Structure | IUPAC Name | M.W. (g/mol) | Ex. |
|---|---|---|---|
| 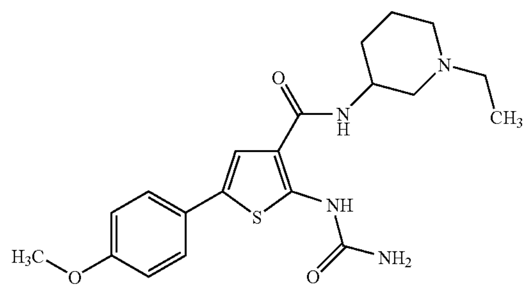 | 2-[(aminocarbonyl)amino]-5-[4-(2-piperidin-1-ylethoxy)phenyl]-N-(2-pyridin-4-ylethyl)thiophene-3-carboxamide | 450.6 | 40 |
| 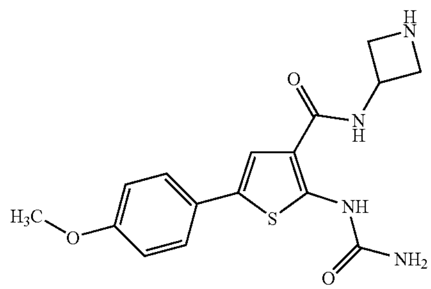 | 2-[(aminocarbonyl)amino]-N-azetidin-3-yl-5-(4-methoxyphenyl)thiophene-3-carboxamide | 346.4 | 41 |
| Chiral | 2-[(aminocarbonyl)amino]-5-(4-methoxyphenyl)-N-[(2S)-pyrrolidin-2-ylmethyl]-thiophene-3-carboxamide | 374.5 | 42 |
| 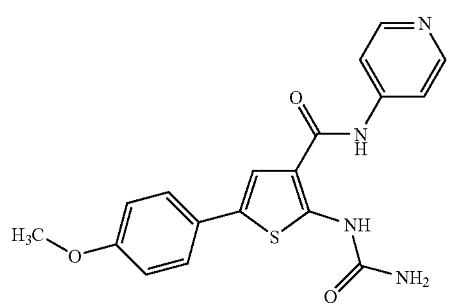 | 2-[(aminocarbonyl)amino]-5-(4-methoxyphenyl)-N-pyridin-4-ylthiophene-3-carboxamide | 368.4 | 43 |
| 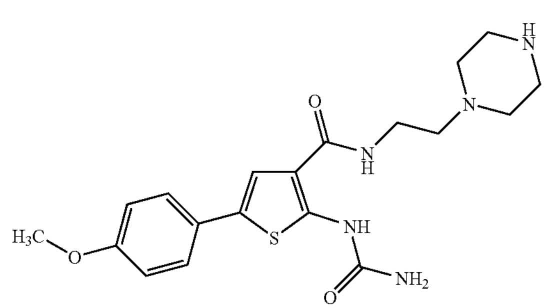 | 2-[(aminocarbonyl)amino]-5-(4-methoxyphenyl)-N-(2-piperazin-1-ylethyl)thiophene-3-carboxamide | 403.5 | 44 |

TABLE 2-continued

| Structure | IUPAC Name | M.W. (g/mol) | Ex. |
|---|---|---|---|
| 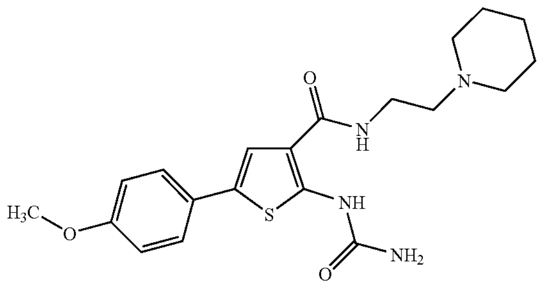 | 2-[(aminocarbonyl)amino]-5-(4-methoxyphenyl)-N-(2-piperidin-1-ylethyl)thiophene-3-carboxamide | 402.5 | 45 |
| 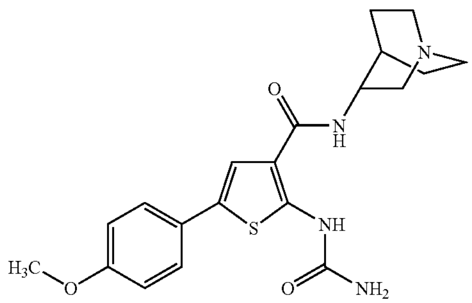 | 2-[(aminocarbonyl)amino]-N-1-azabicyclo[2.2.2]oct-3-yl-5-(4-methoxyphenyl)thiophene-3-carboxamide | 400.5 | 46 |
| 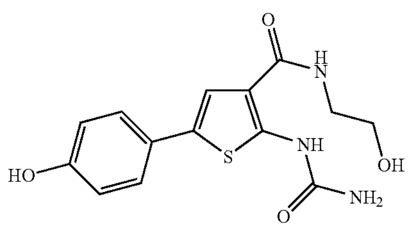 | 2-[(aminocarbonyl)amino]-N-(2-hydroxyethyl)-5-(4-hydroxyphenyl)thiophene-3-carboxamide | 321.4 | 48 |
| 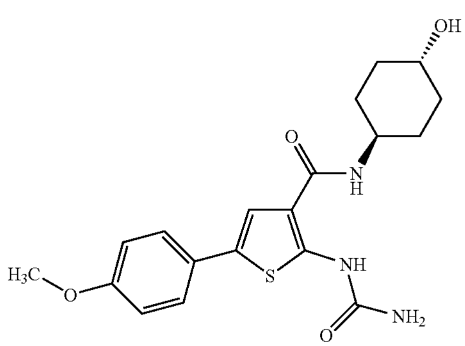 | 2-[(aminocarbonyl)amino]-N-(trans-4-hydroxycyclohexyl)-5-(4-methoxyphenyl)-thiophene-3-carboxamide | 389.5 | 49 |
| 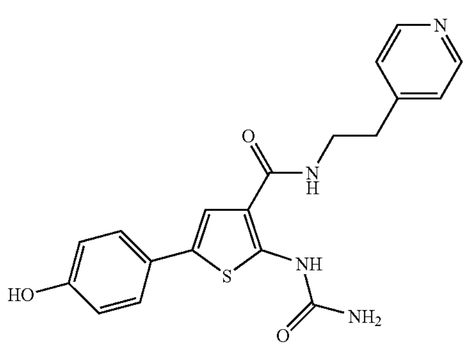 | 2-[(aminocarbonyl)amino]-5-(4-hydroxyphenyl)-N-(2-pyridin-4-ylethyl)thiophene-3-carboxamide | 382.4 | 50 |

TABLE 2-continued

| Structure | IUPAC Name | M.W. (g/mol) | Ex. |
|---|---|---|---|
| 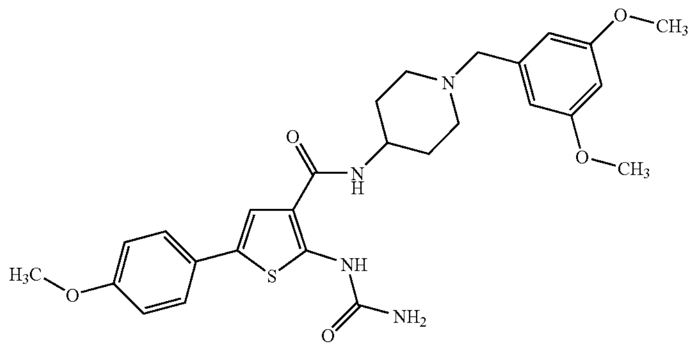 | 2-[(aminocarbonyl)amino]-5-(4-methoxyphenyl)-N-(2-piperazin-1-ylethyl)thiophene-3-carboxamide | 524.6 | 52 |
| 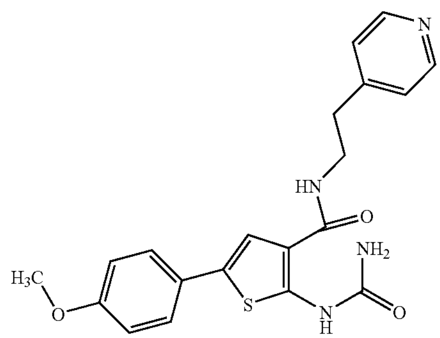 | 2-[(aminocarbonyl)amino]-5-(4-methoxyphenyl)-N-(2-pyridin-4-ylethyl)thiophene-3-carboxamide | 396.5 | 54 |
| 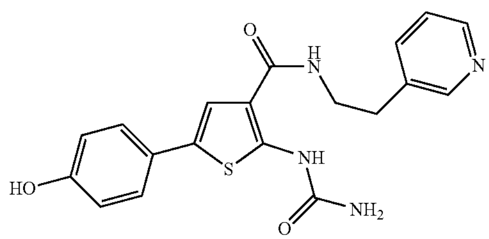 | 2-[(aminocarbonyl)amino]-5-(4-hydroxyphenyl)-N-(2-pyridin-3-ylethyl)thiophene-3-carboxamide | 382.4 | 55 |
| 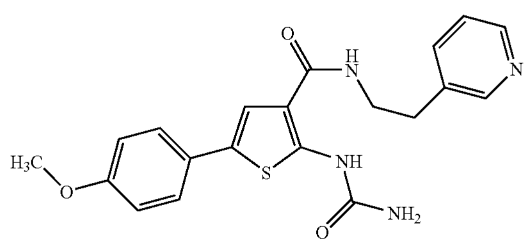 | 2-[(aminocarbonyl)amino]-5-(4-methoxyphenyl)-N-(2-pyridin-3-ylethyl)thiophene-3-carboxamide | 396.5 | 56 |
| 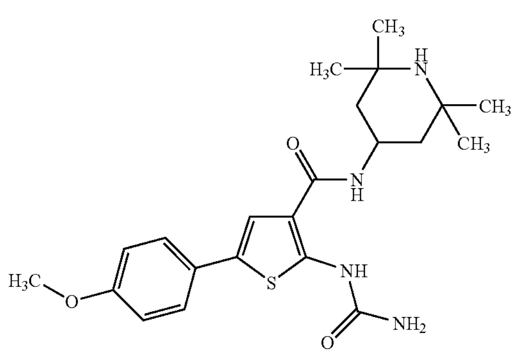 | 2-[(aminocarbonyl)amino]-5-(4-methoxyphenyl)-N-(2,2,6,6-tetramethylpiperidin-4-yl)thiophene-3-carboxamide | 430.6 | 58 |

TABLE 2-continued

| Structure | IUPAC Name | M.W. (g/mol) | Ex. |
|---|---|---|---|
| 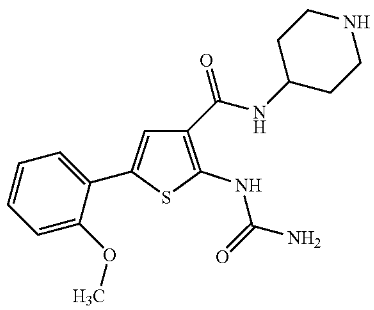 | 2-[(aminocarbonyl)amino]-5-(2-methoxyphenyl)-N-piperidin-4-ylthiophene-3-carboxamide | 374.5 | 59 |
| 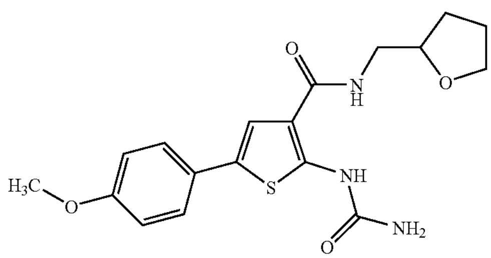 | 2-[(aminocarbonyl)amino]-5-(4-methoxyphenyl)-N-(tetra-hydrofuran-2-ylmethyl)-thiophene-3-carboxamide | 375.4 | 60 |
| Chiral | tert-butyl (3R)-3-({[2-[(aminocarbonyl)amino]-5-(4-methoxyphenyl)-3-thienyl]-carbonyl}amino)piperidine-1-carboxylate | 474.6 | 62 |
| 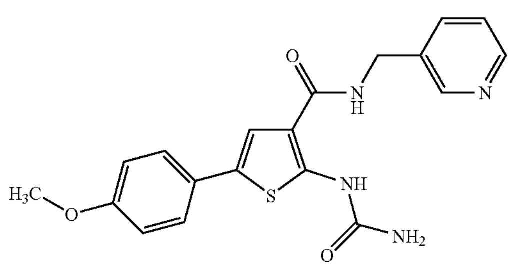 | 2-[(aminocarbonyl)amino]-5-(4-methoxyphenyl)-N-(pyridin-3-ylmethyl)-thiophene-3-carboxamide | 382.4 | 63 |
| 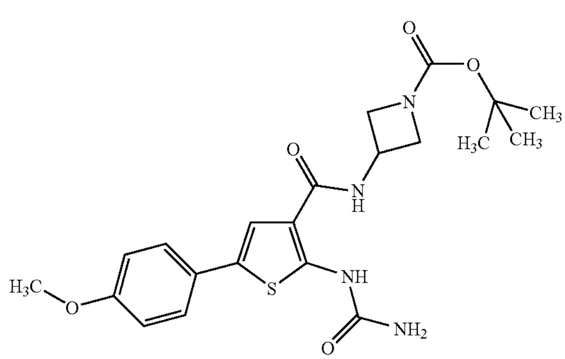 | tert-butyl 3-({[2-[(amino-carbonyl)amino]-5-(4-methoxyphenyl)-3-thienyl]-carbonyl}amino)azetidine-1-carboxylate | 446.5 | 64 |

TABLE 2-continued

| Structure | IUPAC Name | M.W. (g/mol) | Ex. |
|---|---|---|---|
| 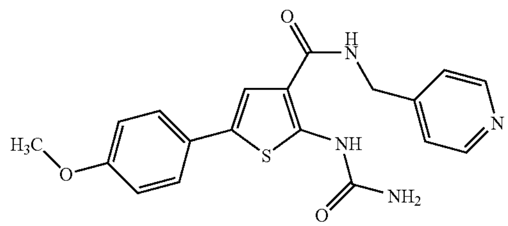 | 2-[(aminocarbonyl)amino]-5-(4-methoxyphenyl)-N-(pyridin-4-ylmethyl)-thiophene-3-carboxamide | 382.4 | 65 |
| 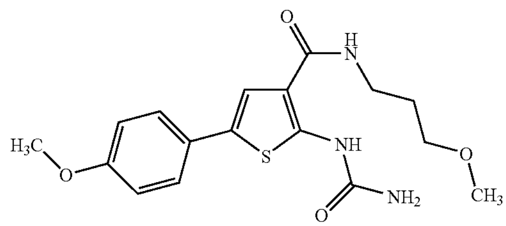 | 2-[(aminocarbonyl)amino]-5-(4-methoxyphenyl)-N-(3-methoxypropyl)thiophene-3-carboxamide | 363.4 | 67 |
| 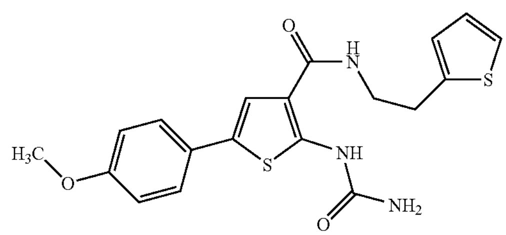 | 2-[(aminocarbonyl)amino]-5-(4-methoxyphenyl)-N-[2-(2-thienyl)ethyl]thiophene-3-carboxamide | 401.5 | 68 |
| 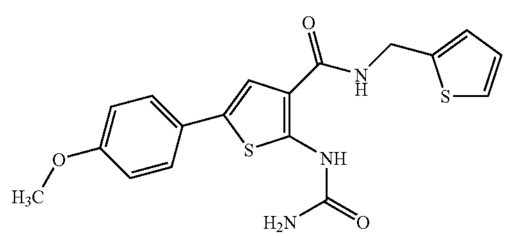 | 2-[(aminocarbonyl)amino]-5-(4-methoxyphenyl)-N-(2-thienylmethyl)thiophene-3-carboxamide | 387.5 | 69 |
| 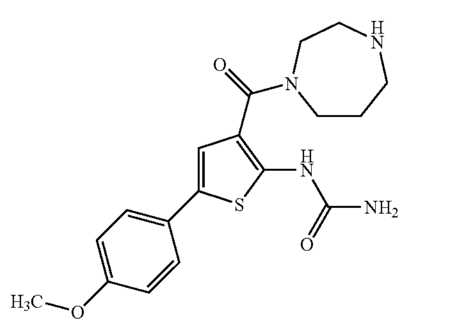 | N-[3-(1,4-diazepan-1-yl-carbonyl)-5-(4-methoxy-phenyl)-2-thienyl]urea | 374.5 | 70 |
| 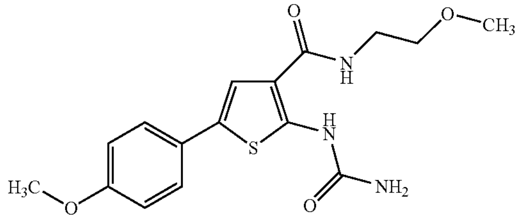 | 2-[(aminocarbonyl)amino]-N-(2-methoxyethyl)-5-(4-methoxyphenyl)thiophene-3-carboxamide | 349.4 | 71 |

TABLE 2-continued

| Structure | IUPAC Name | M.W. (g/mol) | Ex. |
|---|---|---|---|
| 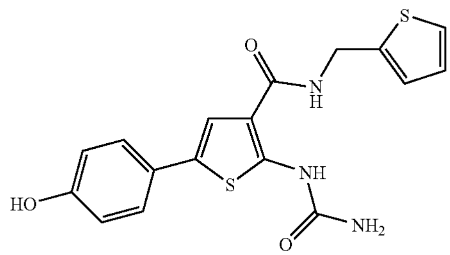 | 2-[(aminocarbonyl)amino]-5-(4-hydroxyphenyl)-N-(2-thienylmethyl)thiophene-3-carboxamide | 373.5 | 72 |
| | 2-[(aminocarbonyl)amino]-N-{2-[(2-furylmethyl)thio]ethyl}-5-(4-methoxyphenyl)-thiophene-3-carboxamide | 431.5 | 74 |
| 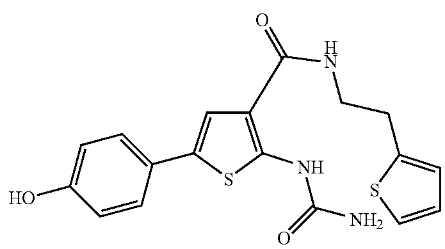 | 2-[(aminocarbonyl)amino]-5-(4-hydroxyphenyl)-N-[2-(2-thienyl)ethyl]thiophene-3-carboxamide | 387.5 | 75 |
| 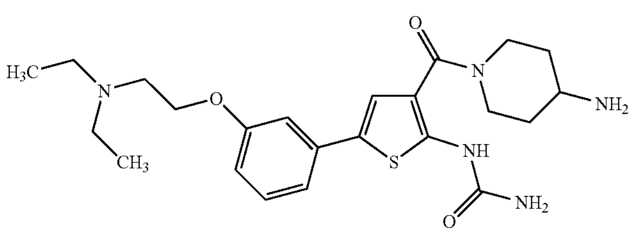 | N-(3-[(4-aminopiperidin-1-yl)-carbonyl]-5-{3-[2-(diethyl-amino)ethoxy]phenyl}-2-thienyl)urea trifluoroacetate | 459.6 | 76 |
| Chiral | 2-[(aminocarbonyl)amino]-5-(4-methoxyphenyl)-N-[(3R)-piperidin-3-ylmethyl]-thiophene-3-carboxamide | 388.5 | 77 |

TABLE 2-continued

| Structure | IUPAC Name | M.W. (g/mol) | Ex. |
|---|---|---|---|
| 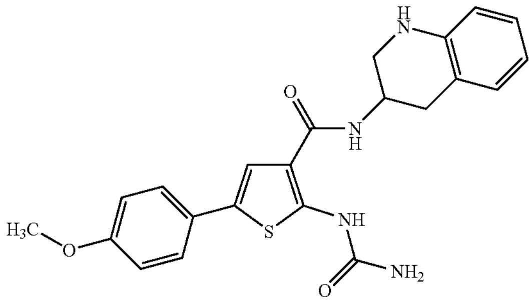 | 2-[(aminocarbonyl)amino]-5-(4-methoxyphenyl)-N-(1,2,3,4-tetrahydroquinolin-3-yl)thiophene-3-carboxamide | 422.5 | 78 |
| 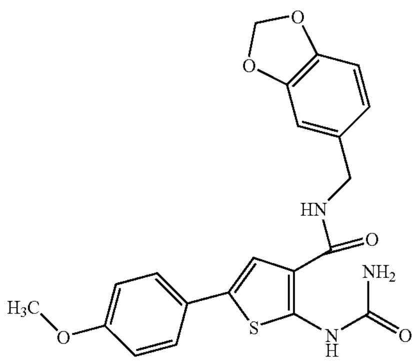 | 2-[(aminocarbonyl)amino]-N-(1,3-benzodioxol-5-ylmethyl)-5-(4-methoxyphenyl)-thiophene-3-carboxamide | 425.5 | 79 |
| 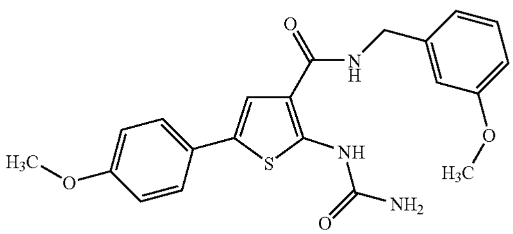 | 2-[(aminocarbonyl)amino]-N-(3-methoxybenzyl)-5-(4-methoxyphenyl)thiophene-3-carboxamide | 411.5 | 80 |
| 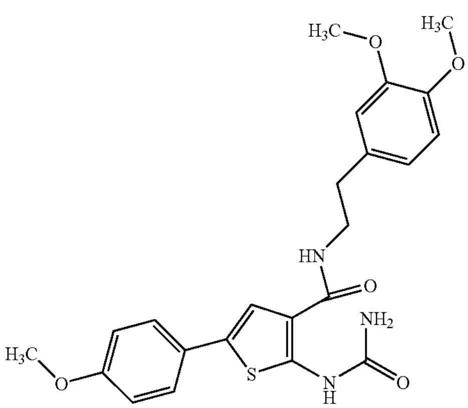 | 2-[(aminocarbonyl)amino]-N-[2-(3,4-dimethoxyphenyl)-ethyl]-5-(4-methoxyphenyl)-thiophene-3-carboxamide | 455.5 | 81 |
| 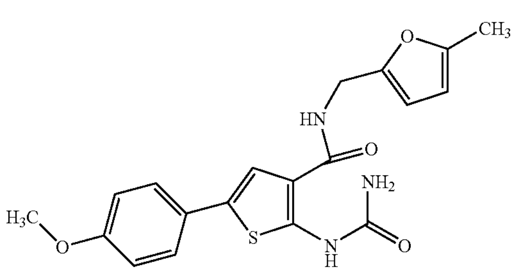 | 2-[(aminocarbonyl)amino]-5-(4-methoxyphenyl)-N-[(5-methyl-2-furyl)methyl]-thiophene-3-carboxamide | 385.4 | 84 |

TABLE 2-continued

| Structure | IUPAC Name | M.W. (g/mol) | Ex. |
|---|---|---|---|
| 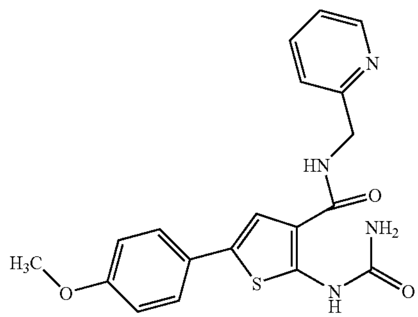 | 2-[(aminocarbonyl)amino]-5-(4-methoxyphenyl)-N-(pyridin-2-ylmethyl)-thiophene-3-carboxamide | 382.4 | 85 |
| 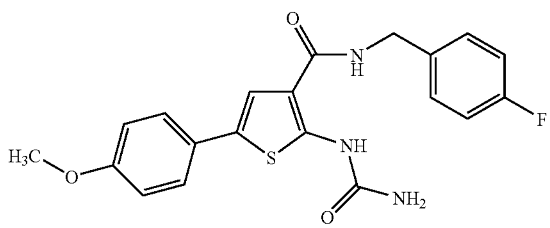 | 2-[(aminocarbonyl)amino]-N-(4-fluorobenzyl)-5-(4-methoxyphenyl)thiophene-3-carboxamide | 399.4 | 86 |
| 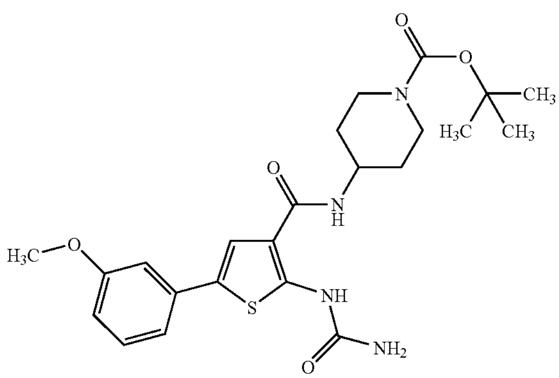 | tert-butyl 4-({[2-[(amino-carbonyl)amino]-5-(3-methoxyphenyl)-3-thienyl]-carbonyl}amino)piperidine-1-carboxylate | 474.6 | 88 |
| 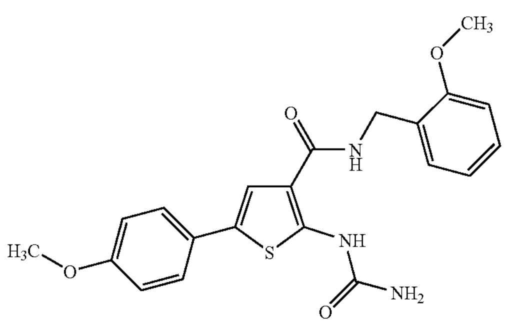 | 2-[(aminocarbonyl)amino]-N-(2-methoxybenzyl)-5-(4-methoxyphenyl)thiophene-3-carboxamide | 411.5 | 89 |
| 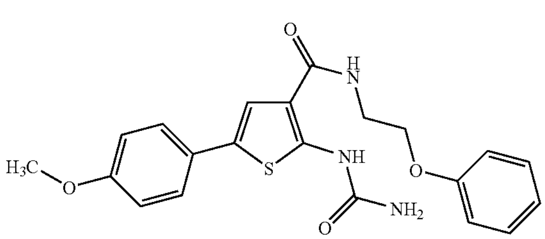 | 2-[(aminocarbonyl)amino]-5-(4-methoxyphenyl)-N-(2-phenoxyethyl)thiophene-3-carboxamide | 411.5 | 90 |

TABLE 2-continued

| Structure | IUPAC Name | M.W. (g/mol) | Ex. |
|---|---|---|---|
| 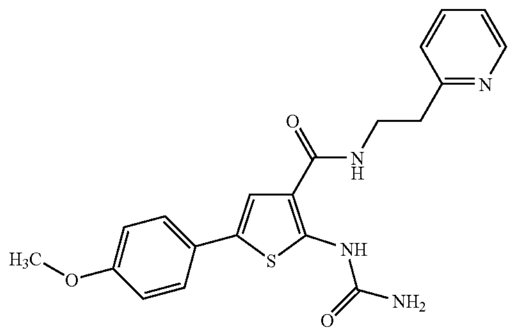 | 2-[(aminocarbonyl)amino]-5-(4-methoxyphenyl)-N-(2-pyridin-2-ylethyl)thiophene-3-carboxamide | 396.5 | 93 |
| 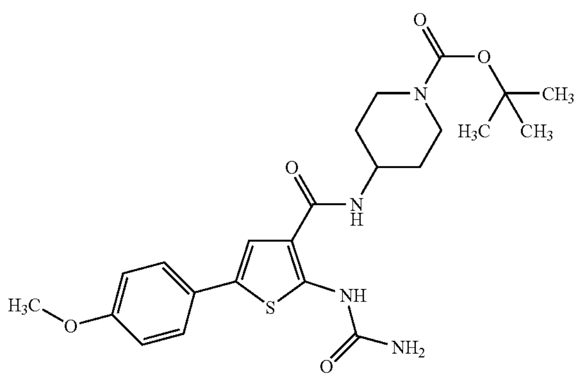 | tert-butyl 4-({[2-[(amino-carbonyl)amino]-5-(4-methoxyphenyl)-3-thienyl]-carbonyl}amino)piperidine-1-carboxylate | 474.6 | 94 |
| 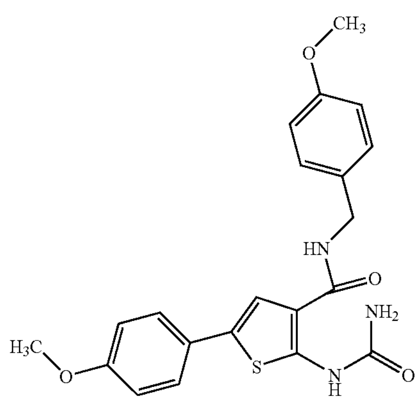 | 2-[(aminocarbonyl)amino]-N-(4-methoxybenzyl)-5-(4-methoxyphenyl)thiophene-3-carboxamide | 411.5 | 95 |
| 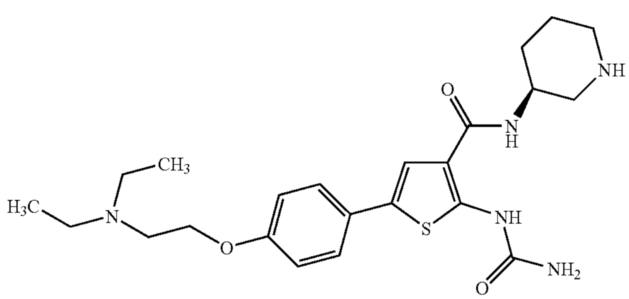 | 2-[(aminocarbonyl)amino]-5-{4-[2-(diethylamino)ethoxy]-phenyl}-N-[(3S)-piperidin-3-yl]thiophene-3-carboxamide trifluoroacetate | 459.6 | 110 |

TABLE 2-continued

| Structure | IUPAC Name | M.W. (g/mol) | Ex. |
|---|---|---|---|
| Chiral | 2-[(aminocarbonyl)amino]-5-{4-[2-(diethylamino)ethoxy]-phenyl}-N-[(3R)-piperidin-3-yl]thiophene-3-carboxamide trifluoroacetate | 459.6 | 111 |
| Chiral | tert-butyl (3S)-3-{[(2-[(aminocarbonyl)amino]-5-{4-[2-(diethylamino)ethoxy]-phenyl}-3-thienyl)carbonyl]-amino}piperidine-1-carboxylate trifluoroacetate | 559.7 | 112 |
| Chiral | 2-[(aminocarbonyl)amino]-N-[(3S)-azepan-3-yl]-5-{4-[2-(diethylamino)ethoxy]phenyl}-thiophene-3-carboxamide hydrochloride | 473.6 | 113 |
| Chiral | tert-butyl (3R)-3-{[(2-[(aminocarbonyl)amino]-5-{4-[2-(diethylamino)ethoxy]-phenyl}-3-thienyl)carbonyl]-amino}piperidine-1-carboxylate trifluoroacetate | 559.7 | 114 |
| Chiral | N-[3-{[(3S)-3-aminoazepan-1-yl]carbonyl}-5-(4-methoxy-phenyl)-2-thienyl]urea hydrochloride | 388.5 | 115 |

TABLE 2-continued

| Structure | IUPAC Name | M.W. (g/mol) | Ex. |
|---|---|---|---|
| 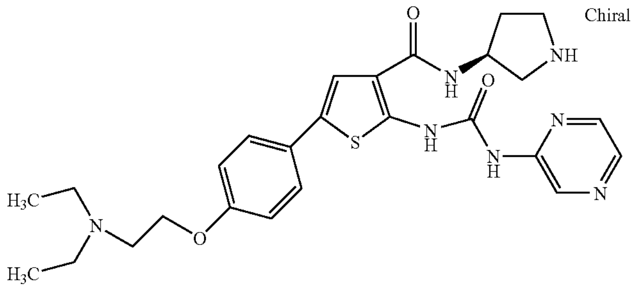 | 5-{4-[2-(diethylamino)-ethoxy]phenyl}-2-{[(pyrazin-2-ylamino)carbonyl]amino}-N-[(3S)-pyrrolidin-3-yl]-thiophene-3-carboxamide | 523.7 | 120 |
| 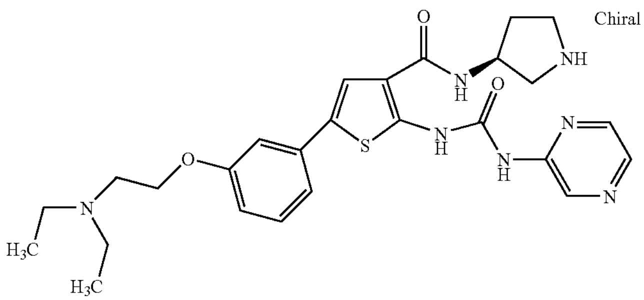 | 5-{3-[2-(diethylamino)ethoxy]-phenyl}-2-{[(pyrazin-2-ylamino)carbonyl]amino}-N-[(3S)-pyrrolidin-3-yl]-thiophene-3-carboxamide hydrochloride | 523.7 | 121 |
| 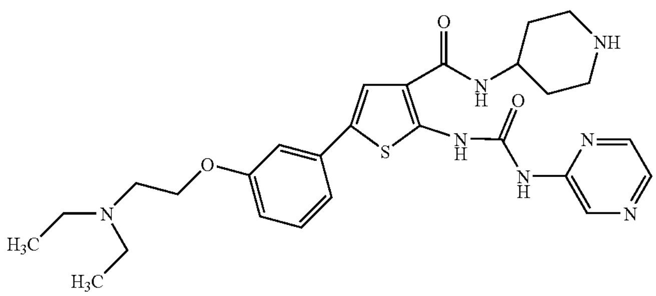 | 5-{3-[2-(diethylamino)ethoxy]-phenyl}-N-piperidin-4-yl-2-{[(pyrazin-2-ylamino)-carbonyl]amino}thiophene-3-carboxamide | 537.7 | 122 |
| 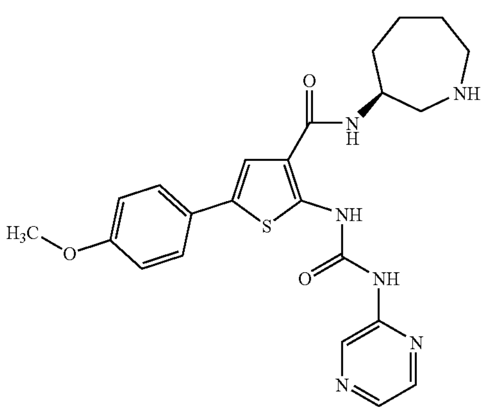 | N-[(3S)-azepan-3-yl]-5-(4-methoxyphenyl)-2-{[(pyrazin-2-ylamino)carbonyl]amino}-thiophene-3-carboxamide hydrochloride | 466.6 | 123 |
| 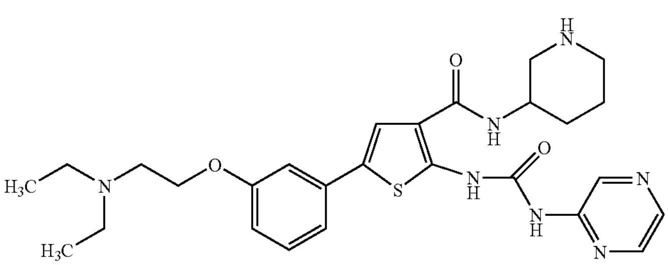 | 5-{3-[2-(diethylamino)ethoxy]-phenyl}-N-piperidin-3-yl-2-{[(pyrazin-2-ylamino)-carbonyl]amino}thiophene-3-carboxamide hydrochloride | 537.7 | 124 |

TABLE 2-continued

| Structure | IUPAC Name | M.W. (g/mol) | Ex. |
|---|---|---|---|
| 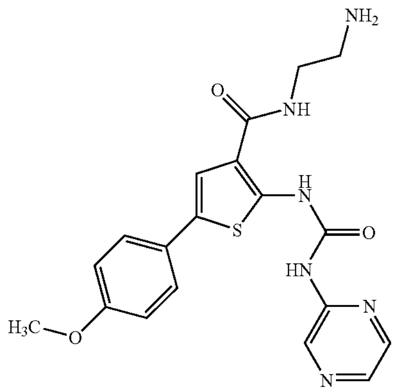 | N-(2-aminoethyl)-5-(4-methoxyphenyl)-2-{[(pyrazin-2-ylamino)carbonyl]amino}-thiophene-3-carboxamide | 412.5 | 125 |
| 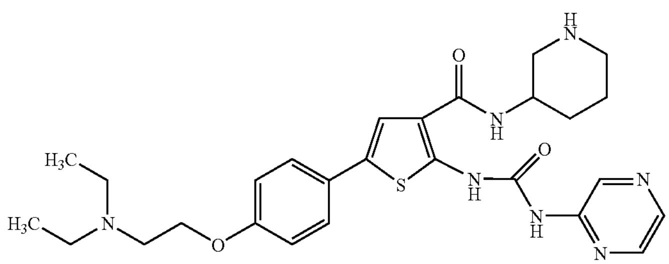 | 5-{4-[2-(diethylamino)ethoxy]-phenyl}-N-piperidin-3-yl-2-{[(pyrazin-2-ylamino)-carbonyl]amino}thiophene-3-carboxamide | 537.7 | 126 |
| 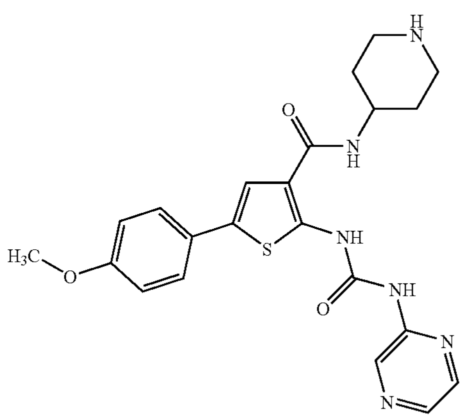 | 5-(4-methoxyphenyl)-N-piperidin-4-yl-2-{[(pyrazin-2-ylamino)carbonyl]amino}-thiophene-3-carboxamide | 452.5 | 127 |
| 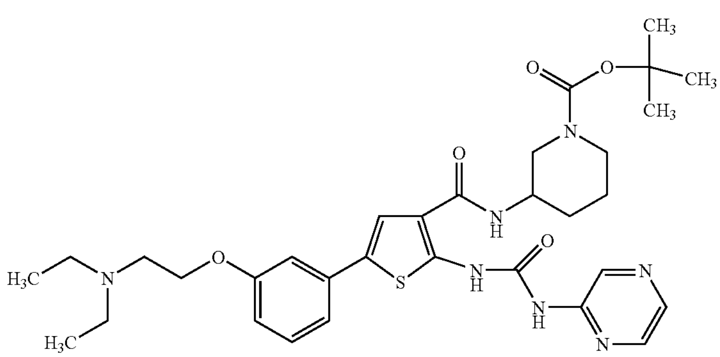 | tert-butyl 3-{[(5-{3-[2-(diethylamino)ethoxy]-phenyl}-2-{[(pyrazin-2-ylamino)carbonyl]amino}-3-thienyl)carbonyl]amino}-piperidine-1-carboxylate trifluoroacetate | 637.8 | 128 |

TABLE 2-continued

| Structure | IUPAC Name | M.W. (g/mol) | Ex. |
|---|---|---|---|
| 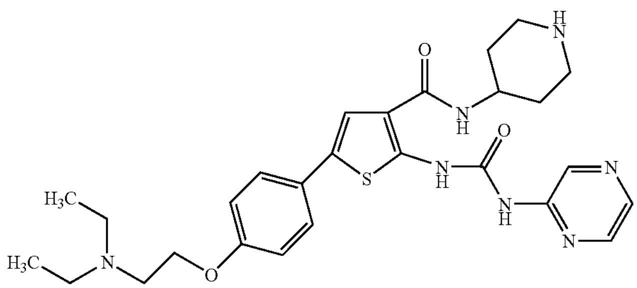 | 5-{4-[2-(diethylamino)ethoxy]-phenyl}-N-piperidin-4-yl-2-{[(pyrazin-2-ylamino)-carbonyl]amino}thiophene-3-carboxamide | 537.7 | 129 |
| Chiral | 5-(4-methoxyphenyl)-2-{[(pyrazin-2-ylamino)-carbonyl]amino}-N-[(3S)-pyrrolidin-3-yl]thiophene-3-carboxamide | 438.5 | 130 |
| 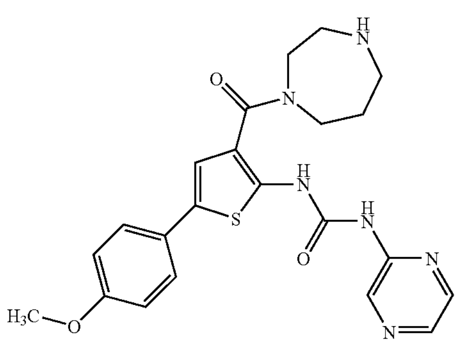 | N-[3-(1,4-diazepan-1-yl-carbonyl)-5-(4-methoxy-phenyl)-2-thienyl]-N'-pyrazin-2-ylurea | 452.5 | 131 |
| 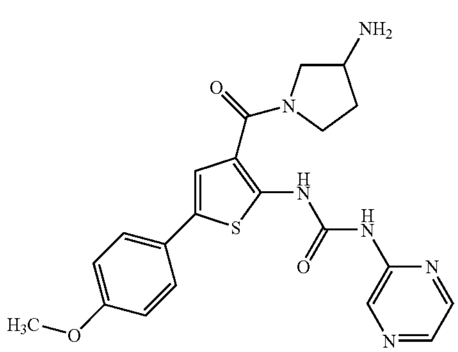 | N-[3-[(3-aminopyrrolidin-1-yl)carbonyl]-5-(4-methoxy-phenyl)-2-thienyl]-N'-pyrazin-2-ylurea | 438.5 | 132 |

TABLE 2-continued

| Structure | IUPAC Name | M.W. (g/mol) | Ex. |
|---|---|---|---|
| 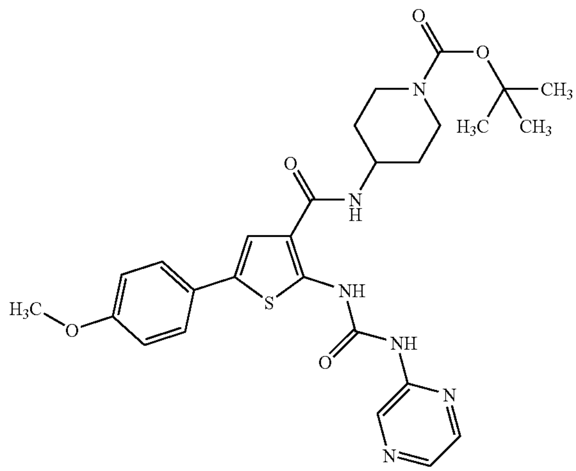 | tert-butyl 4-{[(5-(4-methoxy-phenyl)-2-{[(pyrazin-2-ylamino)carbonyl]amino}-3-thienyl)carbonyl]amino}-piperidine-1-carboxylate | 552.6 | 133 |
| 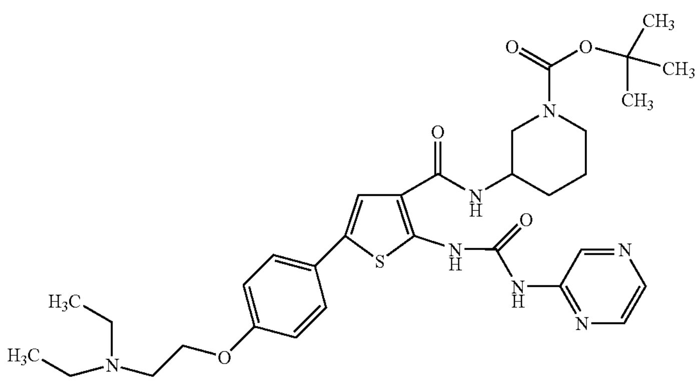 | tert-butyl 3-{[(5-{4-[2-(diethylamino)ethoxy]-phenyl}-2-{[(pyrazin-2-ylamino)carbonyl]amino}-3-thienyl)carbonyl]amino}-piperidine-1-carboxylate | 637.8 | 134 |
| Chiral | 5-[4-(2-diethylamino-ethoxy)-phenyl]-2-(3-hydroxy-urea)-thiophene-3-carboxylic acid-(S)-piperidin-3-ylamide | 475.2 | 136 |
| Chiral | 2-[(aminocarbonyl)amino]-N-[(3S)-azepan-3-yl]-5-(3-methoxyphenyl)thiophene-3-carboxamide | 388.5 | 137 |

TABLE 2-continued

| Structure | | IUPAC Name | M.W. (g/mol) | Ex. |
|---|---|---|---|---|
| | Chiral | 2-[(aminocarbonyl)amino]-5-(2-hydroxyphenyl)-N-[(3S)-piperidin-3-yl]thiophene-3-carboxamide | 360.4 | 138 |
| | Chiral | 2-[(aminocarbonyl)amino]-5-(3-methoxyphenyl)-N-[(3S)-piperidin-3-yl]thiophene-3-carboxamide | 374.5 | 139 |
| | Chiral | 2-[(aminocarbonyl)amino]-5-[2-(benzyloxy)phenyl]-N-[(3S)-piperidin-3-yl]-thiophene-3-carboxamide | 450.6 | 140 |

Example 4

2-[(Aminocarbonyl)amino]-5-(4-methoxyphenyl)-N-[(3S)-piperidin-3-yl]thiophene-3-carboxamide (4-Methoxy-phenyl)-acetaldehyde. To a stirred solution of (4-Methoxy-phenyl)-acetic acid methyl ester (18.0 g, 100 mmol) in anhydrous toluene (200 mL) cooled to −78° C. under $N_2$ was added diisobutylaluminum hydride (DIBAL, 1.0 M in toluene, 150 mL, 150 mmol) over a period of 10-15 minutes. The mixture was stirred at −78° C. for an additional 2 h. The reaction was quenched by the slow addition of MeOH, followed by the introduction of 10% Rochelle's Salt. The suspension was diluted with EtOAc and stirred at room temperature for 1 h. The EtOAc layer was set aside and the aqueous layer was extracted with EtOAc(2×). The combined organic layers were combined and dried over $Na_2SO_4$ and filtered. The solution was concentrated under vacuum to yield 12.0 g (100%) of the title aldehyde as a yellow viscous semi-solid, which was used in the next step without purification. LC/MS (APCI, ES, M+H=151).

2-Amino-5-(4-methoxy-phenyl)-thiophene-3-carboxylic acid methyl ester. To a solution of 4-methoxyphenylacetaldehyde (12.0 g) in DMF (200 mL) was added cyanomethyl acetate (8.9 mL, 100 mmol) and sulfur (3.2 g, 100 mmol), followed by diisopropylethylamine (Hunig's Base, 17.4 mL, 100 mmol). The resultant suspension immediately turned dark yellow to brown with an exotherm. The reaction mixture was stirred overnight at room temperature. The reaction was slowly added to water (~1 L) while stirring. A tan precipitate formed and was filtered after an additional 30 minutes of stirring. The resultant solid was purified by column chromatography ($SiO_2$, 10-20% EtOAc/hexanes) to yield 15.3 g (58%) of the title compound as a light yellow solid. $^1$H NMR ($d_6$-DMSO δ 7.41, br s, 2H; δ 7.37, d, 2H; δ 7.07, s, 1H; δ 6.90, d, 2H; δ 3.75, s, 3H; δ 3.72, s, 3H), LC/MS (APCI, ES, M+H=264).

Methyl 5-(4-methoxyphenyl)-2-({[(trichloroacetyl)amino]carbonyl}amino)thiophene-3-carboxylate. To a stirred solution of 2-Amino-5-(4-methoxy-phenyl)-thiophene-3-carboxylic acid methyl ester (7.15 g, 27.2 mmol) in anhydrous THF (150 mL) was added trichloroacetyl isocyanate (6.4 mL, 54 mmol) slowly over a period of 5 min. After the addition was complete, a precipitate formed and the reaction stirred for an additional 1 h. The desired product was obtained by filtration to give 6.9 g (56%) an off-white solid. The product was used in the next step without purification $^1$H NMR ($d_6$-DMSO δ 12.3, br s, 1H; δ 12.2, s, 1H; δ 7.46, d, 2H;

δ 7.32, s, 1H; δ 6.85, d, 2H; δ 3.75, s, 3H; δ 3.66, s, 3H), LC/MS (APCI, ES, M+H=451).

tert-Butyl(3S)-3-({[2-[(aminocarbonyl)amino]-5-(4-methoxyphenyl)-3-thienyl]carbonyl}amino)piperidine-1-carboxylate. To a solution of methyl 5-(4-methoxyphenyl)-2-({[(trichloroacetyl)amino]carbonyl}amino)thiophene-3-carboxylate (1.0 g, 2.2 mmol) in dry THF (20 mL) was added a solution of [Me$_2$Al-3-Boc-(S)-3-aminopiperidine] in THF (which was preformed by the addition of Me$_3$Al (2.0 M in hexanes, 2.2 nL, 4.4 mmol) to a solution of (S)-3-Amino-piperidine-1-carboxylic acid tert-butyl ester (0.89 g, 4.4 mmol) in 10 mL THF at −78° C. followed by warming to room temperature for an additional 15 min). The resulting orange-colored solution was stirred overnight at room temperature. The reaction mixture was cooled with ice and a 10% aqueous solution of Rochelle's salt was added slowly to quench the reaction. The resulting biphasic solution was warmed to room temperature and stirred for an additional 1 h. The mixture was diluted with EtOAc and H$_2$O, the aqueous layer was extracted with EtOAc (3×) and the combined organic extracts were washed with H$_2$O, brine and dried (Na$_2$SO$_4$). Evaporation gave a pale orange solid. Purification by column chromatography (SiO$_2$, 50% EtOAc/hexanes) gave 0.70 g (67%) of a light yellow solid. LC/MS (APCI, ES, M+H=475).

2-[(Aminocarbonyl)amino]-5-(4-methoxyphenyl)-N-[(3S)-piperidin-3-yl]thiophene-3-carboxamide; hydrochloride. To a stirred solution of tert-butyl(3S)-3-({[2-[(aminocarbonyl)amino]-5-(4-methoxyphenyl)-3-thienyl]carbonyl}amino)piperidine-1-carboxylate (0.70 g, 1.47 mmol) in anhydrous MeOH (5.0 mL) was added 4.0N HCl in 1,4-dioxane (10 mL). A small amount of precipitate forms shortly and the reaction is stirred for an additional 4 h at room temperature. The solvent was removed under vacuum. The residue was redissolved in methanol and concentrated under vacuum (2×) to yield 0.51 g (85%) of a light yellow solid. $^1$H NMR (d$_6$-DMSO δ 10.9, s, 1H; δ 9.39, br s, 1H; δ 9.20, br s, 1H; δ 8.37, d, 1H; δ 7.88, s, 1H; δ 7.49, d, 2H; δ 6.96, d, 2H; δ 6.97, br s, 2H; δ 4.24, m, 1H; δ 3.77, s, 3H; δ 3.29, m, 1H; δ 3.11, m, 1H; δ 2.93, m, 2H; δ 1.91, m, 2H; δ 1.68, m, 2H), LC/MS (APCI, ES, M+H=6875).

Example 26

2-[(Aminocarbonyl)amino]-N-[(3S)-azepan-3-yl]-5-(4-methoxyphenyl)thiophene-3-carboxamide hydrochloride (S)-3-Amino-azepane-1-carboxylic acid tert-butyl ester. (S)-Azepan-3-ylamine (5 g; 43.8 mmol) was dissolved in 100 mL of anhydrous CH$_2$Cl$_2$ and cooled to −78° C. while stirring with a magnetic stirring bar. In another flask N-(tert-butoxycarbonyloxy)succinimide [Boc-OSu] (9.7 g; 45 mmol) was dissolved in 50 mL of anhydrous CH$_2$Cl$_2$. To the stirred solution of the amine was added the solution of the succinimide over a period of 10-15 minutes so as to keep the reaction mixture at −78° C. while stirring. After the addition was complete, the reaction was allowed to warm to room temperature and then stirred for an additional 4 h or until the reaction was complete by TLC (Ninhydrin; R$_f$ 0.3; 0.1:1:10 NH$_4$OH; MeOH; CH$_2$Cl$_2$). The reaction mixture was washed with 50 mL of H$_2$O. The aqueous layer was brought to a pH >13 by the addition of 6N NaOH and extracted with CH$_2$Cl$_2$ (3×100 mL). The organic layer was dried over Na$_2$CO$_3$, filtered, and concentrated in a vacuum to yield pure (S)-3-amino-azepane-1-carboxylic acid tert-butyl ester as a viscous oil (5.1 g, 54%). $^1$H NMR (d$_6$-DMSO, d 3.4, m, 2H; d 2.89, m, 1H; d 2.71, m, 1H; d 2.54, m, 1H; d 1.54, m, 3H; d 1.34, m, 3H; d 1.27, s, 9H; d 1.12, m, 2H), LC/MS (APCI, ES, M+H=215).

tert-Butyl(3S)-3-({[2-[(aminocarbonyl)amino]-5-(4-methoxyphenyl)-3-thienyl]carbonyl}amino)azepane-1-carboxylate. To a solution of methyl 5-(4-methoxyphenyl)-2-({[(trichloroacetyl)amino]carbonyl}amino)thiophene-3-carboxylate (1.36 g, 3 mmol) in anhydrous THF (20 mL) was added a solution of [Me$_2$Al-3-Boc-(S)-3-aminohomopiperidine] in THF (preformed by the careful addition of Me$_3$Al (2.0 M in hexanes, 3.0 mL, 6.0 mmol) to a solution of (S)-3-amino-azepane-1-carboxylic acid tert-butyl ester in 10 nL of THF at −78° C. followed by warming to room temperature under nitrogen and stirring for an additional 15 min.). The resulting deep yellow/orange solution was stirred overnight at room temperature. The reaction mixture was cooled with ice and a 10% aqueous solution of Rochelle's salt was added slowly to quench the reaction. The resulting biphasic solution was warmed to room temperature and stirred for an additional 1 h. The mixture was diluted with EtOAc and H$_2$O, the aqueous layer was extracted with EtOAc (3×) and the combined organic extracts were washed with H$_2$O, brine and dried (Na$_2$SO$_4$). Evaporation gave a pale orange solid. Purification by ISCO MPLC (SiO$_2$, 60-80% EtOAc/hexanes) gave 0.9 g (62%) of the title compound as a white solid. $^1$H NMR (d$_6$-DMSO, δ 11.0, s, 1H, δ 7.95, d, 0.5H, δ 7.81, d, 0.5H, δ 7.65, s, 0.5H; δ 7.56, s, 0.5H; δ 7.46, d, 2H; δ 6.97, d, 2H; δ 6.96, br s, 2H; δ 4.19, m, 0.5H; δ 4.11, m, 0.5H; δ 3.77, m, 3H; δ 3.65, m, 1H; δ 3.48, m, 1H; δ 3.20, m, 2H; δ 1.75, m, 3H; δ 1.58, m, 2H; δ 1.42, s, 4.5H; δ 1.39, m, 1H; δ 1.36, s, 4.5H), LC/MS (APCI, ES, M+H=489).

2-[(Aminocarbonyl)amino]-N-[(3S)-azepan-3-yl]-5-(4-methoxyphenyl)thiophene-3-carboxamide; hydrochloride. To a stirred solution of tert-butyl(3S)-3-({[2-[(aminocarbonyl)amino]-5-(4-methoxyphenyl)-3-thienyl]carbonyl}amino)azepane-1-carboxylate (0.9 g, 1.8 mmol) in 1,4-dioxane (10 mL) was added 4.0N HCl in 1,4-dioxane (10 mL, 40 mmol). A precipitate forms shortly and the reaction is stirred for an additional 4 h at room temperature. Due to the hygroscopic nature of the salt form, the solvent was removed under vacuum. The residue was dissolved in methanol and concentrated under vacuum (2×) to yield and off-white solid. Recrystallization from using 2-propanol gave 0.45 g (59%) of a white solid. $^1$H NMR (d$_6$-DMSO, δ 10.9, s, 1H; δ 9.58, br s, 1H; δ 9.29, br s, 1H; δ 8.39, d, 1H; δ 7.82, s, 1H; δ 7.48, d, 2H; δ 6.96, d, 2H; δ 4.36, m, 1H; δ 3.77, s, 3H; δ 3.29, m, 1H; δ 3.20, m, 2H; δ 3.07, m, 1H; δ 1.98, m, 1H; δ 1.84, m, 4H; δ 1.59, m, 1H), LC/MS (APCI, ES, M+H=389).

Example 110

2-[(Aminocarbonyl)amino]-5-{4-[2-(diethylamino)ethoxy]phenyl}-N-[(3S)-piperidin-3-yl]thiophene-3-carboxamide trifluoroacetate To a stirred solution of tert-butyl (3S)-3-({[2-[(aminocarbonyl)amino]-5-(3-methoxyphenyl)-3-thienyl]carbonyl}amino)piperidine-1-carboxylate dissolved in a small amount of methanol was added 4.0 N HCl in dioxane. The solution was stirred for 1 h at RT. The product was purified by Gilson (5% MeCN—H$_2$O→98MeCN—H$_2$O) to yield 27 mg of the title compound as the trifluoroacetate salt. $^1$H NMR (300 MHz, d$_3$-MeOD; δ 7.55(d, 2H), 7.45(s, 1H), 7.05(d, 2H), 4.35(dd, 2H), 4.25(m, 1H), 3.60(dd, 2H), 3.50(m, 1H), 3.30(m, 5H), 2.95(dd, 2H), 2.10(dd, 2H), 1.80(m, 2H), 1.35(t, 6H)), LCMS, (ES, M+H=460).

Example 112 tert-Butyl(3S)-3-{[(2-[(aminocarbonyl)amino]-5-{4-[2-(diethylamino)ethoxy]phenyl}-3-thienyl)carbonyl]amino}piperidine-1-carboxylate trifluoroacetate Methyl{4-[2-(diethylamino)ethoxy]phenyl}acetate To a solution of methyl(4-hydroxyphenyl)acetate (16.6 g, 10 mmol) in DMF (100 mL) was added 2-bromo-N,N-diethylethanamine hydrobromide (2.6 g, 10 mmol) and), $Cs_2CO_3$ (6.6 g, 20 mmol). After 1 h an additional equivalent of the bromide was added and then stirred overnight at room temperature. The reaction mixture was poured in to a large volume of cold water. The product was then isolated by filtration and purified by column chromatography ($SiO_2$, 10% MeOH/DCM) to give 15.6 g of the title compound as an off-white solid. LC/MS (APCI, ES, M+H=266).

{4-[2-(Diethylamino)ethoxy]phenyl}acetaldehyde To a stirred solution of methyl {4-[2-(diethylamino)ethoxy]phenyl}acetate (5.3 g, 20 mmol) in anhydrous toluene (100 L) cooled to −78° C. under $N_2$ was added diisobutylaluminum hydride (DIBAL, 1.0M in toluene, 100 mL, 100 mmol) over a period of 10-15 minutes. The mixture was stirred at −78° C. for an additional 2 h. The reaction was quenched by the slow addition of MeOH, followed by the introduction of 10% Rochelle's Salt. The suspension was diluted with EtOAc and stirred at room temperature for 1 h. The EtOAc layer was set aside and the aqueous layer was extracted with EtOAc(2×). The combined organic layers were combined and dried over $Na_2SO_4$ and filtered. The solution was concentrated under vacuum to yield 4.7 g (100%) of the title aldehyde as a yellow viscous semisolid, which was used in the next step without purification. LC/MS (APCI, ES, M+H=236).

Methyl 2-amino-5-{4-[2-(diethylamino)ethoxy]phenyl}thiophene-3-carboxylate To a solution of {4-[2-(diethylamino)ethoxy]phenyl}acetaldehyde (4.7 g, 20 mmol) in DMF (30 mL) was added cyanomethyl acetate (1.5 nL, 20 mmol) and sulfur (0.6 g, 20 mmol), followed by diisopropylethylamine (Hunig's Base, 2.5 mL, 20 mmol). The resultant suspension immediately turned dark yellow to brown with an exotherm. The reaction mixture was stirred overnight at room temperature. The reaction was slowly added to water (~200 mL) while stirring. A tan precipitate formed and was filtered after an additional 30 minutes of stirring. The resultant solid was purified by column chromatography ($SiO_2$, 5-10% MeOH/DCM/0.5% $NH_4OH$) to yield 2.4 g of the title compound as a light yellow solid. LC/MS (APCI, ES, M+H=349).

2-Amino-5-{4-[2-(diethylamino)ethoxy]phenyl}thiophene-3-carboxylic acid To a stirred solution of methyl 2-amino-5-{4-[2-(diethylamino)ethoxy]phenyl}thiophene-3-carboxylate (2.0 g, 5.7 mmol) in MeOH (50 mL) was added 6N NaOH (50 mL) and water (50 mL). The reaction was heated to reflux for 2 h or until starting material was gone by TLC or LCMS. The solution was concentrated under vacuum to about half of the original volume. The pH of the resultant cloudy mixture was adjusted to 3-5 by the careful addition of 6N HCl (~150 mL) while stirring. The gummy red precipitate was filtered and dried. Purification was achieved by triturating in boiling hexanes. The product (1.6 g) was isolated in pure form by filtration after cooling to room temperature and drying in a vacuum oven overnight. LC/MS (APCI, ES, M+H=335).

tert-Butyl(3S)-3-{[(2-amino-5-{4-[2-(diethylamino)ethoxy]phenyl}-3-thienyl)carbonyl]amino}piperidine-1-carboxylate To a stirred solution of 2-amino-5-{4-[2-(diethylamino)ethoxy]phenyl}thiophene-3-carboxylic acid (100 mg, 0.3 mmol) in anhydrous DMF (2.0 mL) is added (S)-3-amino-azepane-1-carboxylic acid tert-butyl ester (60 mg, 0.3 mmol), EDCI (63 mg, 0.33 mmol), HOBt (61 mg, 0.45 mmol), and NMM (0.04 mL, 0.3 mmol). The reaction mixture was stirred overnight at room temperature. The solution was diluted with water and EtOAc. The organic layer was separated and set aside. The remaining aqueous layer was extracted with EtOAc (2×) and then the combined organic extracts were pooled and washed with brine. The resultant EtOAc solution was dried over $Na_2SO_4$, filtered, and concentrated under vacuum to yield a brown solid. Purification was performed by Gilson (5% MeCN—$H_2O$→98% MeCN—$H_2O$) to give 90 mg of an off-white solid. LC/MS (APCI, ES, M+H=517).

tert-Butyl(3S)-3-{[(2-[(aminocarbonyl)amino]-5-{4-[2-(diethylamino)ethoxy]phenyl}-3-thienyl)carbonyl]amino}piperidine-1-carboxylate To a stirred solution of tert-butyl(3S)-3-{[(2-amino-5-{4-[2-(diethylamino)ethoxy]phenyl}-3-thienyl)carbonyl]amino}piperidine-1-carboxylate (90 mg, 0.17 mmol) in anhydrous THF (5.0 mL) was added trichloroacetyl isocyanate (0.09 mL, 0.7 mmol) slowly over a period of 5 min. After the addition was complete, a precipitate formed and the reaction stirred for an additional 1 h. The reaction mixture was concentrated in a vacuum. The crude residue was dissolved in methanol and then charged with 2.0N $NH_3$ in methanol (0.35 mL). Purification by Gilson (5% MeCN—$H_2O$→98% MeCN—$H_2O$) gave the title (50 mg) as a tan solid. $^1$H NMR (300 MHz, $d_3$-MeOD; δ 7.55(d, 2H), 7.45(s, 1H), 7.05(d, 2H), 4.35(dd, 2H), 3.60-3.90(m, 3H), 3.60(dd, 2H), 3.30(m, 4H), 2.95(m, 2H), 1.90(dd, 2H), 1.55(m, 2H), 1.45(s, 9H), 1.35(t, 6H)), (APCI, ES, M+H=560).

Example 123

N-[(3S)-Azepan-3-yl]-5-(4-methoxyphenyl)-2-{[(pyrazin-2-ylamino)carbonyl]amino}thiophene-3-carboxamide hydrochloride 2-Amino-5-(4-methoxy-phenyl)-thiophene-3-carboxylic acid. To a stirred solution of 2-amino-5-(4-methoxy-phenyl)-thiophene-3-carboxylic acid methyl ester (6.6 g, 26.6 mmol) in MeOH (200 mL) was added 6N NaOH (100 mL) and water (50 mL). The reaction was heated to reflux for 2 h or until starting material was gone by TLC or LCMS. The solution was concentrated under vacuum to about half of the original volume. The pH of the resultant cloudy mixture was adjusted to 3-5 by the careful addition of 6N HCl (~150 mL) while stirring. The gummy red precipitate was filtered and dried. Purification was achieved by triturating in boiling hexanes. The product (6.0 g, 91%) was isolated in pure form by filtration after cooling to room temperature and drying in a vacuum oven overnight. $^1$H NMR ($d_6$-DMSO δ 7.37, d, 2H, δ 7.11, s, 1H; δ 7.10, br s, 2H; δ 6.94, d, 2H), LC/MS (APCI, ES, M+H=250).

Pyrazine-2-carboxylic acid hydrazide. To a stirred solution of pyrazine-2-carboxylic acid methyl ester (11.1 g, 80 mmol) in 140 mL of EtOH was added hydrazine hydrate (15.6 mL, 320 mmol). The resultant solution was heated to reflux for 2 h. The solvent was removed under reduced pressure and dried under high vacuum to yield the title amide (11.1 g, 100%) as a white solid. The product was used in subsequent steps without purification. $^1$H NMR ($d_6$-DMSO δ 10.1, br s, 1H; δ 9.12, d, 1H; δ 8.83, d, 1H; δ 8.70, dd, 1H; δ 4.64, br s, 2H), LC/MS (APCI, ES, M+H=139).

Pyrazine-2-carbonyl azide. Pyrazine-2-carboxylic acid hydrazide (11.1 g, 80 mmol) was dissolved in 140 mL of water and charged with 6N HCl (13.3 mL, 80 mmol) and cooled to 0° C. To the stirred reaction mixture was added a solution of sodium nitrite (8.3 g, 120 mmol) in 80 mL of water was added slowly over a period of 15-30 minutes using an addition funnel. After the addition was complete the reaction was warmed to room temperature and stirred for an additional 5 h. The solution was the neutralized by the careful addition of solid NaHCO$_3$ and then extracted with CHCl$_3$ (3×). The pooled organic fractions were dried over Na$_2$SO$_4$, filtered, concentrated and dried under high vacuum overnight to yield 2.5 g (21%) the title acyl azide. The product was used in subsequent steps without purification. $^1$H NMR (d$_6$-DMSO δ 9.30, d, 1H; δ 9.03, d, 1H; δ 8.90, dd, 1H).

(S)-3-{[2-Amino-5-(4-methoxy-phenyl)-thiophene-3-carbonyl]-amino}-azepane-1carboxylic acid tert-butyl ester. To a stirred solution of 2-amino-5-(4-methoxy-phenyl)-thiophene-3-carboxylic acid (1.0 g, 4.0 mmol) in anhydrous DMF (20 mL) is added (S)-3-amino-azepane-1-carboxylic acid tert-butyl ester (1.03 g, 4.8 mmol), BOP (2.6 g, 6.0 mmol) and NMM (0.6 mL, 5 mmol). The reaction mixture was stirred overnight at room temperature. The solution was diluted with water and EtOAc. The organic layer was separated and set aside. The remaining aqueous layer was extracted with EtOAc (2×) and then the combined organic extracts were pooled and washed with brine. The resultant EtOAc solution was dried over Na$_2$SO$_4$, filtered, and concentrated under vacuum to yield a brown solid. Purification was performed by ISCO MPLC (SiO$_2$, 30-50% EtOAc/hexanes) to give 0.9 g (50%) of an off-white solid. $^1$H NMR (d$_6$-DMSO δ 7.51, d, 0.5H; δ 7.46, s, 0.5H; δ 7.37, s, 0.5H; δ 7.36, d, 0.5H; δ 7.34, br s, 2H; δ 7.33, d, 2H; δ 6.93, d, 2H; δ 4.11, br s, 1H; δ 3.76, s, 3H; δ 3.61, dq, 1H; δ 3.47, m, 1H; δ 3.11, m, 2H; δ 1.73, m, 3H; δ 1.56, m, 2H; δ 1.42, s, 4.5H; δ 1.38, s+m, 5.5H;), LC/MS (APCI, ES, M+H=446).

tert-Butyl(3S)-3-{[(5-(4-methoxyphenyl)-2-{[(pyrazin-2-ylamino)carbonyl]amino}-3-thienyl)carbonyl]amino}azepane-1-carboxylate. A solution of (S)-3-{[2-amino-5-(4-methoxy-phenyl)-thiophene-3-carbonyl]-amino}-azepane-1carboxylic acid tert-butyl ester (0.76 g, 1.7 mmol) and pyrazine-2-carbonyl azide (0.5 g, 3.4 mmol) in 20 mL of anhydrous DME was refluxed for 2 h. The solvent was removed under reduced pressure and the crude product was purified using ISCO MPLC (40-60% EtOAc/hexanes) to give the title 0.51 g (53%) compound as a light yellow solid. $^1$H NMR (d$_6$-DMSO δ 12.5, br s, 0.5H; δ 12.4, br s, 0.5H; δ 10.90, s, 0.5H; δ 10.88, s, 0.5H; δ 8.93, s, 0.5H; δ 8.89, s, 0.5H; δ 8.33, d, 1H; δ 8.29, t, 1H; δ 8.05, d, 0.5H; δ 7.91, d, 0.5H; δ 7.74, s, 0.5H; δ 7.65, s, 0.5H; δ 7.52, dd, 2H; δ 7.00, d, 2H; δ 4.26, m, 0.5H; δ 4.17, m, 0.5H; δ 3.79, s, 3H; δ 3.69, m, 1H; δ 3.48, m, 1H; δ 3.21, m, 2H; δ 1.77, m, 3H; δ 1.61, m, 2H; δ 1.44, s, 4.5H; δ 1.38, s+m, 5.5H), LC/MS (APCI, ES, M+H=567).

N-[(3S)-Azepan-3-yl]-5-(4-methoxyphenyl)-2-{[(pyrazin-2-ylamino)carbonyl]amino}thiophene-3-carboxamide; hydrochloride. To a stirred solution of tert-butyl(3S)-3-{[(5-(4-methoxyphenyl)-2-{[(pyrazin-2-ylamino) carbonyl]amino}-3-thienyl)carbonyl]amino}azepane-1-carboxylate (0.51 g, 0.9 mmol) in 10 mL of MeOH is added 10 mL (40 mmol) of 4.0 N HCl in dioxane. The solution was stirred at room temperature for 4 h and then concentrated under vacuum. The residue was partially recrystallized by triturating in refluxing 2-propanol to yield the title compound are a light orange solid (0.30 g, 67%). $^1$H NMR (d$_6$-DMSO δ 12.6, br s, 1H; δ 10.9, s, 1H; δ 9.55, br s, 1H; δ 9.24, br s, 1H; δ 8.88, s, 1H; δ 8.49, d, 1H; δ 8.35, dd, 1H; δ 8.29, d, 1H; δ 7.92, s, 1H; δ 7.54, d, 1H; δ 6.99, d, 2H; δ 4.42, m, 1H; δ 3.33, m, 1H; δ 3.23, m, 2H; δ 3.10, m, 1H; δ 2.02, m, 1H; δ 1.85, m, 4H; δ 1.62, m, 1H;), LC/MS (APCI, ES, M+H=467).

Example 136

2-[(Aminocarbonyl)amino]-5-{4-[2-(diethylamino) ethoxy]phenyl}-N-[(3S)-piperidin-3-yl]thiophene-3-carboxamide trifluoroacetate tert-Butyl(3S)-3-{[(5-{4-[2-(diethylamino)ethoxy]phenyl}-2-{[(hydroxyamino) carbonyl]amino}-3-thienyl)carbonyl]amino}piperidine-1-carboxylate To a solution of tert-butyl (3S)-3-{[(2-amino-5-{4-[2-(diethylamino)ethoxy]phenyl}-3-thienyl)carbonyl]amino}piperidine-1-carboxylate (115 mg, 0.22 mmol) in THF (640 μL) was added 1,1'-carbonyl diimidazole (178 mg, 1.1 mmol). The resulting cloudy solution was stirred at rt for 1 h whereupon hydroxylamine hydrochloride (76.4 mg, 1.1 mmol) and Et$_3$N (100 μL) were added and the resulting dark solution was stirred for 48 h at rt. The mixture was partitioned between EtOAc and H$_2$O and the organic layer was washed with H$_2$O, brine and dried (MgSO$_4$). Evaporation afforded a yellow residue. Purification by Gilson (5% MeCN—H$_2$O→98% MeCN—H$_2$O) gave the title hydroxy urea.

5-{4-[2-(Diethylamino)ethoxy]phenyl}-2-{[(hydroxyamino)carbonyl]amino}-N-[(3S)-piperidin-3-yl]thiophene-3-carboxamide A stirred solution of tert-butyl (3S)-3-{[(5-{4-[2-(diethylamino)ethoxy]phenyl}-2-{[(hydroxyamino)carbonyl]amino}-3-thienyl)carbonyl]amino}piperidine-1-carboxylate in dioxane was treated with 4.0N HCl solution in dioxane (3 mL) and the resulting cloudy mixture was stirred at rt for 1 h. Evaporation of the solvent gave 5-[4-(2-diethylamino-ethoxy)-phenyl]-2-(3-hydroxyurea)-thiophene-3-carboxylic acid-(S)-piperidin-3-ylamide as the hydrochloride salt (8 mg). $^1$H NMR (300 MHz, DMSO-d$_6$) δ ppm 1.17-1.40 (m, 6H) 1.54-1.81 (m, 2H) 1.84-2.07 (m, 2H) 2.76-2.99 (m, 2H) 3.05-3.25 (m, 4H) 3.41-3.61 (m, 4H) 3.73-3.88 (m, 1H) 4.29-4.42 (m, 1H) 4.40-4.64 (m, 1H) 5.86 (s, 1H) 7.07 (d, J=8.48 Hz, 2H) 7.55 (d, J=8.48 Hz, 2H) 7.82 (s, 1H) 9.44 (s, 1H) 9.65 (s, 1H); LC/MS (ES, M+H=476).

Example 137

2-[(Aminocarbonyl)amino]-N-[(3S)-azepan-3-yl]-5-(3-methoxyphenyl)thiophene-3-carboxamide tert-Butyl(3S)-3-[({2-[(aminocarbonyl)amino]-5-bromo-3-thienyl}carbonyl)amino]azepane-1-carboxylate To a solution of methyl 2-[(aminocarbonyl)amino]-5-bromothiophene-3-carboxylate (1 equiv) in dry THF (0.3 M) was added a solution of [Me$_2$Al—Boc-3-(S)-aminohomopiperidine] (2 equiv) in THF (1.0 M) (which was preformed by the addition of Me$_3$Al (2.0 M in hexanes) to a solution of Boc-3-(S)-homopiperidine in THF at −78° C. and the resulting yellow solution was warmed to room temperature and stirred for an additional 15 min) and the resulting deep yellow solution was stirred overnight at room temperature. The reaction mixture was cooled with ice and a 10% aqueous solution of Rochelle's salt was added slowly to quench the reaction. The resulting biphasic solution was warmed to room temperature and stirred for an additional 1 h. The mixture was diluted with EtOAc and H$_2$O, the aqueous layer was extracted with EtOAc (3×) and the combined organic extracts were washed with H$_2$O, brine and dried (MgSO$_4$). Evaporation gave a pale orange solid. Purification by column chromatography (40-60% EtOAc/Hexanes) gave a white solid. LC/MS (ES, M+H=462).

tert-Butyl(3S)-3-({[2-[(aminocarbonyl)amino]-5-(3-methoxyphenyl)-3-thienyl]carbonyl}amino)azepane-1-carboxylate A flask was loaded with tert-butyl(3S)-3-[({2-[(aminocarbonyl)amino]-5-bromo-3-thienyl}carbonyl)amino]azepane-1-carboxylate (1.0 mmol), 3-methoxyphenylboronic acid (1.5 mmol), $Cs_2CO_3$ (3.0 mmol) and $Pd(PPh_3)_4$ (0.05-0.1 mmol) and was purged with nitrogen for 10 mins. Dioxane (4 mL) and $H_2O$ (1 mL) were added under nitrogen atmosphere and the resulting mixture was heated to 90° C. for 2-4 h. The mixture was allowed to cool to RT and the mixture was filtered (0.45 uM or diatomaceous earth). The water layer was separated and remaining solvent was concentrated to dryness. The residue was purified by column chromatography ($SiO_2$) on an MPLC ISCO separation system (30-60% EtOAc/hexanes) to give an off-white solid. LCMS, (ES, M+H=489).

2-[(Aminocarbonyl)amino]-N-[(3S)-azepan-3-yl]-5-(3-methoxyphenyl)thiophene-3-carboxamide hydrochloride To a stirred solution of tert-butyl(3S)-3-({[2-[(aminocarbonyl)amino]-5-(3-methoxyphenyl)-3-thienyl]carbonyl}amino)azepane-1-carboxylate dissolved in a small amount of methanol was added 4.0 N HCl in dioxane. The solution was stirred for 1 h at RT. The product as the hydrochloride salt was obtained as an off-white solid after removal of the solvent and drying. $^1$H NMR ($d_6$-DMSO δ 10.90 (s, 1H), 9.21 (s, 1H), 9.01 (s, 1H), 8.29 (d, 1H), 7.93 (s, 1H), 7.29 (t, 1H), 7.11 (d, 2H), 7.03 (s, 1H), 6.83 (d, 1H), 4.33 (s, 1H), 3.81 (s, 3H), 3.20 (m, 4H), 2.00 (m, 1H), 1.84 (m, 4H), 1.56 (m, 1H)), LCMS, (ES, M+H=389).

Example 139

2-[(Aminocarbonyl)amino]-5-(3-methoxyphenyl)-N-[(3S)-piperidin-3-yl]thiophene-3-carboxamide Methyl 2-({[(trichloroacetyl)amino]carbonyl}amino)thiophene-3-carboxylate. To a stirred solution of 2-aminothiophene-3-carboxylic acid methyl ester (1 eq) in anhydrous THF (mL) was added trichloroacetyl isocyanate (1 eq) slowly over a period of 5 min. After the addition was complete, a precipitate formed and the reaction stirred for an additional 1 h. The desired product was obtained by filtration to give methyl 2-({[(trichloroacetyl)amino]carbonyl}amino)thiophene-3-carboxylate (99%) as an off-white solid. The product was used in the next step without any further purification. LC/MS (ES, M+H=345).

Methyl 5-bromo-2-({[(trichloroacetyl)amino]carbonyl}amino)thiophene-3-carboxylate. To a stirred solution of methyl 2-({[(trichloroacetyl)amino]carbonyl}amino)thiophene-3-carboxylate (1 eq) in glacial acetic acid (20 mL) was added a solution of bromine (1.3 eq) in glacial acetic acid (5 mL) slowly over a period of 5 min. After the addition was complete, the resulting dark solution was stirred for 30 mins at RT. The solvent was evaporated under vaccum and the residue was triturated with $H_2O$. The title compound was obtained by filtration (99%) as an off-white solid. The product was used in the next step without any further purification after drying for 2 days under $P_2O_5$. LC/MS (ES, M+H=425).

Methyl 2-[(aminocarbonyl)amino]-5-bromothiophene-3-carboxylate. A stirred solution of methyl 5-bromo-2-({[(trichloroacetyl)amino]carbonyl}amino)thiophene-3-carboxylate (1 eq) in anhydrous methanol was purged with dry ammonia for 20 mins. After stirring for extra 10 mins at RT, precipitation was observed and the product was isolated by filtration (100% yield). LC/MS (ES, M+H=280).

tert-Butyl(3S)-3-[({2-[(aminocarbonyl)amino]-5-bromo-3-thienyl}carbonyl)amino]piperidine-1-carboxylate To a solution of methyl 2-[(aminocarbonyl)amino]-5-bromothiophene-3-carboxylate (1 equiv) in dry THF (0.3 M) was added a solution of [$Me_2Al$—Boc-3-(S)-aminopiperidine] (2 equiv) in THF (1.0M) (which was preformed by the addition of $Me_3Al$ (2.0M in hexanes) to a solution of Boc-3-(S)-piperidine in THF at −78° C. and the resulting yellow solution was warmed to room temperature and stirred for an additional 15 min) and the resulting deep yellow solution was stirred overnight at room temperature. The reaction mixture was cooled with ice and a 10% aqueous solution of Rochelle's salt was added slowly to quench the reaction. The resulting biphasic solution was warmed to room temperature and stirred for an additional 1 h. The mixture was diluted with EtOAc and $H_2O$, the aqueous layer was extracted with EtOAc (3×) and the combined organic extracts were washed with $H_2O$, brine and dried ($MgSO_4$). Evaporation gave a pale orange solid. Purification by column chromatography (40-60% EtOAc/Hexanes) gave a white solid. $^1$H NMR ($d_6$-DMSO, δ 10.9, s, 1H; δ 9.48, br s, 1H; δ 9.31, br s, 1H; δ 8.48, d, 1H; δ 8.10, s, 1H, δ 7.57, d, 2H, δ 7.38, t, 2H, δ 7.23, t, 1H, δ 7.01, br s, 2H; δ 4.26, m, 1H; δ 3.29, m, 1H, δ 3.11, m, 1H, δ 2.94, m, 2H; δ 1.91, m, 2H; δ 1.69, m, 2H), LC/MS (APCI, ES, M+H=345).

tert-Butyl(3S)-3-({[2-[(aminocarbonyl)amino]-5-(3-methoxyphenyl)-3-thienyl]carbonyl}amino)piperidine-1-carboxylate A flask was loaded with tert-butyl(3S)-3-[({2-[(aminocarbonyl)amino]-5-bromo-3-thienyl}carbonyl)amino]piperidine-1-carboxylate (1.0 mmol), 3-methoxyphenylboronic acid (1.5 mmol), $Cs_2CO_3$ (3.0 mmol) and $Pd(PPh_3)_4$ (0.05-0.1 mmol) and was purged with nitrogen for 10 mins. Dioxane (4 mL) and $H_2O$ (1 mL) were added under nitrogen atmosphere and the resulting mixture was heated to 90° C. for 2-4 h. The mixture was allowed to cool to RT and the mixture was filtered (0.45 uM or diatomaceous earth). The water layer was separated and remaining solvent was concentrated to dryness. The residue was purified by column chromatography ($SiO_2$) on an MPLC ISCO separation system (30-60% EtOAc/hexanes) to give an off-white solid. LCMS, (ES, M+H=475).

2-[(Aminocarbonyl)amino]-5-(3-methoxyphenyl)-N-[(3S)-piperidin-3-yl]thiophene-3-carboxamide hydrochloride To a stirred solution of tert-butyl(3S)-3-({[2-[(aminocarbonyl) amino]-5-(3-methoxyphenyl)-3-thienyl]carbonyl}amino)piperidine-1-carboxylate dissolved in a small amount of methanol was added 4.0 N HCl in dioxane. The solution was stirred for 1 h at RT. The product as the hydrochloride salt was obtained as an off-white solid after removal of the solvent and drying. $^1$H NMR ($d_6$-DMSO δ 10.94 (s, 1H), 9.41 (s, 1H), 9.19 (s, 1H), 8.47 (d, 1H), 8.11 (s, 1H), 7.30 (t, 1H), 7.15 (d, 1H), 7.05 (br, 2H), 6.84 (d, 1H), 4.25 (s, 1H), 3.82 (s, 3H), 3.29 (d, 1H), 3.12 (d, 1H), 2.97 (m, 2H), 1.92 (d, 2H), 1.69 (m, 2H)), LCMS, (ES, M+H=375).

Other Examples

Examples 1-3, 5-25, and 27-109 were prepared in a similar fashion to that described for examples 4 and 26.

Examples 111 and 113-115 were prepared in a similar fashion to that described for examples 110 and 112.

Examples 116-119 were prepared according to the general Scheme V.

Examples 121-122 and 124-135 were prepared in a similar fashion to that described for examples 123 and 136.

Examples 138 and 140 were prepared in a similar fashion to that described for examples 137 and 139.

The invention claimed is:

1. A compound of formula (I) or a pharmaceutically-acceptable salt or in vivo-hydrolysable precursors thereof:

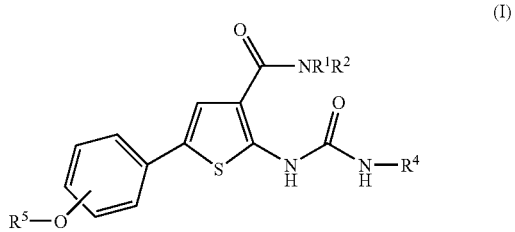

(I)

wherein:
$R^1$ is an optionally substituted heterocyclyl;
$R^2$ is selected from H, optionally substituted $C_{1-6}$alkyl, or optionally substituted heterocyclyl;
$R^4$ is selected from H, OH, optionally substituted carbocyclyl, optionally substituted heterocyclyl, or optionally substituted $C_{1-6}$alkyl;
$R^5$ is selected from H, optionally substituted carbocyclyl, or optionally substituted $C_{1-6}$alkyl.

2. A compound of formula (I) or a pharmaceutically-acceptable salt or an in vivo-hydrolysable precursor thereof as recited in claim 1 wherein $R^2$, $R^4$, and $R^5$ have any of the meanings defined in claim 1 and $R^1$ is an optionally substituted heterocyclyl wherein 1,2, or 3 substituents is/are independently selected from halogen, nitro, amino, cyano, trifluoromethyl, alkyl, alkenyl, alkynyl, haloalkyl, alkoxy, hydroxy, alkylhydroxy, carbonyl, —CH(OH)CH$_3$, —CH$_2$NH-alkyl-OH, alkyl-(OH)CH$_3$, —CH$_2$-phenyl-(OCH$_3$)$_2$, —Oalkyl, —OCH$_3$, —Ophenyl, —OCOalkyl, —NHCHO, —Nalkyl, —N-(alkyl)-CHO, —NH—CO-amino, —N-(alkyl)-CO-amino, —NH—COalkyl, —N-(alkyl)-COalkyl, -carboxy, -amidino, —CO-amino, —CO-alkyl, —CO$_2$alkyl, mercapto, —Salkyl, —SCH$_2$furanyl, —SO(alkyl), —SO$_2$(alkyl), —SO$_2$-amino, -alkylsulfonylamino, phenyl, anisole, dimethoxyphenyl, trimethoxyphenyl, halophenyl, cycloalkyl, heterocyclyl, -alkyl-NH-cycloalkyl, -alkyl-NH-heterocyclyl, -alkyl-NH-alkyl-OH, —C(=O)OC(CH$_3$)$_3$, —N(CH$_3$)$_2$, —N(CH$_2$CH$_3$)$_2$, -alkyl-NH- alkyl- heterocyclyl, -alkyl-aryl, -methyl-phenyl, alkyl-polycyclyl, alkyl-amino, alkyl-hydroxy, —CH$_2$NH-alkyl-heterocyclyl, —CH$_2$NHCH2CH(CH$_3$)$_2$, vicinal —O(alkyl)O—, vicinal —OC(haloalkyl)O—, vicinal —CH$_2$O(alkyl)O—, vicinal —S(alkyl)S— and —O(alkyl)S—.

3. A compound of formula (I) or a pharmaceutically-acceptable salt or an in vivo-hydrolysable precursor thereof as recited in claim 1 wherein $R^2$, $R^4$, and $R^5$ have any of the meanings defined in claim 1 and $R^1$ is an optionally substituted heterocyclyl wherein 1,2, or 3 substituents is/are independently selected from: —OH, C(=O)OC(CH$_3$)$_3$, NH$_2$, $C_{1-6}$alkyl, methoxybenzene, or dimethoxy benezene.

4. A compound of formula (I) or a pharmaceutically-acceptable salt or an in vivo-hydrolysable precursor thereof as recited in claim 1 wherein $R^2$, $R^4$, and $R^5$ have any of the meanings defined in claim 1 and
$R^1$ is a heterocyclyl wherein heterocyclyl is selected from piperdinyl, pyridinyl, pyrrolidinyl, pyrazinyl, azepanyl, azetidinyl, azabicyclozinyl, furanyl, thienyl.

5. A compound of formula (I) or a pharmaceutically-acceptable salt or an in vivo-hydrolysable precursor thereof as recited in claim 1 wherein $R^1$, $R^4$, and $R^5$ have any of the meanings defined in claim 1 and
$R^2$ is H.

6. A compound of formula (I) or a pharmaceutically-acceptable salt or an in vivo-hydrolysable precursor thereof as recited in claim 1 wherein $R^1$, $R^2$, and $R^5$ have any of the meanings defined in claim 1 and
$R^4$ is H.

7. A compound of formula (I) or a pharmaceutically-acceptable salt or an in vivo-hydrolysable precursor thereof as recited in claim 1 wherein $R^1$, $R^2$, and $R^4$ have any of the meanings defined in claim 1 and
$R^5$ is H or an optionally substituted $C_{1-6}$alkyl.

8. A compound of formula (I) or a pharmaceutically-acceptable salt or an in vivo-hydrolysable precursor thereof as recited in claim 1 wherein $R^1$, $R^2$, and $R^4$ have any of the meanings defined in claim 1 and
$R^5$ is H or an optionally substituted $C_{1-6}$alkyl wherein 1,2 or 3 substituents is/are independently selected from: NH$_2$, NHCH$_3$, N(CH$_2$CH$_3$)$_2$, N(CH$_3$)$_2$, OCH3, OH, —$C_{1-6}$alkyl, morpholino, piperidinyl, pyrrolodinyl.

9. A compound of formula (I) or a pharmaceutically-acceptable salt or an in vivo-hydrolysable precursor thereof as recited in claim 1 wherein $R^1$, $R^2$, and $R^4$ have any of the meanings defined in claim 1 and
$R^5$ is H or an optionally substituted $C_{1-3}$alkyl.

10. A compound of formula (I) or a pharmaceutically-acceptable salt or an in vivo-hydrolysable precursor thereof as recited in claim 1 wherein $R^1$, $R^2$, and $R^4$ have any of the meanings defined in claim 1 and
$R^5$ is H or an optionally substituted $C_{1-3}$alkyl wherein 1,2 or 3 substituents is/are independently selected from: NH$_2$, NHCH$_3$, N(CH$_2$CH$_3$)$_2$, N(CH$_3$)$_2$, OCH3, OH, —$C_{1-6}$alkyl, morpholino, piperidinyl, pyrrolodinyl.

11. A compound of formula (I) or a pharmaceutically-acceptable salt or an in vivo-hydrolysable precursor thereof, as recited in claim 1 wherein:
$R^2$ is H;
$R^4$ is H;
$R^5$ is H or an optionally substituted $C_{1-6}$alkyl.

12. A compound of formula (I) or a pharmaceutically-acceptable salt or an in vivo-hydrolysable precursor thereof, as recited in claim 1 wherein:
$R^1$ is an optionally substituted heterocyclyl wherein the substituent is selected from one or more of the following: —NH$_2$, $C_{1-6}$alkyl, —C(=O)OC(CH$_3$)$_3$,
$R^2$ is H;
$R^4$ is H;
$R^5$ is H or an optionally substituted $C_{1-6}$alkyl wherein the substituent is selected from one or more of the following: —$C_{1-6}$alkyl, —N(C$_{1-3}$alkyl)$_2$.

13. A compound of formula (I) or a pharmaceutically-acceptable salt or an in vivo-hydrolysable precursor thereof, as recited in claim 1 wherein:
$R^1$ is an optionally substituted heterocyclyl wherein the substituent is selected from one or more of the following: —NH$_2$, $C_{1-6}$alkyl, —C(=O)OC(CH$_3$)$_3$,
$R^2$ is H;
$R^4$ is H;
$R^5$ is H or an optionally substituted $C_{1-3}$alkyl wherein 1,2 or 3 substituents is/are independently selected from: NH$_2$, NHCH$_3$, N(CH$_2$CH$_3$)$_2$, N(CH$_3$)$_2$, OCH3, OH, —$C_{1-6}$alkyl, morpholino, piperidinyl, pyrrolodinyl.

14. A compound of formula (I) or a pharmaceutically-acceptable salt or an in vivo-hydrolysable precursor thereof, as recited in claim 1 wherein:
$R^1$ is a heterocyclyl;
$R^2$ is H;
$R^4$ is H;
$R^5$ is H or a $C_{1-6}$alkyl.

15. A compound of formula (I) or a pharmaceutically-acceptable salt or an in vivo-hydrolysable precursor thereof, as recited in claim 1 wherein:
  $R^1$ is a 6-membered heterocyclyl containing at least one N in the ring;
  $R^2$ is H;
  $R^4$ is H;
  $R^5$ is a $C_{1-3}$alkyl.

16. A compound of formula (I) or a pharmaceutically-acceptable salt thereof, as recited in claim 1 selected from:
  tert-butyl 3-{[(2-[(aminocarbonyl)amino]-5-{4-[2-(diethylamino)ethoxy]phenyl}-3-thienyl)carbonyl]amino}piperidine-1-carboxylate;
  2-[(aminocarbonyl)amino]-5-{4-[2-(diethylamino)ethoxy]phenyl}-N-piperidin-3-ylthiophene-3-carboxamide;
  2-[(aminocarbonyl)amino]-5-{3-[2-(diethylamino)ethoxy]phenyl}-N-piperidin-3-ylthiophene-3-carboxamide;
  2-[(aminocarbonyl)amino]-5-(4-methoxyphenyl)-N-[(3S)-piperidin-3-yl]thiophene-3-carboxamide;
  tert-butyl 3-{[(2-[(aminocarbonyl)amino]-5-{3-[2-(diethylamino)ethoxy]phenyl}-3-thienyl)carbonyl]amino}piperidine-1-carboxylate;
  2-[(aminocarbonyl)amino]-5-{4-[2-(diethylamino)ethoxy]phenyl}-N-piperidin-4-ylthiophene-3-carboxamide;
  2[(aminocarbonyl]-N-[(3R)-azepan-3-yl]-5-(4-methoxyphenyl)thiophene-3-carboxamide;
  N-(3-[(4-aminopiperidin-1-yl)carbonyl]-5-{4-[2-(diethylamino)ethoxy]phenyl}-2-thienyl)urea;
  2-[(aminocarbonyl)amino]-5-{3-[2-(diethylamino)ethoxy]phenyl}-N-pyridin-3-ylthiophene-3-carboxamide;
  2-[(aminocarbonyl)amino]-5-(4-methoxyphenyl)-N-(1-methylpiperidin-4-yl)thiophene-3-carboxamide;
  2-[(aminocarbonyl)amino]-5-(4-methoxyphenyl)-N-[(3S)-1-methylazepan-3-yl]thiophene-3-carboxamide;
  2-[(aminocarbonyl)amino]-5-{3-[2-(diethylamino)ethoxy]phenyl}-N-[3-(hydroxymethyl)phenyl]thiophene-3-carboxamide;
  2-[(aminocarbonyl)amino]-5-{4-[2-(diethylamino)ethoxy]phenyl}-N-pyrrolidin-3-ylthiophene-3-carboxamide;
  2-[(aminocarbonyl)amino]-5-{4-[2-(diethylamino)ethoxy]phenyl}-N-pyridin-3-ylthiophene-3-carboxamide;
  2-[(aminocarbonyl)amino]-5-(4-methoxyphenyl)-N-[(3S)-1-methylpiperidin-3-yl]thiophene-3-carboxamide;
  2-[(aminocarbonyl)amino]-5-{3-[2-(diethylamino)ethoxy]phenyl}-N-pyrrolidin-3-ylthiophene-3-carboxamide;
  2-[(aminocarbonyl)amino]-5-(4-methoxyphenyl)-N-[(3R)-piperidin-3-ylmethyl]thiophene-3-carboxamide;
  2-[(aminocarbonyl)amino]-5-(4-methoxyphenyl)-N-[(3S)-pyrrolidin-3-yl]thiophene-3-carboxamide;
  2-[(aminocarbonyl)amino]-5-(4-methoxyphenyl)-N-[(3R)-pyrrolidin-3-yl]thiophene-3-carboxamide;
  2-[(aminocarbonyl)amino]-N-[(3S)-azepan-3-yl]-5-(4-methoxyphenyl)thiophene-3-carboxamide;
  2-[(aminocarbonyl)amino]-5-(4-methoxyphenyl)-N-[(3R)-piperidin-3-yl]thiophene-3-carboxamide;
  2-[(aminocarbonyl)amino]-5-(4-methoxyphenyl)-N-(piperidin-4-ylmethyl)thiophene-3-carboxamide;
  2-[(aminocarbonyl)amino]-5-(4-methoxyphenyl)-N-pyrrolidin-3-ylthiophene-3-carboxamide;
  2-[(aminocarbonyl)amino]-N-(1-ethylpiperidin-3-yl)-5-(4-methoxyphenyl)thiophene-3-carboxamide;
  2-[(aminocarbonyl)amino]-N-[(3S)-1-ethylazepan-3-yl]-5-(4-methoxyphenyl)thiophene-3-carboxamide;
  2-[(aminocarbonyl)amino]-5-(3-hydroxyphenyl)-N-piperidin-4-ylthiophene-3-carboxamide;
  2-[(aminocarbonyl)amino]-5-(4-hydroxyphenyl)-N-piperidin-4-ylthiophene-3-carboxamide;
  2-[(aminocarbonyl)amino]-5-(3-methoxyphenyl)-N-piperidin-4-ylthiophene-3-carboxamide;
  tert-butyl(3S)-3-({[2-[(aminocarbonyl)amino]-5-(4-methoxyphenyl)-3-thienyl]carbonyl}amino)pyrrolidine-1-carboxylate;
  2-[(aminocarbonyl)amino]-5-(4-methoxyphenyl)-N-piperidin-3-ylthiophene-3-carboxamide;
  2-[(aminocarbonyl)amino]-N-(1-benzylpiperidin-4-yl)-5-(4-methoxyphenyl)thiophene-3-carboxamide;
  tert-butyl 3-({[2-[(aminocarbonyl)amino]-5-(4-methoxyphenyl)-3-thienyl]carbonyl}amino)piperidine-1-carboxylate;
  2-[(aminocarbonyl)amino]-5-[4-(2-piperidin-1-ylethoxy)phenyl]-N-(2-pyridin-4-ylethyl)thiophene-3-carboxamide;
  2-[(aminocarbonyl)amino]-5-[4-(2-piperidin-1-ylethoxy)phenyl]-N-(2-pyridin-4-ylethyl)thiophene-3-carboxamide;
  2-[(aminocarbonyl)amino]-N-azetidin-3-yl-5-(4-methoxyphenyl)thiophene-3-carboxamide;
  2-[(aminocarbonyl)amino]-5-(4-methoxyphenyl)-N-[(2S)-pyrrolidin-2-ylmethyl]thiophene-3-carboxamide;
  2-[(aminocarbonyl)amino]-5-(4-methoxyphenyl)-N-pyridin-4-ylthiophene-3-carboxamide;
  2-[(aminocarbonyl)amino]-5-(4-methoxyphenyl)-N-(2-piperazin-1-ylethyl)thiophene-3-carboxamide;
  2-[(aminocarbonyl)amino]-5-(4-methoxyphenyl)-N-(2-piperidin-1-ylethyl)thiophene-3-carboxamide;
  2-[(aminocarbonyl)amino]-5-(4-hydroxyphenyl)-N-(2-pyridin-4-ylethyl)thiophene 3-carboxamide;
  2-[(aminocarbonyl)amino]-5-(4-methoxyphenyl)-N-(2-piperazin-1-ylethyl)thiophene-3-carboxamide;
  2-[(aminocarbonyl)amino]-5-(4-methoxyphenyl)-N-(2-pyridin-4-ylethyl)thiophene-3-carboxamide;
  2-[(aminocarbonyl)amino]-5-(4-hydroxyphenyl)-N-(2-pyridin-3-ylethyl)thiophene-3-carboxamide;
  2-[(aminocarbonyl)amino]-5-(4-methoxyphenyl)-N-(2-pyridin-3-ylethyl)thiophene-3-carboxamide;
  2-[(aminocarbonyl)amino]-5-(4-methoxyphenyl)-N-(2,2,6,6-tetramethylpiperidin-4-yl)thiophene-3-carboxamide;
  2-[(aminocarbonyl)amino]-5-(2-methoxyphenyl)-N-piperidin-4-ylthiophene-3-carboxamide;
  2-[(aminocarbonyl)amino]-5-(4-methoxyphenyl)-N-(tetrahydrofuran-2-ylmethyl)thiophene-3-carboxamide;
  tert-butyl(3R)-3-({[2-[(aminocarbonyl)amino]-5-(4-methoxyphenyl)-3-thienyl]carbonyl}amino)piperidine-1-carboxylate;
  2-[(aminocarbonyl)amino]-5-(4-methoxyphenyl)-N-(pyridin-3-ylmethyl)thiophene-3-carboxamide;
  tert-butyl 3-({[2-[(aminocarbonyl)amino]-5-(4-methoxyphenyl)-3-thienyl]carbonyl}amino)azetidine-1-carboxylate;
  2-[(aminocarbynol)amino-5-(4-methoxyphenyl)-N-(pyridine-4-methyl)thiophene-3-carboximide;
  2-[(aminocarbonyl)amino]-5-(4-methoxyphenyl)-N-[2-(2-thienyl)ethyl]thiophene-3-carboxamide;
  2-[(aminocarbonyl)amino]-5-(4-methoxyphenyl)-N-(2-thienylmethyl)thiophene-3-carboxamide;

N-[3-(1,4-diazepan-1-ylcarbonyl)-5-(4-methoxyphenyl)-2-thienyl]urea;

2-[(aminocarbonyl)amino]-5-(4-hydroxyphenyl)-N-(2-thienylmethyl)thiophene-3-carboxamide;

2-[(aminocarbonyl)amino]-N-{2-[(2-furylmethyl)thio]ethyl}-5-(4-methoxyphenyl)thiophene-3-carboxamide;

2-[(aminocarbonyl)amino]-5-(4-hydroxyphenyl)-N-[2-(2-thienyl)ethyl]thiophene-3-carboxamide;

N-(3-[(4-aminopiperidin-1-yl)carbonyl]-5-{3-[2-(diethylamino)ethoxy]phenyl}-2-thienyl)urea;

2-[(aminocarbonyl)amino]-5-(4-methoxyphenyl)-N-[(3R)-piperidin-3-ylmethyl]thiophene-3-carboxamide;

2-[(aminocarbonyl)amino]-5-(4-methoxyphenyl)-N-(1,2,3,4-tetrahydroquinolin-3-yl)thiophene-3-carboxamide;

2-[(aminocarbonyl)amino]-N-(1,3-benzodioxol-5-ylmethyl)-5-(4-methoxyphenyl)thiophene-3-carboxamide;

2-[(aminocarbonyl)amino]-5-(4-methoxyphenyl)-N-[(5-methyl-2-furyl)methyl]thiophene-3-carboxamide;

2-[(aminocarbonyl)amino]-5-(4-methoxyphenyl)-N-(pyridin-2-ylmethyl)thiophene-3-carboxamide;

tert-butyl 4-({[2-[(aminocarbonyl)amino]-5-(3-methoxyphenyl)-3-thienyl]carbonyl}amino)piperidine-1-carboxylate;

2-[(aminocarbonyl)amino]-5-(4-methoxyphenyl)-N-(2-pyridin-2-ylethyl)thiophene-3-carboxamide;

tert-butyl 4-({[2-[(aminocarbonyl)amino]-5-(4-methoxyphenyl)-3-thienyl]carbonyl}amino)piperidine-1-carboxylate;

2-[(aminocarbonyl)amino]-5-{4-[2-(diethylamino)ethoxy]phenyl}-N-[(3S)-piperidin-3-yl]thiophene-3-carboxamide;

2-[(aminocarbonyl)amino]-5-{4-[2-(diethylamino)ethoxy]phenyl}-N-[(3R)-piperidin-3-yl]thiophene-3-carboxamide;

tert-butyl(3S)-3-{[(2-[(aminocarbonyl)amino]-5-{4-[2-(diethylamino)ethoxy]phenyl}-3-thienyl)carbonyl]amino}piperidine-1-carboxylate;

2-[(aminocarbonyl)amino]-N-[(3S)-azepan-3-yl]-5-{4-[2-(diethylamino)ethoxy]phenyl}thiophene-3-carboxamide;

tert-butyl(3R)-3-{[(2-[(aminocarbonyl)amino]-5-{4-[2-(diethylamino)ethoxy]phenyl}-3-thienyl)carbonyl]amino}piperidine-1-carboxylate;

N-[3-{[(3S)-3-aminoazepan-1-yl]carbonyl}-5-(4-methoxyphenyl)-2-thienyl]urea;

5-{4-[2-(diethylamino)ethoxy]phenyl}-2-{[(pyrazin-2-ylamino)carbonyl]amino}-N-[(3S)-pyrrolidin-3-yl]thiophene-3-carboxamide;

5-{3-[2-(diethylamino)ethoxy]phenyl}-2-{[(pyrazin-2-ylamino)carbonyl]amino}-N-[(3S)-pyrrolidin-3-yl]thiophene-3-carboxamide;

5-{3-[2-(diethylamino)ethoxy]phenyl}-N-piperidin-4-yl-2-{[(pyrazin-2-ylamino)carbonyl]amino}thiophene-3-carboxamide;

N-[(3S)-azepan-3-yl]-5-(4-methoxyphenyl)-2-{[(pyrazin-2-ylamino)carbonyl]amino}thiophene-3-carboxamide;

5-{3-[2-(diethylamino)ethoxy]phenyl}-N-piperidin-3-yl-2-{[(pyrazin-2-ylamino)carbonyl]amino}thiophene-3-carboxamide;

N-(2-aminoethyl)-5-(4-methoxyphenyl)-2-{[(pyrazin-2-ylamino)carbonyl]amino}thiophene-3-carboxamide;

5-{4-[2-(diethylamino)ethoxy]phenyl}-N-piperidin-3-yl-2-{[(pyrazin-2-ylamino)carbonyl]amino}thiophene-3-carboxamide;

5-(4-methoxyphenyl)-N-piperidin-4-yl-2-{[(pyrazin-2-ylamino)carbonyl]amino}thiophene-3-carboxamide;

tert-butyl 3-{[(5-{3-[2-(diethylamino)ethoxy]phenyl}-2-{[(pyrazin-2-ylamino)carbonyl]amino}-3-thienyl)carbonyl]amino}piperidine-1-carboxylate;

5-{4-[2-(diethylamino)ethoxy]phenyl}-N-piperidin-4-yl-2-{[(pyrazin-2-ylamino)carbonyl]amino}thiophene-3-carboxamide;

5-(4-methoxyphenyl)-2-{[(pyrazin-2-ylamino)carbonyl]amino}-N-[(3S)-pyrrolidin-3-yl]thiophene-3-carboxamide;

N-[3-(1,4-diazepan-1-ylcarbonyl)-5-(4-methoxyphenyl)-2-thienyl]-N'-pyrazin-2-ylurea;

N-[3-[(3-aminopyrrolidin-1-yl)carbonyl]-5-(4-methoxyphenyl)-2-thienyl]-N'-pyrazin-2-ylurea;

tert-butyl 4-{[(5-(4-methoxyphenyl)-2-{[(pyrazin-2-ylamino)carbonyl]amino}-3-thienyl)carbonyl]amino}piperidine-1-carboxylate;

tert-butyl 3-{[(5-{4-[2-(diethylamino)ethoxy]phenyl}-2-{[(pyrazin-2-ylamino)carbonyl]amino}-3-thienyl)carbonyl]amino}piperidine-1-carboxylate;

5-[4-(2-diethylamino-ethoxy)-phenyl]-2-(3-hydroxy-urea)-thiophene-3-carboxylic acid-(S)-piperidin-3-ylamide;

2-[(aminocarbonyl)amino]-N-[(3S)-azepan-3-yl]-5-(3-methoxyphenyl)thiophene-3-carboxamide;

2-[(aminocarbonyl)amino]-5-(2-hydroxyphenyl)-N-[(3S)-piperidin-3-yl]thiophene-3-carboxamide;

2-[(aminocarbonyl)amino]-5-(3-methoxyphenyl)-N-[(3S)-piperidin-3-yl]thiophene-3-carboxamide;

2-[(aminocarbonyl)amino]-5-[2-(benzyloxy)phenyl]-N-[(3S)-piperidin-3-yl]thiophene-3-carboxamide.

17. A pharmaceutical composition comprising a compound of formula (I) or a pharmaceutically acceptable salt thereof as defined in claim 1 together with at least one pharmaceutically acceptable carrier, diluent or excipient.

* * * * *